US012285462B2

(12) United States Patent
Reshetnyak et al.

(10) Patent No.: US 12,285,462 B2
(45) Date of Patent: Apr. 29, 2025

(54) pH-TRIGGERED MEMBRANE PEPTIDE-MEDIATED EPITOPE TETHERING AT CELL SURFACES

(71) Applicants: UNIVERSITY OF RHODE ISLAND BOARD OF TRUSTEES, Kingston, RI (US); YALE UNIVERSITY, New Haven, CT (US)

(72) Inventors: Yana K. Reshetnyak, Saunderstown, RI (US); Oleg A. Andreev, Saunderstown, RI (US); Anna Moshnikova, Warwick, RI (US); Donald M. Engelman, New Haven, CT (US)

(73) Assignees: University of Rhode Island Board of Trustees, Kingston, RI (US); Yale University, New Haven, CT (US)

( * ) Notice: Subject to any disclaimer, the term of this patent is extended or adjusted under 35 U.S.C. 154(b) by 0 days.

(21) Appl. No.: 18/325,884

(22) Filed: May 30, 2023

(65) Prior Publication Data

US 2024/0066096 A1 Feb. 29, 2024

Related U.S. Application Data

(63) Continuation of application No. 16/775,113, filed on Jan. 28, 2020, now abandoned.

(60) Provisional application No. 62/797,899, filed on Jan. 28, 2019.

(51) Int. Cl.

| | |
|---|---|
| ***A61K 38/00*** | (2006.01) |
| ***A61K 38/16*** | (2006.01) |
| ***A61K 38/19*** | (2006.01) |
| ***A61K 38/20*** | (2006.01) |
| *A61K 45/00* | (2006.01) |
| *A61K 47/00* | (2006.01) |
| *A61K 47/10* | (2017.01) |

(52) U.S. Cl.

CPC ............ *A61K 38/16* (2013.01); *A61K 38/195* (2013.01); *A61K 38/20* (2013.01); *A61K 45/05* (2013.01); *A61K 47/00* (2013.01); *A61K 47/10* (2013.01); *A61K 2121/00* (2013.01); *C07K 2319/33* (2013.01)

(58) Field of Classification Search

CPC .. A61K 2121/00; A61K 38/16; A61K 38/195; A61K 38/20; A61K 45/05; A61K 47/00; A61K 47/10; C07K 2319/33

See application file for complete search history.

(56) References Cited

U.S. PATENT DOCUMENTS

| | | | | |
|---|---|---|---|---|
| 8,076,451 | B2 | 12/2011 | Reshetnyak et al. | |
| 8,703,909 | B2 | 4/2014 | Reshetnyak et al. | |
| 8,846,081 | B2 | 9/2014 | Reshetnyak et al. | |
| 9,289,508 | B2 | 3/2016 | Reshetnyak et al. | |
| 9,676,823 | B2 | 6/2017 | Reshetnyak et al. | |
| 9,750,693 | B2 | 9/2017 | Reshetnyak et al. | |
| 9,814,781 | B2 | 11/2017 | Reshetnyak et al. | |
| 10,512,606 | B2 | 12/2019 | Reshetnyak et al. | |
| 11,229,710 | B2 | 1/2022 | Reshetnyak et al. | |
| 11,267,853 | B2 | 3/2022 | Reshetnyak et al. | |
| 11,274,126 | B2 | 3/2022 | Reshetnyak et al. | |
| 11,738,096 | B2 | 8/2023 | Reshetnyak et al. | |
| 11,779,662 | B2 | 10/2023 | Reshetnyak et al. | |
| 11,857,509 | B2 | 1/2024 | Reshetnyak et al. | |
| 12,029,793 | B2 | 7/2024 | Reshetnyak et al. | |
| 2007/0160571 | A1 | 7/2007 | Krathwohl | |
| 2008/0233107 | A1 * | 9/2008 | Reshetnyak ......... | C07K 14/001 424/94.4 |
| 2012/0039990 | A1 | 2/2012 | Reshetnyak et al. | |
| 2012/0142042 | A1 | 6/2012 | Reshetnyak et al. | |
| 2013/0136763 | A1 * | 5/2013 | Song ....................... | A61P 31/00 424/192.1 |
| 2015/0051153 | A1 | 2/2015 | Reshetnyak et al. | |
| 2015/0086617 | A1 | 3/2015 | Reshetnyak et al. | |
| 2015/0190471 | A1 * | 7/2015 | Copik .................... | A61K 38/17 435/375 |
| 2015/0191508 | A1 | 7/2015 | Reshetnyak et al. | |
| 2016/0229901 | A1 | 8/2016 | Merchant | |
| 2016/0256560 | A1 | 9/2016 | Reshetnyak et al. | |
| 2018/0057594 | A1 | 3/2018 | Evnin | |
| 2018/0064648 | A1 | 3/2018 | Reshetnyak et al. | |
| 2018/0117183 | A1 * | 5/2018 | Reshetnyak ......... | A61B 5/0082 |

(Continued)

FOREIGN PATENT DOCUMENTS

| | | |
|---|---|---|
| WO | WO-2006078816 A2 | 7/2006 |
| WO | WO-2012021790 A1 | 2/2012 |

(Continued)

OTHER PUBLICATIONS

Altschul et al., "Basic Local Alignment Search Tool," J. Mol. Biol. 215:403-410 (1990).

Altschul et al., "Gapped BLAST and PSI-BLAST: A New Generation of Protein Database Search Programs," Nucl. Acids Res. 25(17):3389-3402 (1997).

(Continued)

*Primary Examiner* — Aradhana Sasan

*Assistant Examiner* — Mercy H Sabila

(74) *Attorney, Agent, or Firm* — Sterne, Kessler, Goldstein & Fox P.L.L.C.

(57) ABSTRACT

The invention features methods and compositions for eliciting an anti-tumor response in a subject comprising administering to the subject a pHLIP® construct comprising an antibody recruiting molecule linked to one or more pHLIP® peptides by a non-cleavable linker compound. The construct increases the amount of the antibody recruiting molecule on the surface of a diseased cell.

18 Claims, 7 Drawing Sheets

Specification includes a Sequence Listing.

(56) References Cited

U.S. PATENT DOCUMENTS

| | | | |
|---|---|---|---|
| 2018/0221500 A1 | 8/2018 | Reshetnyak et al. |
| 2018/0369425 A1 | 12/2018 | Reshetnyak et al. |
| 2019/0231904 A1 | 8/2019 | Reshetnyak et al. |
| 2019/0382448 A1 | 12/2019 | Reshetnyak et al. |
| 2020/0237926 A1 | 7/2020 | Reshetnyak et al. |
| 2020/0246420 A1 | 8/2020 | Reshetnyak et al. |
| 2020/0253872 A1 | 8/2020 | Reshetnyak et al. |
| 2020/0262881 A1 | 8/2020 | Reshetnyak et al. |
| 2020/0323882 A1 | 10/2020 | Reshetnyak et al. |
| 2022/0088208 A1 | 3/2022 | Reshetnyak et al. |
| 2022/0281919 A1 | 9/2022 | Reshetnyak et al. |
| 2024/0042063 A1 | 2/2024 | Reshetnyak et al. |
| 2024/0075170 A1 | 3/2024 | Reshetnyak et al. |
| 2024/0148911 A1 | 5/2024 | Reshetnyak et al. |
| 2024/0173258 A1 | 5/2024 | Reshetnyak et al. |

FOREIGN PATENT DOCUMENTS

| | | |
|---|---|---|
| WO | WO-2012047354 A2 | 4/2012 |
| WO | WO-2017165452 A1 | 9/2017 |
| WO | WO-2018057912 A1 | 3/2018 |
| WO | WO-2018227132 A1 | 12/2018 |
| WO | WO-2020159983 A1 | 8/2020 |
| WO | WO-2020160009 A1 | 8/2020 |
| WO | WO-2020160031 A1 | 8/2020 |
| WO | WO-2020160047 A2 | 8/2020 |
| WO | WO-2020190733 A1 | 9/2020 |
| WO | WO-2024040027 A2 | 2/2024 |

OTHER PUBLICATIONS

Database Genebank, "Interleukin-6 Isoform 1 Precursor [*Homo sapiens*]," Genebank Reference Sequence NP_000591.1, 3 pages (Sep. 5, 2016.

Genebank, "C-X-C Motif Chemokine 10 Precursor [*Homo sapiens*]," Accession No. NP_001556.2, 3 pages (Feb. 9, 2020).

Genebank, "C-X-C Motif Chemikine 11 Isoform 1 Precursor [*Homo Sapiens*]," Accession No. NP_005400.1, 3 pages (Jan. 27, 2020).

Genebank, "C-X-C Motif Chemokine 9 Precursor [*Homo sapiens*]," Accession No. NP_002407.1, 3 pages (Mar. 1, 2020).

Genebank, "Frractalkine Isoform 1 Precursor [*Homo sapiens*]," Accession No. NP_002987.1, 4 pages (Mar. 29, 2020).

Genebank, "*Homo sapiens* C-X-C Motif Chemokine Ligand 10 (CXCL10), mRNA," Accession No. NM_001565.4, 3 pages (Feb. 9, 2020).

Genebank, "*Homo sapiens* C-X-C Motif Chemokine Ligand 11 (CXCL11), Transcript Variant 1, mRNA," Accession No. NM_005409.5, 3 pages (Jan. 27, 2020).

Genebank, "*Homo sapiens* C-X-C Motif Chemikine Ligand 9 (CXCL9), mRN," Accession No. MN_002416.3, 3 pages (Mar. 1, 2020).

Genebank, "*Homo sapiens* erb-b2 Receptor Tyrosine Kinase 2 (ERBB2), Transcript Variant 2, mRNA," Accession No. NM_001005862.2, 6 pages (Mar. 28, 2020).

Genebank, "*Homo sapiens* Interleukin 12 mRNA, Complete Cds," Accession No. AF101062.1, 1 page (Mar. 3, 1999).

Genebank, "*Homo sapiens* Interleukin 12B (IL12B), mRNA," Accession No. NM_002187.3, 4 pages (Mar. 29, 2020).

Genebank, "*Homo sapiens* Interleukin 2 (IL2), mRNA," Accession No. NM_00586.4, 3 pages (Mar. 22, 2020).

Genebank, "*Homo sapiens* Interleukin 6 (IL6), Transcript Variant 1, mRNA," Accession No. NM_000600.5 3 pages (Mar. 28, 2020).

Genebank, "*Homo sapiens* Interleukin 7 (IL7), Transcript Variant 1, mRNA," Accession No. NM_000880.4, 4 pages (Feb. 16, 2020).

Genebank, "*Homo sapiens* Tumor Necrosis Factor (TNF), mRNA," Accession No. NM_000594.4, 4 pages (Mar. 28, 2020).

Genebank, "Interleukin 2 [*Homo sapiens*]," Accession No. NP_000577.1, 2 pages (Oct. 31, 2000).

Genebank, "Interleukin-7 Isoform 1 Precursor [*Homo sapiens*]," Accession No. NP_000871.1, 3 pages (Feb. 16, 2020).

Genbank, "Receptor tyrosine-protein kinase erbB-2 isoform b [*Homo sapiens*]," Accession No. NP_001005862.1, 4 pages (Mar. 28, 2020).

Genbank, "Tumor Necrosis Factor [*Homo sapiens*]," Accession No. NP_000585.2.

Henikoff et al., "Amino Acid Substitution Matrices from Protein Blocks," PNAS USA 89(22):10915-10919 (Nov. 15, 1992).

Krause et al., "Tyrosine Kinases as Targets for Cancer Therapy," New England Journal of Medicine 353(2):172-187 (Jul. 14, 2005).

Needleman et al., "A General Method Applicable to the Search for Similarities in the Amino Acid Sequence of Two Proteins," J. Mol. Biol. 48(3):443-342 (Mar. 28, 1970).

Pearson et al., "Improved Tools for Biological Sequence Comparison," PNAS 85:2444-2448 (Apr. 1988).

Smith et al., "Comparison of Biosequences," Adv. Appl. Math. 2(4):482-489 (Dec. 1981).

Uniprot, "Interleukin-12 Subunit Alpha," Accession No. P29459 (Apr. 1, 1993).

Uniprot, "Interleukin-12 Subunit Beta," Accession No. P29460 (Apr. 1, 1993).

Weerakkody et al., "Family of pH (low) insertion peptides for tumor targeting," PNAS 110(15):5834-5839 (Apr. 9, 2013).

Office Action mailed Feb. 9, 2022, in U.S. Appl. No. 16/775,113, Reshetnyak et al., filed Jan. 28, 2020, 13 pages.

Office Action mailed Sep. 7, 2022, in U.S. Appl. No. 16/775,113, Reshetnyak et al., filed Jan. 28, 2020, 11 pages.

Office Action mailed Feb. 27, 2023, in U.S. Appl. No. 16/775,113, Reshetnyak et al., filed Jan. 28, 2020, 21 pages.

Jung et al., "Impact of Hapten Presentation on Antibody Binding at Lipid Membrane Interfaces," Biophysical Journal, Apr. 15, 2008, 84(8):P3094-3103.

Muenchmeier et al., "A Novel CXCL10-Based GPI-Anchored Fusion Protein as Adjuvant in NK-Based Tumor Therapy," Plos One, Aug. 30, 2013, 8(8):e72749.

McEnaney et al., "Antibody-Recruiting Molecules: An Emerging Paradigm for Engaging Immune Function in Treating Human Disease," ACS Chemical Biology, Jul. 20, 2012, 7(7):1139-1151.

Co-pending U.S. Appl. No. 18/499,655, inventors: Reshetnyak et al., filed Nov. 1, 2023 (Not Published).

Co-pending U.S. Appl. No. 18/349,851, inventors: Reshetnyak et al., filed Jul. 10, 2023 (Not Published).

Co-pending U.S. Appl. No. 18/349,855, inventors: Reshetnyak et al., filed Jul. 10, 2023 (Not Published).

Co-pending U.S. Appl. No. 18/608,699, inventors: Reshetnyak et al., filed Mar. 18, 2024 (Not Published).

International Search Report and Written Opinion corresponding to International Patent Application No. PCT/US2017/023458, ISA/US, United States, mailed Aug. 25, 2017, 21 pages.

Krause et al., "Epitopes Expressed in Different Adenovirus Capsid Proteins Induce Different Levels of Epitope-Specific Immunity," Journal of Virology, Jun. 2006, 80(11): 5523-5530.

* cited by examiner 96401783v.1 pH-TRIGGERED MEMBRANE PEPTIDE-MEDIATED EPITOPE TETHERING AT CELL SURFACES

RELATED APPLICATIONS

This application claims the benefit of priority under 35 U.S.C. § 119(e) to U.S. Provisional Application No. 62/797,899, filed Jan. 28, 2019, the entire contents of which is incorporated herein by reference in its entirety.

STATEMENT AS TO FEDERALLY SPONSORED RESEARCH

This invention was made with government support under R01 GM073857 awarded by the National Institute of General Medical Sciences of the National Institutes of Health. The government has certain rights in the invention.

INCORPORATION BY REFERENCE OF SEQUENCE LISTING

The contents of the sequence listing text file named "040984-512001WO_SL.txt", which was created on Feb. 22, 2021 and is 228 kilobytes in size, is hereby incorporated by reference in its entirety.

FIELD OF THE INVENTION

The present invention relates to immunotherapy.

BACKGROUND

Antibody therapies are based on the alteration of signaling, promotion of apoptosis, sequestration of growth factors, activation of the immune system, and delivery of drugs as antibody-drug conjugates (ADCs). Antibodies find their target cells by recognizing specific signaling molecules (epitopes) exposed by a cell. Epitopes bind and/or attract endogenous (natural) antibodies, exogenous antibodies, ADCs administrated into the body, or antibodies which are produced (generated) in the course of vaccination. Also cytokines, which are small immune-modulating proteins can activate or suppress an immune response depending on their features, concentration and local environment. Numerous highly specific humanized monoclonal antibodies such as trastuzumab (Herceptin), and antibody-cytokine fusion proteins have been developed and are in clinical use (or clinical trials), which target epitopes that are more abundant in a diseased tissue than in a normal tissue. However, their use is limited by (1) the lack of adequate amounts (or any amounts) of accessible epitopes in many cancers, and (2) the emergence of resistance by selection of expression mutants not presenting proper epitopes.

SUMMARY OF THE INVENTION

The invention provides a solution to the limitations of existing therapeutic approaches by utilizing a strategy in which a desired epitope is positioned on cell surfaces in diseased tissues, such as tumors or inflamed tissues. Positioning the epitope on the cell surface, (e.g., preferentially in diseased tissues), is a great advantage and enhances the recruitment of cells of the immune system or endogenous antibodies, and enhances the use of developed monoclonal antibodies such as trastuzumab (Herceptin), antibody-drug conjugates, and antibodies generated in the course of vaccination. The invention further provides compositions and methods to augment any amount of particular epitopes at cell surfaces for immunoregulation and efficient binding of immune cells, antibodies and ADCs.

Provided herein are compositions and methods for the decoration of target cells with epitopes, e.g., a protein, a peptide, or a small molecule epitope, that can (1) recruit immune cells (or exogenous engineered T-cells and NK-cells), (2) recruit endogenous antibodies, (3) enhance the use of the exogenous antibodies or ADCs administrated into body, and (4) enhance the use of antibodies, which are produced (generated) in the course of vaccination leading to cell death.

Tumors are characterized by a tumor micro environment (TME) of a lower pH than the surrounding tissues, because of the metabolism accompanying their rapid and uncontrolled cell proliferation, which results in a flux of acidity emerging from the cancer cells. Moreover, due to the flux and the membrane potential, the extracellular pH is lowest at the surfaces of cancer cells and is significantly lower than the bulk extracellular pH in tumors. The low pH region persists at the cancer cell surfaces even in well-perfused tumor areas.

A pH Low Insertion Peptide (pHLIP®) is a water-soluble membrane peptide that interacts weakly with a cell membrane at neutral pH, without insertion into the lipid bilayer; however, at slightly acidic pH (<7.0), a pHLIP® inserts into the cell membrane and, if it is long enough and non-cyclic, can form a stable transmembrane alpha-helix. In addition to tumor cells characterized by low pH (<7.0), immune cells within a tumor mass are also characterized by low pH (<7.0). For example, the cells within the environment of a tumor mass, e.g., macrophages, are also characterized by a low surface pH.

By binding (linking and/or conjugating) a pHLIP®, or pHLIP® equivalent, to an epitope, it is possible to specifically target the cell and decorate a tumor cell or cells in inflamed tissues with epitopes to recognize or recruit endogenous (natural) immune cells or antibodies circulating in the blood, promote and enhance binding of exogenous engineered T-cells and NK-cells or antibodies or ADCs administrated into body, or antibodies, which are generated in the course of vaccination and thereby promote cell killing. A significant advantage of this approach is that the pHLIP® constructs described herein are associated with few to no side effects for the patient due to the targeted delivery of epitopes to the cell surfaces. The epitope may be of mammalian origin, viral origin, or bacterial origin.

Accordingly, the invention features a composition comprising an epitope conjugated to a pH-triggered membrane peptide (pHLIP®) comprising at least 4 amino acids. For example, the pHLIP® peptide may be a linear peptide or a cyclic peptide, e.g., as described in PCT Application No. PCT/US2017/023458. The epitope is selectively positioned on the surface of the cell in targeted diseased tissue by pHLIP® to mediate or enhance immune cells (lymphocytes) recruitment and adhesion, antibody binding and induce cell killing predominantly in diseased tissue (tumor). The composition comprises an epitope conjugated to pHLIP®, and the pHLIP® targets epitope to the cell surface.

Accordingly, the method of eliciting an anti-tumor response in a subject comprises administering to a subject, e.g., a human subject, a pHLIP® construct comprising an antibody or lymphocyte recruiting molecule linked to one or more pHLIP® peptides by a non-cleavable linker compound, wherein the construct increases the amount of the immune cell or the antibody recruiting molecule on the surface of a diseased cell. For example, the diseased cell comprises a tumor cell.

In some examples, the antibody recruiting molecule comprises an epitope, e.g., an epitope (e.g., a peptide epitope) with a length less than 500 amino acids. For example, the peptide epitope comprises a length of between 5 to 20 amino acids, e.g., 5, 6, 7, 8, 9, 10, 11, 12, 13, 14, 15, 16, 17, 18, 19, or 20 amino acids. In some embodiments, the peptide epitope is a human epidermal growth factor 2 (HER2) peptide, e.g., a HER2 peptide selected from the group consisting of (SEQ ID NO: 1)
QVSHWVSGLAEGSFG, (SEQ ID NO: 2)
LSHTSGRVEGSVSLL,
and (SEQ ID NO: 3)
QMWAPQWGPD.

The human amino acid sequence of HER2 is provided below and is incorporated herein by reference (NCBI GenBank NP_001005862.1 or UniProt P04626).

(SEQ ID NO: 485)

```
   1 mklrlpaspe thldmlrhly qgcqvvqgnl eltylptnas lsflqdiqev qgyvliahnq
  61 vrqvplqrlr ivrgtqlfed nyalavldng dplnnttpvt gaspgglrel qlrslteilk
 121 ggvliqrnpq lcyqdtilwk difhknnqla ltlidtnrsr achpcspmck gsrcwgesse
 181 dcqsltrtvc aggcarckgp lptdccheqc aagctgpkhs dclaclhfnh sgicelhcpa
 241 lvtyntdtfe smpnpegryt fgascvtacp ynylstdvgs ctlvcplhnq evtaedgtqr
 301 cekcskpcar vcyglgmehl revravtsan iqefagckki fgslaflpes fdgdpasnta
 361 plqpeqlqvf etleeitgyl yisawpdslp dlsvfqnlqv irgrilhnga ysltlqglgi
 421 swlglrslre lgsglalihh nthlcfvhtv pwdqlfrnph qallhtanrp edecvgegla
 481 chqlcarghc wgpgptqcvn csqflrgqec veecrvlqgl preyvnarhc lpchpecqpq
 541 ngsvtcfgpe adqcvacahy kdppfcvarc psgvkpdlsy mpiwkfpdee gacqpcpinc
 601 thscvdlddk gcpaeqrasp ltsiisavvg illvvvlgvv fgilikrrqq kirkytmrrl
 661 lqetelvepl tpsgampnqa qmrilketel rkvkvlgsga fgtvykgiwi pdgenvkipv
 721 aikvlrents pkankeilde ayvmagvgsp yvsrllgicl tstvqlvtql mpygclldhv
 781 renrgrlgsq dllnwcmqia kgmsyledvr lvhrdlaarn vlvkspnhvk itdfglarll
 841 dideteyhad ggkvpikwma lesilrrrft hqsdvwsygv tvwelmtfga kpydgipare
 901 ipdllekger lpqppictid vymimvkcwm idsecrprfr elvsefsrma rdpqrfvviq
 961 nedlgpaspl dstfyrslle dddmgdlvda eeylvpqqgf fcpdpapgag gmvhhrhrss
1021 strsgggdlt lglepseeea prsplapseg agsdvfdgdl gmgaakglqs lpthdpsplq
1081 rysedptvpl psetdgyvap ltcspqpeyv nqpdvrpqpp spregplpaa rpagatlerp
1141 ktlspgkngv vkdvfafgga venpeyltpq ggaapqphpp pafspafdnl yywdqdpper
1201 gappstfkgt ptaenpeylg ldvpv
```

Exemplary landmark residues, domains, and fragments of HER2 include, but are not limited to residues 22-143 (Receptor L domain), residues 159-308 (furin like domain), or 611-654 (transmembrane domain of Erb2 (receptor tyrosine-protein kinase). A fragment (e.g., a peptide or an epitope) of a HER2 protein is less than the length of the full length protein, e.g., a fragment is at least 3, 4, 5, 6, 7, 8, 9, 10, 20, 30, 40, 50, 100, 200 or more residues in length, but less than e.g., 1225 residues in the case of HER2 above. Additionally, HER2 may include a signal sequence (melaalcrwglllallppgaastqvctgtd SEQ ID NO: 516, which gets cleaved to form the mature protein).

The human HER2 nucleic acid sequence is provided below and is incorporated herein by reference (start and stop codons are underlined; NCBI GenBank: NM_001005862.2).

(SEQ ID NO: 486)

1 aagttcctgt gttctttatt ctactctccg ctgaagtcca cacagtttaa attaaagttc 61 ccggattttt gtgggcgcct gccccgcccc tcgtcccccct gctgtgtcca tatatcgagg 121 cgatagggtt aagggaaggc ggacgcctga tgggttaatg agcaaactga agtgttttcc 181 atgatctttt ttgagtcgca attgaagtac cacctcccga gggtgattgc ttccccatgc 241 ggggtagaac ctttgctgtc ctgttcacca ctctacctcc agcacagaat ttggcttatg 301 cctactcaat gtgaagatga tgaggatgaa aacctttgtg atgatccact tccacttaat 361 gaatggtggc aaagcaaagc tatattcaag accacatgca aagctactcc ctgagcaaag 421 agtcacagat aaaacggggg caccagtaga atggccagga caaacgcagt gcagcacaga 481 gactcagacc ctggcagcca tgcctgcgca ggcagtgatg agagtgacat gtactgttgt 541 ggacatgcac aaaagtgagt gtgcaccggc acagacatga agctgcggct ccctgccagt 601 cccgagaccc acctggacat gctccgccac ctctaccagg gctgccaggt ggtgcaggga 661 aacctggaac tcacctacct gcccaccaat gccagcctgt ccttcctgca ggatatccag 721 gaggtgcagg gctacgtgct catcgctcac aaccaagtga ggcaggtccc actgcagagg 781 ctgcggattg tgcgaggcac ccagctcttt gaggacaact atgccctggc cgtgctagac 841 aatggagacc cgctgaacaa taccacccct gtcacagggg cctccccagg aggcctgcgg 901 gagctgcagc ttcgaagcct cacagagatc ttgaaaggag gggtcttgat ccagcggaac 961 ccccagctct gctaccagga cacgattttg tggaaggaca tcttccacaa gaacaaccag 1021 ctggctctca cactgataga caccaaccgc tctcgggcct gccacccctg ttctccgatg 1081 tgtaagggct cccgctgctg gggagagagt tctgaggatt gtcagagcct gacgcgcact 1141 gtctgtgccg gtggctgtgc ccgctgcaag gggccactgc ccactgactg ctgccatgag 1201 cagtgtgctg ccggctgcac gggccccaag cactctgact gcctggcctg cctccacttc 1261 aaccacagtg gcatctgtga gctgcactgc ccagccctgg tcacctacaa cacagacacg 1321 tttgagtcca tgcccaatcc cgagggccgg tatacattcg gcgccagctg tgtgactgcc 1381 tgtccctaca actacctttc tacggacgtg ggatcctgca ccctcgtctg ccccctgcac 1441 aaccaagagg tgacagcaga ggatggaaca cagcggtgtg agaagtgcag caagccctgt 1501 gcccgagtgt gctatggtct gggcatggag cacttgcgag aggtgagggc agttaccagt 1561 gccaatatcc aggagtttgc tggctgcaag aagatctttg ggagcctggc atttctgccg 1621 gagagctttg atggggaccc agcctccaac actgccccgc tccagccaga gcagctccaa 1681 gtgtttgaga ctctggaaga gatcacaggt tacctataca tctcagcatg gccggacagc 1741 ctgcctgacc tcagcgtctt ccagaacctg caagtaatcc ggggacgaat tctgcacaat 1801 ggcgcctact cgctgaccct gcaagggctg ggcatcagct ggctggggct gcgctcactg 1861 agggaactgg gcagtggact ggccctcatc caccataaca cccacctctg cttcgtgcac 1921 acggtgccct gggaccagct ctttcggaac ccgcaccaag ctctgctcca cactgccaac 1981 cggccagagg acgagtgtgt gggcgagggc ctggcctgcc accagctgtg cgcccgaggg 2041 cactgctggg gtccagggcc cacccagtgt gtcaactgca gccagttcct tcggggccag -continued

```
2101 gagtgcgtgg aggaatgccg agtactgcag gggctcccca gggagtatgt gaatgccagg
2161 cactgtttgc cgtgccaccc tgagtgtcag ccccagaatg gctcagtgac ctgttttgga
2221 ccggaggctg accagtgtgt ggcctgtgcc cactataagg accctccctt ctgcgtggcc
2281 cgctgcccca gcggtgtgaa acctgacctc tcctacatgc ccatctggaa gtttccagat
2341 gaggagggcg catgccagcc ttgccccatc aactgcaccc actcctgtgt ggacctggat
2401 gacaagggct gccccgccga gcagagagcc agccctctga cgtccatcat ctctgcggtg
2461 gttggcattc tgctggtcgt ggtcttgggg gtggtctttg ggatcctcat caagcgacgg
2521 cagcagaaga tccggaagta cacgatgcgg agactgctgc aggaaacgga gctggtggag
2581 ccgctgacac ctagcggagc gatgcccaac caggcgcaga tgcggatcct gaaagagacg
2641 gagctgagga aggtgaaggt gcttggatct ggcgcttttg gcacagtcta caagggcatc
2701 tggatccctg atggggagaa tgtgaaaatt ccagtggcca tcaaagtgtt gagggaaaac
2761 acatccccca aagccaacaa agaaatctta gacgaagcat acgtgatggc tggtgtgggc
2821 tccccatatg tctcccgcct tctgggcatc tgcctgacat ccacggtgca gctggtgaca
2881 cagcttatgc cctatggctg cctcttagac catgtccggg aaaaccgcgg acgcctgggc
2941 tcccaggacc tgctgaactg gtgtatgcag attgccaagg ggatgagcta cctggaggat
3001 gtgcggctcg tacacaggga cttggccgct cggaacgtgc tggtcaagag tcccaaccat
3061 gtcaaaatta cagacttcgg gctggctcgg ctgctggaca ttgacgagac agagtaccat
3121 gcagatgggg gcaaggtgcc catcaagtgg atggcgctgg agtccattct ccgccggcgg
3181 ttcacccacc agagtgatgt gtggagttat ggtgtgactg tgtgggagct gatgactttt
3241 ggggccaaac cttacgatgg gatcccagcc cgggagatcc ctgacctgct ggaaaagggg
3301 gagcggctgc cccagccccc catctgcacc attgatgtct acatgatcat ggtcaaatgt
3361 tggatgattg actctgaatg tcggccaaga ttccgggagt tggtgtctga attctcccgc
3421 atggccaggg acccccagcg ctttgtggtc atccagaatg aggacttggg cccagccagt
3481 cccttggaca gcaccttcta ccgctcactg ctggaggacg atgacatggg ggacctggtg
3541 gatgctgagg agtatctggt accccagcag ggcttcttct gtccagaccc tgccccgggc
3601 gctgggggca tggtccacca caggcaccgc agctcatcta ccaggagtgg cggtggggac
3661 ctgacactag ggctggagcc ctctgaagag gaggccccca ggtctccact ggcaccctcc
3721 gaaggggctg gctccgatgt atttgatggt gacctgggaa tgggggcagc caaggggctg
3781 caaagcctcc ccacacatga ccccagccct ctacagcggt acagtgagga ccccacagta
3841 cccctgccct ctgagactga tggctacgtt gcccccctga cctgcagccc ccagcctgaa
3901 tatgtgaacc agccagatgt tcggccccag cccccttcgc cccgagaggg ccctctgcct
3961 gctgcccgac ctgctggtgc cactctggaa aggcccaaga ctctctcccc agggaagaat
4021 ggggtcgtca aagacgtttt tgcctttggg ggtgccgtgg agaaccccga gtacttgaca
4081 ccccagggag gagctgcccc tcagccccac cctcctcctg ccttcagccc agccttcgac
4141 aacctctatt actgggacca ggacccacca gagcgggggg ctccacccag caccttcaaa
4201 gggacaccta cggcagagaa cccagagtac ctgggtctgg acgtgccagt gtgaaccaga
4261 aggccaagtc cgcagaagcc ctgatgtgtc ctcagggagc agggaaggcc tgacttctgc
4321 tggcatcaag aggtgggagg gccctccgac cacttccagg ggaacctgcc atgccaggaa
4381 cctgtcctaa ggaaccttcc ttcctgcttg agttcccaga tggctggaag gggtccagcc
4441 tcgttggaag aggaacagca ctggggagtc tttgtggatt ctgaggccct gcccaatgag
```

-continued

```
4501 actctagggt ccagtggatg ccacagccca gcttggccct ttccttccag atcctgggta

4561 ctgaaagcct tagggaagct ggcctgagag gggaagcggc cctaagggag tgtctaagaa

4621 caaaagcgac ccattcagag actgtccctg aaacctagta ctgcccccca tgaggaagga

4681 acagcaatgg tgtcagtatc caggctttgt acagagtgct tttctgttta gtttttactt

4741 tttttgtttt gtttttttaa agatgaaata aagacccagg gggagaatgg gtgttgtatg

4801 gggaggcaag tgtgggggt ccttctccac acccactttg tccatttgca aatatatttt

4861 ggaaaacagc taaaaaaaaa aaaaaaaaa
```

Exemplary landmark residues, domains, and fragments of HER2 include, but are not limited to residues 57-4254 (coding region), residues 4767-4772 (polyA signal sequence), 4787 (polyA site), or 4872 (polyA site).

In other example, the peptide (epitope peptide) comprises a mammalian peptide, a viral peptide, or a bacterial peptide. For example, the peptide is selected from the group consisting of MASMTGGQQMG (SEQ ID NO: 4)—T7 peptide derived from the T7 major capsid protein; EQKLISEEDL (SEQ ID NO: 5)—Myc peptide derived from c-Myc; YPYDVPDYA (SEQ ID NO: 6)—hemagglutinin (HA) peptide derived from hemagglutinin; YTDIEMNRLGK (SEQ ID NO: 7)—vesiculovirus (VSV-G) peptide derived from the vesicular stomatitis viral glycoprotein; KETAAAKFERQHMDS (SEQ ID NO: 8)—S peptide derived from pancreatic ribonuclease A; GKPIPNPLLGLDST (SEQ ID NO: 9)—V5 peptide derived from the P and V proteins of the paramyxovirus of simian virus 5; DYKDDDDK (SEQ ID NO: 10) FLAG synthetic peptide; GAPVPYPDPLEPR (SEQ ID NO: 11)—E synthetic peptide; HHHHHH (SEQ ID NO: 12)—Histidine synthetic peptide; TKENPRSNQEESYDDNES (SEQ ID NO: 13)—NE-tag synthetic peptide; WSHPQFEK (SEQ ID NO: 14)—synthetic peptide recognized by streptavidin; PDRVRAVSHWSS (SEQ ID NO: 15)—peptide derived from the protein beta-catenin and optimized for higher affinity binding to the Spot-Tag Nanobody; and YTDIEMNRLGK (SEQ ID NO: 7)—vesicular stomatitis virus (VSV) synthetic peptide.

In some examples, the immune cell (e.g., a lymphocyte) recruiting molecule comprises a cytokine protein or a cytokine protein epitope. For example, the cytokine protein is less than 200 amino acids. In other examples, the cytokine protein is up to 350 amino acids. Exemplary cytokine protein epitopes include interleukin 2 (IL-2), interleukin 6 (IL-6), interleukin-7 (IL-7), interleukin-12 (IL-12), a tumor necrosis factor (TNF), or chemokines including α-chemokines or CXC chemokines, where CXC stands for Cys-X-Cys motif, and β-chemokines or CC chemokines, where CC stands for Cys-Cys motif near their amino terminus.

An exemplary chemokine comprises the human protein epitope C-X-C motif chemokine 10 (CXCL10) or Interferon gamma-induced protein 10 (IP-10) (UniProt P02778 or NP_001556.2, incorporated herein by reference), and an exemplary sequence comprises the amino acid sequence:

```
                                             (SEQ ID NO: 514)
 1  mnqtailicc lifltlsgiq gvplsrtvrc tcisisnqpv nprsleklei

61  ipasqfcprv eiiatmkkkg ekrclnpesk aiknllkavs kerskrsp
```

Exemplary landmark residues, domains, and fragments of CXCL10 include, but are not limited to residues 1-21 (signal peptide), residues 22-98 (mature peptide). A fragment (e.g., a peptide or an epitope) of a CXCL10 protein is less than the length of the full length protein, e.g., a fragment is at least 3, 4, 5, 6, 7, 8, 9, 10, 20, 30, 40, 50, 100 or more residues in length, but less than e.g., 108 residues in the case of CXCL10 above.

The human CXCL10 nucleic acid sequence is provided below and is incorporated herein by reference (start and stop codons are underlined; NCBI GenBank: NM_001565.4).

```
                                                          (SEQ ID NO: 517)
  1 gagacattcc tcaattgctt agacatattc tgagcctaca gcagaggaac ctccagtctc

 61 agcaccatga atcaaactgc cattctgatt tgctgcctta tctttctgac tctaagtggc

121 attcaaggag tacctctctc tagaactgta cgctgtacct gcatcagcat tagtaatcaa

181 cctgttaatc caaggtcttt agaaaaactt gaaattattc ctgcaagcca attttgtcca

241 cgtgttgaga tcattgctac aatgaaaaag aagggtgaga agagatgtct gaatccagaa

301 tcgaaggcca tcaagaattt actgaaagca gttagcaagg aaaggtctaa aagatctcct

361 taaaaccaga ggggagcaaa atcgatgcag tgcttccaag gatggaccac acagaggctg
```

-continued

```
 421 cctctcccat cacttcccta catggagtat atgtcaagcc ataattgttc ttagtttgca

 481 gttacactaa aaggtgacca atgatggtca ccaaatcagc tgctactact cctgtaggaa

 541 ggttaatgtt catcatccta agctattcag taataactct accctggcac tataatgtaa

 601 gctctactga ggtgctatgt tcttagtgga tgttctgacc ctgcttcaaa tatttccctc

 661 acctttccca tcttccaagg gtactaagga atctttctgc tttggggttt atcagaattc

 721 tcagaatctc aaataactaa aaggtatgca atcaaatctg ctttttaaag aatgctcttt

 781 acttcatgga cttccactgc catcctccca aggggcccaa attctttcag tggctaccta

 841 catacaattc caaacacata caggaaggta gaaatatctg aaaatgtatg tgtaagtatt

 901 cttatttaat gaaagactgt acaaagtaga agtcttagat gtatatattt cctatattgt

 961 tttcagtgta catggaataa catgtaatta agtactatgt atcaatgagt aacaggaaaa

1021 ttttaaaaat acagatagat atatgctctg catgttacat aagataaatg tgctgaatgg

1081 ttttcaaaat aaaaatgagg tactctcctg gaaatattaa gaaagactat ctaaatgttg

1141 aaagatcaaa aggttaataa agtaattata actaa
```

Exemplary landmark residues, domains, and fragments of CXCL1 include, but are not limited to residues 67-129 (signal peptide), residues 130-360 (mature peptide), or residues 67-363 (coding region).

The human amino acid sequence of CXCL9 is provided below and is incorporated herein by reference (NCBI GenBank NP_002407.1 or UniProt Q07325):

```
                                                          (SEQ ID NO: 518)
  1  mkksqvlfll giillvligv qqgtpvvrkgr cscistnqgt ihlqslkdlk qfapspscek

 61  ieiiatlkng vqtclnpdsa dvkelikkwe kqvsqkkkqk ngkkhqkkkv lkvrksqrsr

121  qkktt
```

Exemplary landmark residues, domains, and fragments of CXCL9 include, but are not limited to residues 1-22 (signal peptide) or residues 23-125 (mature peptide). A fragment (e.g., a peptide or an epitope) of a CXCL9 protein is less than the length of the full length protein, e.g., a fragment is at least 3, 4, 5, 6, 7, 8, 9, 10, 20, 30, 40, 50, 100 or more residues in length, but less than e.g., 125 residues in the case of CXCL9 above.

The human CXCL9 nucleic acid sequence is provided below and is incorporated herein by reference (start and stop codons are underlined; NCBI GenBank: NM_002416.3).

```
                                                            SEQ ID NO: 519
  1 aaagaatttc tcaggctcaa aatccaatac aggagtgact tggaactcca ttctatcact

 61 atgaagaaaa gtggtgttct tttcctcttg ggcatcatct tgctggttct gattggagtg

121 caaggaaccc cagtagtgag aaagggtcgc tgttcctgca tcagcaccaa ccaagggact

181 atccacctac aatccttgaa agaccttaaa caatttgccc caagcccttc ctgcgagaaa

241 attgaaatca ttgctacact gaagaatgga gttcaaacat gtctaaaccc agattcagca

301 gatgtgaagg aactgattaa aaagtgggag aaacaggtca gccaaaagaa aaagcaaaag

361 aatgggaaaa aacatcaaaa aaagaaagtt ctgaaagttc gaaaatctca acgttctcgt

421 caaaagaaga ctacataaga gaccacttca ccaataagta ttctgtgtta aaaatgttct

481 attttaatta taccgctatc attccaaagg aggatggcat ataatacaaa ggcttattaa

541 tttgactaga aaatttaaaa cattactctg aaattgtaac taaagttaga aagttgattt
```

-continued

```
 601 taagaatcca aacgttaaga attgttaaag gctatgattg tctttgttct tctaccaccc
 661 accagttgaa tttcatcatg cttaaggcca tgattttagc aatacccatg tctacacaga
 721 tgttcaccca accacatccc actcacaaca gctgcctgga agagcagccc taggcttcca
 781 cgtactgcag cctccagaga gtatctgagg cacatgtcag caagtcctaa gcctgttagc
 841 atgctggtga gccaagcagt ttgaaattga gctggacctc accaagctgc tgtggccatc
 901 aacctctgta tttgaatcag cctacaggcc tcacacacaa tgtgtctgag agattcatgc
 961 tgattgttat tgggtatcac cactggagat caccagtgtg tggctttcag agcctccttt
1021 ctggctttgg aagccatgtg attccatctt gcccgctcag gctgaccact ttatttcttt
1081 ttgttcccct ttgcttcatt caagtcagct cttctccatc ctaccacaat gcagtgcctt
1141 tcttctctcc agtgcacctg tcatatgctc tgatttatct gagtcaactc ctttctcatc
1201 ttgtccccaa caccccacag aagtgctttc ttctcccaat tcatcctcac tcagtccagc
1261 ttagttcaag tcctgcctct taaataaacc tttttggaca cacaaattat cttaaaactc
1321 ctgtttcact tggttcagta ccacatgggt gaacactcaa tggttaacta attcttgggt
1381 gtttatccta tctctccaac cagattgtca gctccttgag ggcaagagcc acagtatatt
1441 tccctgtttc ttccacagtg cctaataata ctgtggaact aggttttaat aattttttaa
1501 ttgatgttgt tatgggcagg atggcaacca gaccattgtc tcagagcagg tgctggctct
1561 ttcctggcta ctccatgttg gctagcctct ggtaacctct tacttattat cttcaggaca
1621 ctcactacag ggaccaggga tgatgcaaca tccttgtctt tttatgacag gatgtttgct
1681 cagcttctcc aacaataaga agcacgtggt aaaacacttg cggatattct ggactgtttt
1741 taaaaaatat acagtttacc gaaaatcata taatcttaca atgaaaagga ctttatagat
1801 cagccagtga ccaacctttt cccaaccata caaaaattcc ttttcccgaa ggaaaagggc
1861 tttctcaata agcctcagct ttctaagatc taacaagata gccaccgaga tccttatcga
1921 aactcatttt aggcaaatat gagttttatt gtccgtttac ttgtttcaga gtttgtattg
1981 tgattatcaa ttaccacacc atctcccatg aagaaaggga acggtgaagt actaagcgct
2041 agaggaagca gccaagtcgg ttagtggaag catgattggt gcccagttag cctctgcagg
2101 atgtggaaac ctccttccag gggaggttca gtgaattgtg taggagaggt tgtctgtggc
2161 cagaatttaa acctatactc actttcccaa attgaatcac tgctcacact gctgatgatt
2221 tagagtgctg tccggtggag atcccacccg aacgtcttat ctaatcatga aactccctag
2281 ttccttcatg taacttccct gaaaaatcta agtgtttcat aaatttgaga gtctgtgacc
2341 cacttacctt gcatctcaca ggtagacagt atataactaa caaccaaaga ctacatattg
2401 tcactgacac acacgttata atcatttatc atatatatac atacatgcat acactctcaa
2461 agcaaataat ttttcacttc aaaacagtat tgacttgtat accttgtaat ttgaaatatt
2521 ttctttgtta aaatagaatg gtatcaataa atagaccatt aatcagaaaa cagatcttga
2581 tttttttttct cttgaatgta cccttcaact gttgaatgtt taatagtaaa tcttatatgt
2641 ccttatttac tttttagctt tctctcaaat aaagtgtaac actagttgag ataacacatg
2701 aaagctcttt aaagggtcga tcgggaacag gaaaaaaaac ctatggaaaa tatgacaaca
2761 c
```

Exemplary landmark residues, domains, and fragments of CXCL9 include, but are not limited to residues 61-126 (signal peptide) or residues 127-435 (mature peptide).

The human amino acid sequence of CXCL11 is provided below and is incorporated herein by reference (NCBI GenBank NP_005400.1 or UniProt 014625):

(SEQ ID NO: 520)
1 msvkgmaial avilcatvvq gfpmfkrgrc lcigpgvkav kvadiekasi mypsnncdki 61 eviitlkenk gqrclnpksk qarliikkve rknf Exemplary landmark residues, domains, and fragments of CXCL11 include, but are not limited to residues 1-21 (signal peptide), residues 22-94 (mature peptide), or residues 28-90 (chemokine-CXC domain). A fragment (e.g., a peptide or an epitope) of a CXCL11 protein is less than the length of the full length protein, e.g., a fragment is at least 3, 4, 5, 6, 7, 8, 9, 10, 20, 30, 40, 50, 75 or more residues in length, but less than e.g., 94 residues in the case of CXCL11 above.

The human CXCL11 nucleic acid sequence is provided below and is incorporated herein by reference (start and stop codons are underlined; NCBI GenBank: NM_005409.5).

SEQ ID NO: 521
1 gttcagcatt tctactcctt ccaagaagag cagcaaagct gaagtagcag cagcagcacc 61 agcagcaaca gcaaaaaaca aacatgagtg tgaagggcat ggctatagcc ttggctgtga 121 tattgtgtgc tacagttgtt caaggcttcc ccatgttcaa aagaggacgc tgtctttgca 181 taggccctgg ggtaaaagca gtgaaagtgg cagatattga gaaagcctcc ataatgtacc 241 caagtaacaa ctgtgacaaa atagaagtga ttattaccct gaaagaaaat aaaggacaac 301 gatgcctaaa tcccaaatcg aagcaagcaa ggcttataat caaaaaagtt gaaagaaaga 361 atttttaaaa atatcaaaac atatgaagtc ctggaaaaga gcatctgaaa aacctagaac 421 aagtttaact gtgactactg aaatgacaag aattctacag taggaaactg agacttttct 481 atggttttgt gactttcaac ttttgtacag ttatgtgaag gatgaaaggt gggtgaaagg 541 accaaaaaca gaaatacagt cttcctgaat gaatgacaat cagaattcca ctgcccaaag 601 gagtccaaca attaaatgga tttctaggaa aagctacctt aagaaaggct ggttaccatc 661 ggagtttaca aagtgctttc acgttcttac ttgttgcatt atacattcat gcatttctag 721 gctagagaac cttctagatt tgatgcttac aactattctg ttgtgactat gagaacattt 781 ctgtctctag aagtcatctg tctgtattga tctttatgct atattactat ctgtggttac 841 ggtggagaca ttgacattat tactggagtc aagcccttat aagtcaaaag catctatgtg 901 tcgtaaaaca ttcctcaaac atttttttcat gcaaatacac acttctttcc ccaaacatca 961 tgtagcacat caatatgtag ggagacattc ttatgcatca tttggtttgt tttataacca 1021 attcattaaa tgtaattcat aaaatgtact atgaaaaaaa ttatacgcta tgggatactg 1081 gcaaaagtgc acatatttca taaccaaatt agtagcacca gtcttaattt gatgtttttc 1141 aacttttatt cattgagatg ttttgaagca attaggatat gtgtgtttac tgtacttttt 1201 gttttgatcc gtttgtataa atgatagcaa tatcttggac acatctgaaa tacaaaatgt 1261 ttttgtctac caaagaaaaa tgttgaaaaa taagcaaatg tatacctagc aatcactttt 1321 actttttgta attctgtctc ttagaaaaat acataatcta atcaatttct ttgttcatgc 1381 ctatatactg taaaatttag gtatactcaa gactagttta aagaatcaaa gtcatttttt 1441 tctctaataa actaccacaa cctttctttt ttaaaaaaa Exemplary landmark residues, domains, and fragments of CXCL11 include, but are not limited to residues 84-146 (signal peptide), or residues 147-365 (mature peptide).

The human amino acid sequence of tumor necrosis factor (TNF) is provided below and is incorporated herein by reference (NCBI GenBank NP_000585.2 or (UniProt P01375):

(SEQ ID NO: 522)

```
  1 mstesmirdv elaeealpkk tggpqgsrrc lflslfsfli vagattlfcl lhfgvigpqr

 61 eefprdlsli splaqavrss srtpsdkpva hvvanpqaeg qlqwlnrran allangvelr

121 dnqlvvpseg lyliysqvlf kgqgcpsthv lithtisria vsyqtkvnll saikspcqre

181 tpegaeakpw yepiylggvf qlekgdrlsa einrpdyldf aesgqvyfgi ial
```

Exemplary landmark residues, domains, and fragments of TNF include, but are not limited to residues 1-35 (cytoplasmic domain), residues 36-56 (helical transmembrane domain) and residues 57-233 (extracellular domain). A fragment (e.g., a peptide or an epitope) of a TNF protein is less than the length of the full length protein, e.g., a fragment is at least 3, 4, 5, 6, 7, 8, 9, 10, 20, 30, 40, 50, 100, 200 or more residues in length, but less than e.g., 233 residues in the case of TNF above.

The human TNF nucleic acid sequence is provided below and is incorporated herein by reference (start and stop codons are underlined; NCBI GenBank: NM_000594.4).

SEQ ID NO: 523

```
   1 agcagacgct ccctcagcaa ggacagcaga ggaccagcta agagggagag aagcaactac

  61 agaccccccc tgaaaacaac cctcagacgc cacatcccct gacaagctgc caggcaggtt

 121 ctcttcctct cacatactga cccacggctc caccctctct cccctggaaa ggacaccatg

 181 agcactgaaa gcatgatccg ggacgtggag ctggccgagg aggcgctccc caagaagaca

 241 ggggggcccc agggctccag gcggtgcttg ttcctcagcc tcttctcctt cctgatcgtg

 301 gcaggcgcca ccacgctctt ctgcctgctg cactttggag tgatcggccc ccagagggaa

 361 gagttcccca gggacctctc tctaatcagc cctctggccc aggcagtcag atcatcttct

 421 cgaaccccga gtgacaagcc tgtagcccat gttgtagcaa accctcaagc tgaggggcag

 481 ctccagtggc tgaaccgccg ggccaatgcc ctcctggcca atggcgtgga gctgagagat

 541 aaccagctgg tggtgccatc agagggcctg tacctcatct actcccaggt cctcttcaag

 601 ggccaaggct gcccctccac ccatgtgctc ctcacccaca ccatcagccg catcgccgtc

 661 tcctaccaga ccaaggtcaa cctcctctct gccatcaaga gcccctgcca gagggagacc

 721 ccagaggggg ctgaggccaa gccctggtat gagcccatct atctgggagg ggtcttccag

 781 ctggagaagg gtgaccgact cagcgctgag atcaatcggc ccgactatct cgactttgcc

 841 gagtctgggc aggtctactt tgggatcatt gccctgtgag gaggacgaac atccaacctt

 901 cccaaacgcc tcccctgccc caatcccttt attacccccct ccttcagaca ccctcaacct

 961 cttctggctc aaaaagagaa ttgggggctt agggtcggaa cccaagctta gaactttaag

1021 caacaagacc accacttcga aacctgggat tcaggaatgt gtggcctgca cagtgaagtg

1081 ctggcaacca ctaagaattc aaactggggc ctccagaact cactggggcc tacagctttg

1141 atccctgaca tctggaatct ggagaccagg gagcctttgg ttctggccag aatgctgcag

1201 gacttgagaa gacctcacct agaaattgac acaagtggac cttaggcctt cctctctcca

1261 gatgtttcca gacttccttg agacacggag cccagccctc cccatggagc cagctccctc

1321 tatttatgtt tgcacttgtg attatttatt atttatttat tatttattta tttacagatg

1381 aatgtattta tttgggagac cggggtatcc tgggggaccc aatgtaggag ctgccttggc

1441 tcagacatgt tttccgtgaa aacggagctg aacaataggc tgttcccatg tagcccctg

1501 gcctctgtgc cttcttttga ttatgttttt taaaatattt atctgattaa gttgtctaaa

1561 caatgctgat ttggtgacca actgtcactc attgctgagc ctctgctccc caggggagtt

1621 gtgtctgtaa tcgccctact attcagtggc gagaaataaa gtttgcttag aaaagaaa
```

Exemplary landmark residues, domains, and fragments of TNF include, but are not limited to residues 280-285 (TNF domain), or residues 458-1678 (exon).

The human amino acid sequence of IL-2 is provided below and is incorporated herein by reference (NCBI GenBank NP_000577.1 or UniProt P60568)

```
                                                   (SEQ ID NO: 487)
  1  myrmqllsci alslalvtns aptssstkkt qlqlehllld lqmilnginn yknpkltrml

 61  tfkfympkka telkhlqcle eelkpleevl nlaqsknfhl rprdlisnin vivlelkgse

121  ttfmceyade tativeflnr witfcqsiis tlt
```

Exemplary landmark residues, domains, and fragments of IL-2 include, but are not limited to residues 1-20 (signal peptide), residues 21-153 (mature peptide), or residue 23 (glycosylation site). A fragment (e.g., a peptide or an epitope) of a IL-2 protein is less than the length of the full length protein, e.g., a fragment is at least 3, 4, 5, 6, 7, 8, 9, 10, 20, 30, 40, 50, 100, 153 or more residues in length, but less than e.g., 153 residues in the case of IL-2 above.

The human IL-2 nucleic acid sequence is provided below and is incorporated herein by reference (start and stop codons are underlined; NCBI GenBank: NM_000586.4 (SEQ ID NO: 488).

```
                                                   (SEQ ID NO: 488)
   1 ctatcaccta agtgtgggct aatgtaacaa agagggattt cacctacatc cattcagtca

  61 gtctttgggg gtttaaagaa attccaaaga gtcatcagaa gaggaaaaat gaaggtaatg

 121 ttttttcaga caggtaaagt ctttgaaaat atgtgtaata tgtaaaacat tttgacaccc

 181 ccataatatt tttccagaat taacagtata aattgcatct cttgttcaag agttccctat

 241 cactctcttt aatcactact cacagtaacc tcaactcctg ccacaatgta caggatgcaa

 301 ctcctgtctt gcattgcact aagtcttgca cttgtcacaa acagtgcacc tacttcaagt

 361 tctacaaaga aaacacagct acaactggag catttactgc tggatttaca gatgattttg

 421 aatggaatta ataattacaa gaatcccaaa ctcaccagga tgctcacatt taagttttac

 481 atgcccaaga aggccacaga actgaaacat cttcagtgtc tagaagaaga actcaaacct

 541 ctggaggaag tgctaaattt agctcaaagc aaaaactttc acttaagacc cagggactta

 601 atcagcaata tcaacgtaat agttctggaa ctaaagggat ctgaaacaac attcatgtgt

 661 gaatatgctg atgagacagc aaccattgta gaatttctga acagatggat taccttttgt

 721 caaagcatca tctcaacact gacttgataa ttaagtgctt cccacttaaa acatatcagg

 781 ccttctattt atttaaatat ttaaatttta tatttattgt tgaatgtatg gtttgctacc

 841 tattgtaact attattctta atcttaaaac tataaatatg gatcttttat gattcttttt

 901 gtaagcccta ggggctctaa aatggtttca cttatttatc ccaaaatatt tattattatg

 961 ttgaatgtta aatatagtat ctatgtagat tggttagtaa aactatttaa taaatttgat

1021 aaatataaa.
```

Exemplary landmark residues, domains, and fragments of IL-2 include, but are not limited to residues 286-345 (signal peptide), residues 346-744 (mature peptide), or 286-747 (coding region).

The human amino acid sequence of IL-6 is provided below and is incorporated herein by reference (NCBI GenBank NP_000591.1 or UniProt P05231).

(SEQ ID NO: 489)

```
  1 mnsfstsafg pvafslglll vlpaafpapv ppgedskdva aphrqpltss eridkqiryi

 61 ldgisalrke tcnksnmces skealaennl nlpkmaekdg cfqsgfneet clvkiitgll

121 efevyleylq nrfesseeqa ravqmstkvl iqflqkkakn ldaittpdpt tnaslltklq

181 aqnqwlqdmt thlilrsfke flqsslralr qm
```

Exemplary landmark residues, domains, and fragments of IL-6 include, but are not limited to residues 1-29 (signal peptide), residues 30-212 (mature peptide), or residue 73 (glycosylation site). A fragment (e.g., a peptide or an epitope) of a IL-6 protein is less than the length of the full length protein, e.g., a fragment is at least 3, 4, 5, 6, 7, 8, 9, 10, 20, 30, 40, 50, 100, 200 or more residues in length, but less than e.g., 212 residues in the case of IL-6 above.

The human IL-6 nucleic acid sequence is provided below and is incorporated herein by reference (start and stop codons are underlined; NCBI GenBank: NM_000600.5).

(SEQ ID NO: 490)

```
   1 attctgccct cgagcccacc gggaacgaaa gagaagctct atctcccctc caggagccca

  61 gctatgaact ccttctccac aagcgccttc ggtccagttg ccttctccct ggggctgctc

 121 ctggtgttgc ctgctgcctt ccctgcccca gtacccccag gagaagattc caaagatgta

 181 gccgccccac acagacagcc actcacctct tcagaacgaa ttgacaaaca aattcggtac

 241 atcctcgacg gcatctcagc cctgagaaag gagacatgta acaagagtaa catgtgtgaa

 301 agcagcaaag aggcactggc agaaaacaac ctgaaccttc caaagatggc tgaaaaagat

 361 ggatgcttcc aatctggatt caatgaggag acttgcctgg tgaaaatcat cactggtctt

 421 ttggagtttg aggtatacct agagtacctc cagaacagat ttgagagtag tgaggaacaa

 481 gccagagctg tgcagatgag tacaaaagtc ctgatccagt tcctgcagaa aaaggcaaag

 541 aatctagatg caataaccac ccctgaccca accacaaatg ccagcctgct gacgaagctg

 601 caggcacaga accagtggct gcaggacatg acaactcatc tcattctgcg cagctttaag

 661 gagttcctgc agtccagcct gagggctctt cggcaaatgt agcatgggca cctcagattg

 721 ttgttgttaa tgggcattcc ttcttctggt cagaaacctg tccactgggc acagaactta

 781 tgttgttctc tatggagaac taaaagtatg agcgttagga cactatttta attattttta

 841 atttattaat atttaaatat gtgaagctga gttaatttat gtaagtcata tttatatttt

 901 taagaagtac cacttgaaac attttatgta ttagttttga aataataatg gaaagtggct

 961 atgcagtttg aatatccttt gtttcagagc cagatcattt cttggaaagt gtaggcttac

1021 ctcaaataaa tggctaactt atacatattt ttaaagaaat atttatattg tatttatata

1081 atgtataaat ggtttttata ccaataaatg gcattttaaa aaattca
```

Exemplary landmark residues, domains, and fragments of IL-6 include, but are not limited to residues 64-150 (signal peptide), residues 151-699 (mature peptide), or 64-702 (coding region).

The human amino acid sequence of IL-7 is provided below and is incorporated herein by reference (NCBI GenBank NP_000871.1 or UniProt P13232)

(SEQ ID NO: 491)

```
  1 mfhvsfryif glpplilvll pvassdcdie gkdgkqyesv lmvsidqlld smkeigsncl

 61 nnefnffkrh icdankegmf lfraarklrq flkmnstgdf dlhllkvseg ttillnctgq

121 vkgrkpaalg eaqptkslee nkslkeqkkl ndlcflkrll qeiktcwnki lmgtkeh
```

Exemplary landmark residues, domains, and fragments of IL-7 include, but are not limited to residues 1-25 (signal peptide), residues 26-177 (mature peptide), or residue 95 (glycosylation site). A fragment (e.g., a peptide or an epitope) of a IL-7 protein is less than the length of the full length protein, e.g., a fragment is at least 3, 4, 5, 6, 7, 8, 9, 10, 20, 30, 40, 50, 100, 150 or more residues in length, but less than e.g., 177 residues in the case of IL-7 above.

The human IL-7 nucleic acid sequence is provided below and is incorporated herein by reference (start and stop codons are underlined: NCHI GenBank: NM_000880.4)

```
                                                      (SEQ ID NO: 492)
   1 acacttgtgg cttccgtgca cacattaaca actcatggtt ctagctccca gtcgccaagc

  61 gttgccaagg cgttgagaga tcatctggga agtcttttac ccagaattgc tttgattcag

 121 gccagctggt ttttcctgcg gtgattcgga aattcgcgaa ttcctctggt cctcatccag

 181 gtgcgcggga agcaggtgcc caggagagag gggataatga agattccatg ctgatgatcc

 241 caaagattga acctgcagac caagcgcaaa gtagaaactg aaagtacact gctggcggat

 301 cctacggaag ttatggaaaa ggcaaagcgc agagccacgc cgtagtgtgt gccgcccccc

 361 ttgggatgga tgaaactgca gtcgcggcgt gggtaagagg aaccagctgc agagatcacc

 421 ctgcccaaca cagactcggc aactccgcgg aagaccaggg tcctgggagt gactatgggc

 481 ggtgagagct tgctcctgct ccagttgcgg tcatcatgac tacgcccgcc tcccgcagac

 541 catgttccat gtttctttta ggtatatctt tggacttcct cccctgatcc ttgttctgtt

 601 gccagtagca tcatctgatt gtgatattga aggtaaagat ggcaaacaat atgagagtgt

 661 tctaatggtc agcatcgatc aattattgga cagcatgaaa gaaattggta gcaattgcct

 721 gaataatgaa tttaactttt ttaaaagaca tatctgtgat gctaataagg aaggtatgtt

 781 tttattccgt gctgctcgca agttgaggca atttcttaaa atgaatagca ctggtgattt

 841 tgatctccac ttattaaaag tttcagaagg cacaacaata ctgttgaact gcactggcca

 901 ggttaaagga agaaaaccag ctgccctggg tgaagcccaa ccaacaaaga gtttggaaga

 961 aaataaatct ttaaaggaac agaaaaaact gaatgacttg tgtttcctaa agagactatt

1021 acaagagata aaaacttgtt ggaataaaat tttgatgggc actaaagaac actgaaaaat

1081 atggagtggc aatatagaaa cacgaacttt agctgcatcc tccaagaatc tatctgctta

1141 tgcagttttt cagagtggaa tgcttcctag aagttactga atgcaccatg gtcaaaacgg

1201 attagggcat ttgagaaatg catattgtat tactagaaga tgaatacaaa caatggaaac

1261 tgaatgctcc agtcaacaaa ctatttctta tatatgtgaa catttatcaa tcagtataat

1321 tctgtactga tttttgtaag acaatccatg taaggtatca gttgcaataa tacttctcaa

1381 acctgtttaa atatttcaag acattaaatc tatgaagtat ataatggttt caaagattca

1441 aaattgacat tgctttactg tcaaaataat tttatggctc actatgaatc tattatactg

1501 tattaagagt gaaaattgtc ttcttctgtg ctggagatgt tttagagtta acaatgatat

1561 atggataatg ccggtgagaa taagagagtc ataaacctta agtaagcaac agcataacaa

1621 ggtccaagat acctaaaaga gatttcaaga gatttaatta atcatgaatg tgtaacacag

1681 tgccttcaat aaatggtata gcaaatgttt tgacatgaaa aaaggacaat ttcaaaaaaa

1741 taaaataaaa taaaaataaa ttcacctagt ctaaggatgc taaaccttag tactgagtta

1801 cattgtcatt tatatagatt ataacttgtc taaataagtt tgcaatttgg gagatatatt

1861 tttaagataa taatatatgt ttacctttta attaatgaaa tatctgtatt taattttgac

1921 actatatctg tatataaaat attttcatac agcattacaa attgcttact ttggaataca

1981 tttctccttt gataaaataa atgagctatg tattaa.
```

Exemplary landmark residues, domains, and fragments of IL-7 include, but are not limited to residues 542-616 (signal peptide), residues 617-1072 (mature peptide), or 542-1075 (coding region).

The human amino acid sequence of IL-12 alpha subunit is provided below and is incorporated herein by reference (UniProt P29459).

```
                                               (SEQ ID NO: 493)
  1  mcparsllly atlvlldhls larnlpvatp dpgmfpclhh sqnllravsn mlqkarqtle

 61  fypctseeid heditkdkts tveaclplel tknesclnsr etsfitngsc lasrktsfmm

121  alclssiyed lkmyqvefkt mnakllmdpk rqifldqnml avidelmqal nfnsetvpqk

181  ssleepdfyk tkiklcillh afriravtid rvmsylnas
```

Exemplary landmark residues, domains, and fragments of L-12 alpha subunit include, but are not limited to residues 1-22 (signal peptide) or residues 23-219 (mature peptide). A fragment (e.g., a peptide or an epitope) of a IL-12 protein is less than the length of the full length protein, e.g., a fragment is at least 3, 4, 5, 6, 7, 8, 9, 10, 20, 30, 40, 50, 100, 200 or more residues in length, but less than e.g., 219 residues in the case of IL-12 above.

The human IL-12 sununit alpha nucleic acid sequence is provided below and is incorporated herein by reference (start and stop codons are underlined; NCBI GenBank: AF101062.1).

```
                                               (SEQ ID NO: 494)
  1  atgtggcccc ctgggtcagc ctcccagcca ccgccctcac ctgccgcggc cacaggtctg

 61  catccagcgg ctcgccctgt gtccctgcag tgccggctca gcatgtgtcc agcgcgcagc

121  ctcctccttg tggctaccct ggtcctcctg gaccacctca gtttggccag aaacctcccc

181  gtggccactc cagacccagg aatgttccca tgccttcacc actcccaaaa cctgctgagg

241  gccgtcagca acatgctcca gaaggccaga caaactctag aattttaccc ttgcacttct

301  gaagagattg atcatgaaga tatcacaaaa gataaaacca gcacagtgga ggcctgttta

361  ccattggaat taaccaagaa tgagagttgc ctaaattcca gagagacctc tttcataact

421  aatgggagtt gcctggcctc cagaaagacc tcttttatga tggccctgtg ccttagtagt

481  atttatgaag acttgaagat gtaccaggtg gagttcaaga ccatgaatgc aaagcttctg

541  atggatccta agaggcagat ctttctagat caaaacatgc tggcagttat tgatgagctg

601  atgcaggccc tgaatttcaa cagtgagact gtgccacaaa aatcctccct tgaagaaccg

661  gatttttata aaactaaaat caagctctgc atacttcttc atgctttcag aattcgggca

721  gtgactattg atagagtgat gagctatctg aatgcttcct aa
```

Exemplary landmark residues, domains, and fragments of IL-12 alpha subunit include, but are not limited to residues 1-762 (coding region), or residues 1-203 (interleukin binding region).

The human amino acid sequence of IL-12 beta subunit is provided below and is incorporated herein by reference (UniProt P29460).

```
                                               (SEQ ID NO: 524)
  1  mchgqlvisw fslvflaspl vaiwelkkdv yvveldwypd apgemvvltc dtpeedgitw

 61  tldqssevlg sqktltiqvk efgdagqytc hkggevlshs llllhkkedg iwstdilkdq

121  kepknktflr ceaknysgrf tcwwlttist dltfsvkssr gssdpqgvtc gaatlsaerv
```

-continued 181 rgdnkeyeys vecqedsacp aaeeslpiev mvdavhklky enytssffir diikpdppkn 241 lqlkplknsr qvevsweypd twstphsyfs ltfcvqvqgk skrekkdrvf tdktsatvic 301 rknasisvra qdryysssws ewasvpcs Exemplary landmark residues, domains, and fragments of IL-12 beta subunit include, but are not limited to residues 1-22 (signal peptide) or residues 23-328 (mature peptide). A fragment (e.g., a peptide or an epitope) of a IL-12 beta subunit protein is less than the length of the full length protein, e.g., a fragment is at least 3, 4, 5, 6, 7, 8, 9, 10, 20, 30, 40, 50, 100, 200 or more residues in length, but less than e.g., 328 residues in the case of IL-12 beta subunit above.

The human IL-12 subunit beta nucleic acid sequence is provided below and is incorporated herein by reference (stop and start codons are bold and underlined NM_002187.3).

SEQ ID NO: 525

1 agaagaaaca acatctgttt cagggccatt ggactctccg tcctgcccag agcaagatgt 61 gtcaccagca gttggtcatc tcttggtttt ccctggtttt tctggcatct cccctcgtgg 121 ccatatggga actgaagaaa gatgtttatg tcgtagaatt ggattggtat ccggatgccc 181 ctggagaaat ggtggtcctc acctgtgaca cccctgaaga agatggtatc acctggacct 241 tggaccagag cagtgaggtc ttaggctctg gcaaaaccct gaccatccaa gtcaaagagt 301 ttggagatgc tggccagtac acctgtcaca aaggaggcga ggttctaagc cattcgctcc 361 tgctgcttca caaaaaggaa gatggaattt ggtccactga tattttaaag gaccagaaag 421 aacccaaaaa taagaccttt ctaagatgcg aggccaagaa ttattctgga cgtttcacct 481 gctggtggct gacgacaatc agtactgatt tgacattcag tgtcaaaagc agcagaggct 541 cttctgaccc ccaaggggtg acgtgcggag ctgctacact ctctgcagag agagtcagag 601 gggacaacaa ggagtatgag tactcagtgg agtgccagga ggacagtgcc tgcccagctg 661 ctgaggagag tctgcccatt gaggtcatgg tggatgccgt tcacaagctc aagtatgaaa 721 actacaccag cagcttcttc atcagggaca tcatcaaacc tgacccaccc aagaacttgc 781 agctgaagcc attaaagaat tctcggcagg tggaggtcag ctgggagtac cctgacacct 841 ggagtactcc acattcctac ttctccctga cattctgcgt tcaggtccag ggcaagagca 901 agagagaaaa gaaagataga gtcttcacgg acaagacctc agccacggtc atctgccgca 961 aaaatgccag cattagcgtg cgggcccagg accgctacta tagctcatct tggagcgaat 1021 gggcatctgt gccctgcagt taggttctga tccaggatga aaatttggag gaaaagtgga 1081 agatattaag caaaatgttt aaagacacaa cggaatagac ccaaaaagat aatttctatc 1141 tgatttgctt taaaacgttt ttttaggatc acaatgatat ctttgctgta tttgtatagt 1201 tagatgctaa atgctcattg aaacaatcag ctaatttatg tatagatttt ccagctctca 1261 agttgccatg ggccttcatg ctatttaaat atttaagtaa tttatgtatt tattagtata 1321 ttactgttat ttaacgtttg tctgccagga tgtatggaat gtttcatact cttatgacct 1381 gatccatcag gatcagtccc tattatgcaa aatgtgaatt taattttatt tgtactgaca 1441 acttttcaag caaggctgca agtacatcag ttttatgaca atcaggaaga atgcagtgtt 1501 ctgataccag tgccatcata cacttgtgat ggatgggaac gcaagagata cttacatgga 1561 aacctgacaa tgcaaacctg ttgagaagat ccaggagaac aagatgctag ttcccatgtc 1621 tgtgaagact tcctggagat ggtgttgata aagcaattta gggccactta cacttctaag 1681 caagtttaat ctttggatgc ctgaatttta aaagggctag aaaaaaatga ttgaccagcc 1741 tgggaaacat aacaagaccc cgtctctaca aaaaaaattt aaaattagcc aggcgtggtg 1801 gctcatgctt gtggtcccag ctgttcagga ggatgaggca ggaggatctc ttgagcccag -continued

```
1861 gaggtcaagg ctatggtgag ccgtgattgt gccactgcat accagcctag gtgacagaat

1921 gagaccctgt ctcaaaaaaa aaaatgattg aaattaaaat tcagctttag cttccatggc

1981 agtcctcacc cccacctctc taaaagacac aggaggatga cacagaaaca ccgtaagtgt

2041 ctggaaggca aaaagatctt aagattcaag agagaggaca agtagttatg gctaaggaca

2101 tgaaattgtc agaatggcag gtggcttctt aacagccctg tgagaagcag acagatgcaa

2161 agaaaatctg gaatcccttt ctcattagca tgaatgaacc tgatacacaa ttatgaccag

2221 aaaatatggc tccatgaagg tgctactttt aagtaatgta tgtgcgctct gtaaagtgat

2281 tacatttgtt tcctgtttgt ttatttattt atttattttt gcattctgag gctgaactaa

2341 taaaaactct tctttgtaat cata
```

Exemplary landmark residues, domains, and fragments of IL-12 beta subunit include, but are not limited to residues 57-122 (signal peptide), or residues 123-1040 (mature protein).

In other aspects of the invention, the methods described herein comprise administering a pHLIP® construct comprising an antibody recruiting molecule that is linked to one or more pHLIP® peptides. For example, the antibody recruiting molecule comprises an epitope, including for example a small molecule (alternatively, a "small molecule antigen"). For example, the small molecule epitope comprises a Di-nitrophenyl (DNP) group, or a derivative thereof. As used herein, the terms "DNP" and "2,4-DNP" interchangeably refer to 2,4-dinitrophenol, a salt, solvate or adduct thereof.

In examples, the small molecule epitope comprises 0-(2, 4-dinitrophenyl)hydroxylamine (structure provided below):

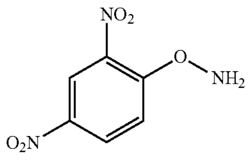 [SMILES: NOc1ccc([N+](=O)[O-])cc1[N+](=O)[O-]]

In embodiments, the composition of the present disclosure includes modified DNPs, such as those conjugated to polyethylene glycol may be used in the present disclosure. The DNP, DNP derivative, or salt in the composition of the present disclosure may have a molecular weight in the range from 200 Da to 1,000 Da or from 200 Da to 500 Da.

In some examples, the DNP derivative may be substituted, e.g., with an alkyl group, an alkylene group, a heteroalkyl group, a cycloalkyl group, an aryl group, or any combination thereof.

Also within the invention is a composition comprising an antibody or immune cell recruiting molecule linked to one or more pHLIP® peptides by a non-cleavable linker compound for eliciting an anti-tumor response in a subject. Also provided herein are methods for promoting an immune response. For example, the method comprises administering a composition comprises an epitope comprising at least 4 amino acids conjugated to a pHLIP® peptide. The pHLIP® peptide positions an epitope on the surface of the targeted cells in diseased tissue to induce an immune response predominantly in diseased tissue. For example, if the epitope is a peptide, it can be added as an extension of the non-inserting end of the pHLIP peptide. Furthermore, the epitope then interacts with endogenous or exogenous immune cells, endogenous antibodies and proteins, e.g., pre-existing antibodies and proteins in the subject's body, or exogenous antibodies administrated into body, or antibodies generated in the course of vaccination, which then induce an immune response. Also provided herein are methods for promoting delivery of cytotoxic payloads with ADCs to induce cell killing. Furthermore, the epitope interacts with ADCs administrated into body, which then induce cell killing.

Furthermore, provided herein are methods of treating a diseased tissue with a naturally acidic extracellular environment or a tissue with an artificially induced acidic extracellular environment relative to normal physiological pH in a subject. For example, the diseased tissue includes a cancerous tissue or a tumor. As described above, the composition recruits the subject's immune cells, endogenous antibodies and proteins to induce an immune response, and thereby treats the diseased tissue in the subject. The immune response can include, for example, initiation of complement-dependent cytotoxicity (CDC), antibody-dependent cell-mediated cytotoxicity (ADCC), or the release of cytokines or inflammatory mediators to promote T-cell or NK-cell responses. The immune response can include, for example, homing of T-cells and NK-cells and their activation. Also as described above, the composition promotes binding of antibody-drug conjugates to the cells in targeted tissue, and thus promotes cell killing.

Also within the invention is a method of augmenting (increasing) an immune response in a subject, comprising administering to the subject a composition comprising an epitope linked to a pHLIP® peptide as described above. In some examples, the composition is administered using methods well known in the art, e.g., the composition is injected directly into a tumor mass. Alternatively, the composition is systemically administered.

Formulations provided herein may include an Epitope-Linker-Peptide, where "Peptide" is a pHLIP® peptide. The formulation may be suitable for intravenous, subcutaneous, intraarterial, intraperitoneal, intracerebral, intracerebroventricular, intrathecal, intracardiac, intracavernous, intraosseous, intraocular, or intravitreal administration are also provided. In some examples, a formulation is used for intramuscular, intradermal, transdermal, transmucosal, intralesional, subcutaneous, topical, epicutaneous, extra-amniotic, intravaginal, intravesical, nasal, or oral administration. The present subject matter also includes a formulation for intravesical instillation. In some embodiments, the formulation is used for the treatment of cancer (e.g., solid tumors).

Also provided herein is a formulation comprising an Epitope-Linker-Peptide that comprises multiple pHLIP® peptides, e.g., for systemic administration. Also provided herein is a formulation comprising an Epitope-Linker-Peptide that comprises multiple epitopes, e.g., for systemic administration. In certain embodiments, the formulation is used for the treatment of cancer or diseases associated with inflammation.

Provided herein is a method of treating cancer or inflammation in a subject, comprising administering to the subject an effective amount of a pH-triggered compound (a pHLIP® peptide) linked to an epitope (a "pHLIP® construct"), which is then delivered by pHLIP® to the surface of the cell. For example, the cancer includes a solid tumor. Non-limiting examples of cancer include colon cancer, prostate cancer, breast cancer, bladder cancer, lung cancer, skin cancer, liver cancer, bone cancer, ovarian cancer, stomach cancer, pancreatic cancer, testicular cancer, and brain cancer.

Systemic or blood-borne tumor cells, e.g., cancers of the circulatory system, may also be treated using the pHLIP® peptide constructs.

The composition preferentially targets a diseased tissue compared to a healthy tissue, thereby minimizing damage to the healthy tissue. For example, the composition selectively promotes cell killing in the diseased tissue, e.g., the tumor cell.

Included herein are pharmaceutical compositions comprising a pH-triggered peptide linked to an epitope and a pharmaceutically acceptable carrier.

As used herein, "effective" when referring to an amount of a compound refers to the quantity of the compound that is sufficient to yield a desired response without undue adverse side effects (such as toxicity, irritation, or allergic response) commensurate with a reasonable benefit/risk ratio when used in the manner of this disclosure.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, a goat, or a pig. In preferred embodiments, the subject is a human.

In some examples, the exogenous cells or monoclonal antibody or antibody-drug conjugate is administered to the subject during or after administration of the epitope pHLIP® peptide construct. In some examples, the subject comprises endogenous, e.g., pre-existing, antibodies or immune cells to the epitope of the pHLIP® peptide construct. Alternatively, the subject does not comprise existing antibodies to the epitope delivered by the construct (at the time of initial administration). In such examples, a subject may be immunized with the epitope to generate an antibody response and then the subject is subsequently administered the pHLIP®-epitope construct. In such examples, the construct is administered after administration of the antigen epitope in a form that is not conjugated to a pHLIP®.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DETAILED DESCRIPTION

The invention features compositions and methods for decorating target cells (cancer cells) using epitope-pHLIP® compounds, such that the pHLIP® targets tumors by responding to cell surface acidity, inserting into cancer cell membranes, and locating (positioning) a specified epitope on the cell surface to induce cell killing.

Epitopes bind and/or attract exogenous immune cells (T-cells or NK-cells) or exogenously developed monoclonal antibodies or antibody-drug conjugates administrated into body during or after of epitope-pHLIP® compound administration, and selectively promote cell killing while sparing normal tissues. Among these epitopes include epitopes for developed monoclonal antibodies.

Epitopes bind and/or attract endogenous (natural) immune cells (lymphocytes) or endogenous antibodies already present in the blood, and selectively initiate a specific immune response to attack the tumor while sparing normal tissues. Among these epitopes are epitopes associated with the surfaces of animal cells and bacteria. In many cases, humans already have developed antibodies in blood stream, which recognize such epitopes. Epitopes delivered according to the methods described herein may also bind/attract endogenous antibodies, which are produced (generated) in the course of vaccination. The epitopes (any antigen molecule used for vaccination), is linked (conjugated) to a pHLIP® peptide and delivered to tumors to promote an immune reaction within target tissue, e.g., by using harnessing influenza vaccines that create antibodies to virus surface epitopes. In some examples, an individual is immunized using a chosen antigen, followed by targeting the antigen targeted to tumor cells by a pHLIP® peptide.

Decorated Acidic Diseased Cells

Acidic diseased cells, e.g., cancer cells are targeted using epitope-pHLIP® peptide compositions, such that the pHLIP® peptide targets tumors by responding to cell surface acidity, inserting into cancer cell membranes, and locating/positioning a specific epitope on the cell surface to induce and promote cellular responses including immune stimulation and inhibition of cell proliferation. The immune stimulation leads to cytotoxicity and death of the acidic disease cell.

Epitope-pHLIP® Peptide Compositions

Representations of exemplary pHLIP® compositions for therapeutic use are shown in FIGS. 1-4. The compositions comprise a pHLIP® peptide (or pHLIP® conjugate, where the pHLIP® peptide is linked to an epitope for delivery/positioning on the surface of diseased cells). pHLIP® peptides are described here and in U.S. Pat. Nos. 9,814,781 and 9,289,508 (hereby incorporated by reference) as well as U.S. Patent Publication 20180117183, 20180064648, 20180221500, 20180117183, 20180064648, 20160256560, 20150191508, 20150051153, and 20120142042, 20120039990, 20080233107, as well as PCT Application No. PCT/US2017/023458 (cyclic pHLIP® peptides), each of which is hereby incorporated by reference.

Figure 1:
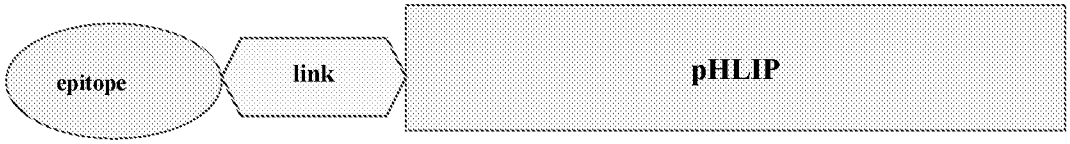
FIG. 1 is a diagram of a pHLIP® construct in which an epitope is linked to a pHLIP® peptide.

FIG. 1 shows a construct in which an epitope is linked to a pHLIP® peptide.

Figure 2A:
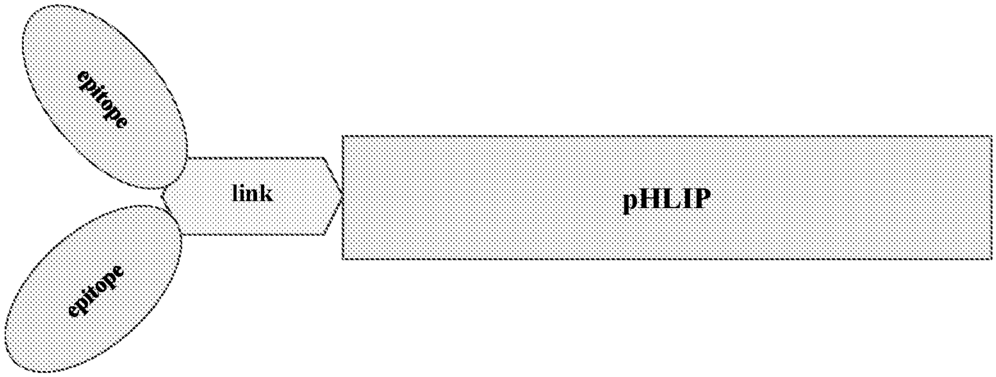
FIG. 2A is a diagram of a pHLIP® construct in which multiple epitopes are linked to a single pHLIP® peptide.
Figure 2B:
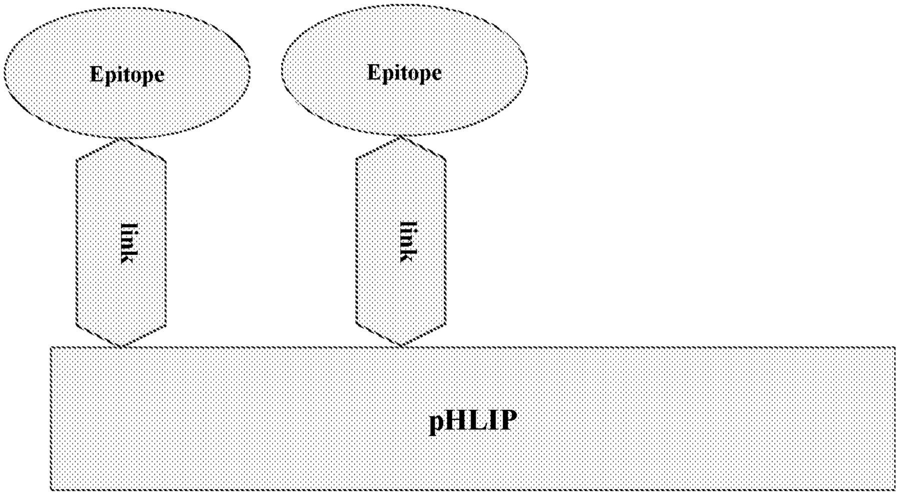
FIG. 2B is a diagram of pHLIP® construct in which two epitopes are linked to a single pHLIP® peptide.

FIGS. 2A and 2B show a construct in which multiple epitopes are linked to a single pHLIP® peptide.

Figure 3:
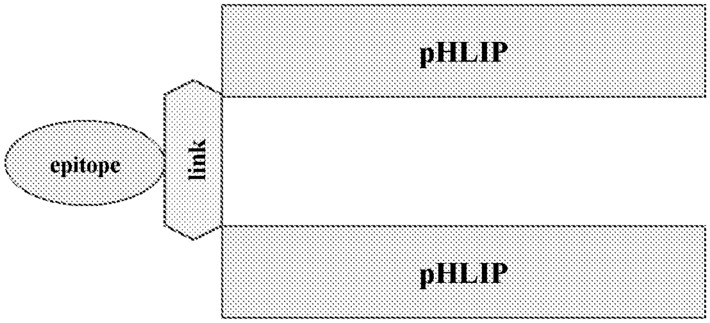
FIG. 3 is a diagram of a pHLIP® construct in which an epitope is linked to multiple pHLIP® peptides.

FIG. 3 shows a construct in which an epitope is linked to multiple pHLIP® peptides.

Figure 4:
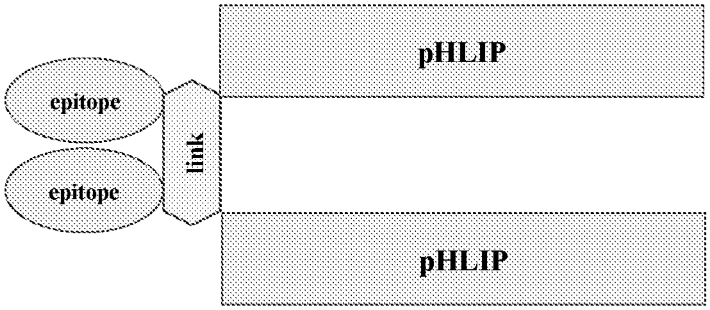
FIG. 4 is a diagram of a pHLIP® construct in which multiple epitopes are linked to multiple pHLIP® peptides.

FIG. 4 shows a construct in which multiple epitopes are linked to multiple pHLIP® peptides.

An exemplary composition comprises the following formula:

Epitope-Linker-Peptide

The "Epitope" may include a peptide, a protein or a fragment thereof, or a small molecule such as an organic molecule, to induce an immune response or promote cell killing by attracting endogenous (pre-existing) immune cells or antibodies, exogenous (administered as in passive antibody-based immunotherapy) engineered immune cells or purified antibodies, ADCs administrated into humans, or antibodies generated in the course of vaccination.

"Peptide" is a pHLIP® peptide (a non-limiting example is a pHLIP® peptide comprising the sequence AXDDQNPWRAYLDLLFPTDTLLLDLLWA (SEQ ID NO: 18) or AXDQDNPWRAYLDLLFPTDTLLLDLLWA (SEQ ID NO: 495), where "X" is a functional group, e.g., for conjugation purposes, selected from a lysine (Lys), a cysteine (Cys), or an Azido-containing amino acid. In some cases "Peptide" is a pHLIP® conjugate, where the pHLIP® peptide is linked with a drug molecule for intracellular delivery.

"Linker" comprises a covalent bond, or a chemical linker, or an extension of the membrane non-inserting flanking region of pHLIP® peptide. If the epitope is a peptide or protein, it may be constructed as an extension of the pHLIP® peptide, and no linker may be required. Non-limiting example of linker is a polyethylene glycol (PEG) polymer in size from 200 Da to 20 kDa. Non-limiting example of an extension is a poly-Glycine polypeptide. Epitope(s) are also linked to pHLIP® peptide(s) via non-cleavable link(s).

Non-limiting examples of a Linker is a mucin domain, which is a high molecular weight, heavily glycosylated protein (glycoconjugate) produced by epithelial tissues in most humans. In other examples, the linker may include biopolymers, including, for example cellulose, starch or chitin.

An exemplary composition comprises the following formula:

Epitope2-Linker2-Pept

The "Epitope" comprises a peptide, a protein or a fragment thereof, or a small molecule such as an organic molecule, to induce an immune response or promote cell killing by attracting endogenous (pre-existing) immune cells or antibodies, exogenous (administered as in passive antibody-based immunotherapy) engineered T-cells or NK-cells or purified antibodies, ADCs administrated into humans, or antibodies generated as a result of vaccination.

"Peptide" is a pHLIP® peptide comprising the sequence: AX(Z)nXPWRAYLDLLFPTDTLLLDLLWA (SEQ ID NO: 496), wherein upper case "X" indicates any amino acid residue, and can include a lysine (Lys), a cysteine (Cys), or an Azido-containing amino acid. The X may be used for conjugation to another moiety. The "Z" indicates any amino acid residue, and n can be any integer between and including 1-10 (e.g., $1 \leq n \leq 10$). For example, (Z)n may be QDNDQN (SEQ ID NO: 497) or any combination of polar amino acid residues including D, E, N or Q.

A compound is characterized as polar if it has a log P of less than −0.4. The epitope compound may be moderately hydrophobic. Polar: Log P<−0.4; Moderately hydrophobic: 2.5<Log P<−0.4; and Hydrophobic: Log P>2.5. The polarity and/or hydrophobicity of an epitope is measured using methods known in the art, e.g., by determining Log P, in which P is the octanol-water partition coefficient. A substance is dissolved into an octanol-water mixture, mixed, and allowed to come to equilibration. The amount of substance in each (or one) phases is then measured. The measurements itself could be in a number of ways known in the art, e.g., by measuring absorbance, or determining the amount using NMR, HPLC, or other known methods. As described herein, moderately hydrophobic, for example, is defined as molecule with Log P value in the range of 2.5 to −0.4, there are a lot of examples.

Linker is a linker, wherein the linker is a polyethylene glycol, PEG For example, the formula PEGm, includes that "m" may be any integer between and including 12 and 24 (e.g., 12≤m≤SPEG12-24 polymer). Each "—" may be a covalent bond.

When an epitope is conjugated to the pHLIP® peptide via a PEG12-24 linker and 6-8 residues are positioned between epitope-PEG attachments to the pHLIP® peptide, the distance between epitopes can be in the range of 5-25 nm.

Alternatively, the distance may be about 10 nm, or 10-15 nm, which corresponds to a typical distance between the two antigen binding sites binding sites of an antibody.

The pHLIP® compositions described are used for decoration of cells in targeted acidic tissue to elicit an immune response or promote delivery of cytotoxic payload by ADCs to kill the diseased cells or tissue.

Non-limiting examples of epitopes are the following:

Peptide Epitope-pHLIP® Peptide Compositions

Peptide antigens, e.g., peptides less than 50 amino acid residues in length, e.g., peptide antigens greater than 5 and less than 20, less than 15, less than 10, or less than 8 amino acid residues.

HER2 (Also Referred to as Receptor Tyrosine-Protein Kinase erbB-2 or Human Epidermal Growth Factor 2)

The HER family of transmembrane tyrosine kinase receptors are composed of four members, BER1 to HER4. HER2 is a ligand-orphan receptor expressed in many human tumors and overexpressed in 25-30% of breast cancers. HER2 amplifies the signal provided by other receptors of the HER family by forming heterodimers. The role of HER2 in the HER signaling network led to the development of anti-HER2 monoclonal antibodies (MAbs) for cancer therapy. In particular, the humanized MAb trastuzumab (Herceptin) or Herceptin-drug conjugates have antitumor activity against HER2-overexpressing human breast tumor cells and are widely used for the treatment of women with HER2 overexpressing breast cancers. One of the primary effects of trastuzumab is to induce antibody-dependent cellular cytotoxicity or promote cell killing by use of ADCs. In addition, trastuzumab induces HER2 receptor down modulation, inhibits critical signaling pathways (i.e. ras-Raf-MAPK and PI3K/Akt), and blocks cell cycle progression by inducing the formation of p27/Cdk2 complexes, inhibits HER2 cleavage, preceding antibody-induced receptor down modulation, which may also contribute to its antitumor activity in some cancers. A limitation of trastuzumab is that its activity is largely restricted to breast cancers with the highest level of HER2 overexpression.

As described above, humanized antibodies against the HER2 receptor have been developed for the treatment of HER2-positive breast cancer. However, not all breast tumors are HER2-positive, some of them are HER2 negative and in some cases during treatment, HER2-positive cancers can transform into HER2 negative cancers, and then treatment is not effective. Also, many other tumors are HER2 negative. The constructs/conjugates described herein decorate all cancer cells (regardless of tissue of origin) with HER2 epitopes to enhance antibody therapy. Useful epitopes include a small peptide mimic of the receptor binding site or a protein-pHLIP® peptide fusion construct, where the protein resembles the entire extracellular domain of a receptor or part of it.

Non-limiting examples of HER2 mimicking peptides, which show high affinity binding to anti-HER-2 monoclonal antibody trastuzumab (Herceptin) include the following peptides:

```
                                        (SEQ ID NO: 1)
QVSHWVSGLAEGSFG

                                        (SEQ ID NO: 2)
LSHTSGRVEGSVSLL

                                        (SEQ ID NO: 3)
QMWAPQWGPD
```

The constructs are useful to decorate all cancer cells with HER2 epitopes to enhance antibody therapy. A useful epitope comprises a small peptide mimic of the receptor binding site or a protein-pHLIP® fusion construct, where the protein resembles the entire extracellular domain of a receptor or part of it. An additional strategy includes use a pHLIP® peptide to position epitopes for therapy using ADCs, some of which have been approved for clinical uses including trastuzumab emtansine, an anti-HER2 antibody conjugated with cytotoxic maytansinois payload (DM1 or mertansine), which is a potent tubulin inhibitor. By targeting the epitopes already in use, or by developing ADCs for new epitopes, the effective use of ADCs is significantly expanded. Other monoclonal antibodies developed for cancer treatment In addition to anti-HER2 antibodies the non-limiting examples of monoclonal antibodies directed against different receptors currently in clinical use for cancer treatment include daratumumab (binds to CD38—cluster of differentiation 38); Ainutuximab (binds to glycolipid GD2—disialoganglioside); bevacizumab (binds to VEGF-A—vascular endothelial growth factor A); cetuximab, necitumumab and panitumumab (bind to EGFR—epidermal growth factor), elotuzumab (binds to CD 319—cluster of differentiation 319), necitumumab (binds EGFR), ramucirumab (binds to VEGFR2). Epitope-pHLIP® constructs could be developed to use with all of these antibodies and their drug conjugates.

Other Examples of Peptide Epitopes

Non-limiting examples of peptide epitopes for conjugation to pHLIP® peptides for which monoclonal antibodies are already developed include:

```
(SEQ ID NO: 4): a T7 peptide derived from the T7
major capsid protein;
MASMTGGQQMG

(SEQ ID NO: 5): a Myc peptide derived from c-Myc;
EQKLISEEDL

(SEQ ID NO: 6): a hemagglutinin (HA) peptide
derived from hemagglutinin;
YPYDVPDYA

(SEQ ID NO: 7): a vesiculovirus (VSV-G) peptide
derived from the vesicular stomatitis viral
glycoprotein;
YTDIEMNRLGK

(SEQ ID NO: 8): an S peptide derived from
pancreatic ribonuclease A;
KETAAAKFERQHMDS

(SEQ ID NO: 9): a V5 peptide derived from the P
and V proteins of the paramyxovirus of simian
virus 5;
GKPIPNPLLGLDST

(SEQ ID NO: 15): a peptide derived from the
protein beta-catenin and optimized for higher
affinity binding to the Spot-Tag Nanobody;
PDRVRAVSHWSS

(SEQ ID NO: 10): a FLAG synthetic peptide;
DYKDDDDK

(SEQ ID NO: 11): an E synthetic peptide;
GAPVPYPDPLEPR

(SEQ ID NO: 12): a Histidine synthetic peptide;
HHHHHH

(SEQ ID NO: 13): an NE synthetic peptide;
TKENPRSNQEESYDDNES
```

-continued (SEQ ID NO: 14): a synthetic peptide recognized by streptavidin;
WSHPQFEK (SEQ ID NO: 7): a vesicular stomatitis virus (VSV) synthetic peptide.
YTDIEMNRLGK Protein Epitope pHLIP® Peptide Compositions In addition to peptide epitopes, larger epitope-containing cytokine proteins may be used for the production of the compositions described. Cytokines are small proteins from 5 to 20 kDa, which perform immuno-modulating role. Among cytokine proteins are IL-17, TNF, CXCL and CCL chemokines.

For example, CXCL9, CXCL10 or CXCL11 chemokine is expressed as N-terminal part of pHLIP® to induce homing and activation of T-cells and NK-cells when pHLIP® inserts into cellular membrane and tethers CXCL9 or CXCL10 or CXCL11 proteins to surface of membrane.

The cytokine can be expressed together with a mucin-domain (a glycosylated protein) as a linker (spacer) between cytokine and pHLIP® peptide to allow the cytokine to be fully exposed to the extracellular space.

The nucleic acid sequence encoding CXCL10 chemokine and the amino acid sequence of the protein antigen is described below.

SEQ ID NO: 498
```
ccagtctcagcaccatgaatcaaactgccattctgatttgctgccttatct
ttctgactctaagtggcattcaaggagtacctctctctagaactgtacgct
gtacctgcatcagcattagtaatcaacctgttaatccaaggtctttagaaa
aacttgaaattattcctgcaagccaattttgtccacgtgttgagatcattg
ctacaatgaaaaagaagggtgagaagagatgtctgaatccagaatcgaagg
ccatcaagaatttactgaaagcagttagcaaggaaaggtctaaaagatctc
ct
```

The amino acid sequence of CXCL 10 is provided below.

(SEQ ID NO: 514)
```
mnqtailicc lifltlsgiq gvplsrtvrc tcisisnqpv
nprsleklei ipasqfcprv eiiatmkkkg ekrclnpesk
aiknllkavs kerskrsp
```

His or myc tags are used for purification purposes and not needed for use as an antigen (e.g., for conjugation to a pHLIP® peptide).

daltons, 300 daltons, 200 daltons, or 100 daltons. Some small molecule antigens are characterized by their binding to endogenous antibodies in the blood or serum of many normal humans (or humans characterized as having a pathological tumor).

Exemplary small molecule epitopes are described below.

Di-nitrophenvl (DNP)

Antibodies to DNP (0-(2,4-dinitrophenyl)hydroxylamine, shown below) have been identified in the IgG fraction of normal human sera.

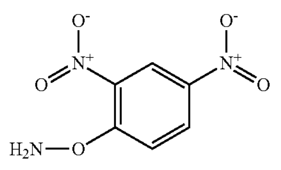 [SMILES: NOc1ccc([N+](=O)[O-])cc1[N+](=O)[O-]]

Thus, another small molecule antigen that binds endogenous antibodies is dinitrophenyl (DNP) and its derivatives. For example, N-(4-dimethylamino-3,5-dinitrophenyl)maleimide is shown below:

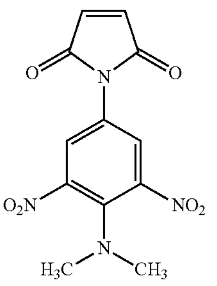 [SMILES: CN(C)c1c([N+](=O)[O-])cc(N2C(=O)C=CC2=O)cc1[N+](=O)[O-]]

OrDNP-PEG4-NHS (1-(2,4-Dinitrophenylamino)-3,6,9,12-tetraoxapentadecanoic acid succinimidyl ester) is shown below:

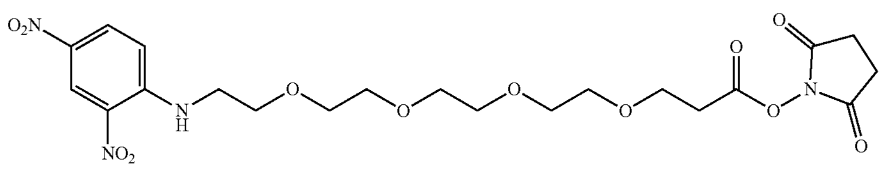 [SMILES: O=C(CCOCCOCCOCCOCCNc1ccc([N+](=O)[O-])cc1[N+](=O)[O-])ON1C(=O)CCC1=O]

Small Molecule Antigens or Epitopes

Small molecule antigens are those that are characterized by a molecular mass of less than 2000 daltons. For example, the molecular mass of the small molecule antigen is preferably less than 1000 daltons, more preferably less than 600 daltons, e.g., the compound is less than 500 daltons, 400

DNP is a low molecular weight antigen known for its ability to bind antibodies in normal human serum. Binding of the antibodies to DNP delivered to the surface of tumor or otherwise diseased acidic cells leads to cytotoxicity of the antigen-labeled target cells. The DNP recruits endogenous antibodies, e.g., antibodies that exist in a subject prior to administration of the pHLIP® peptide constructs described herein.

Linker

In the schematic structure, Epitope-Linker-Peptide:

Linker could be relatively small, e.g., only a few atoms, to a rather large polar (or moderately hydrophobic) polymer or an N-terminal lengthening of the pHLIP® peptide by the addition of amino acids, e.g., glycine residues (poly-Gly). In some examples, a linker can be part of membrane non-inserting pHLIP® peptide sequence, such as those with a poly-Gly motif. In some examples, a linker could be PEG polymer. The purpose of a polymer or pHLIP® extension is to position epitopes at the surfaces of cells to enhance the access of antibodies or proteins for binding to the epitope. Non-limiting example of linker is a PEG polymer in size from 200 Da up to 20 kDa.

In some examples the following linkers and their derivatives could be used: N-α-maleimidoacet-oxysuccinimide ester (AMAS); N-γ-maleimidobutyryl-oxysuccinimide ester (GMBS); N-β-maleimidopropyl-oxysuccinimide ester (BMPS); N-ε-malemidocaproyl-oxysuccinimide ester (EMCS); m-maleimidobenzoyl-n-hydroxysuccinimide ester (MBS); succinimidyl 3-(bromoacetamido)propionate (SBAP); succinimidyl (4-iodoacetyl)aminobenzoate (SIAB); N-ε-maleimidocaproic acid (EMCA); succinimidyl 4-(n-maleimidomethyl)cyclohexane-1-carboxy-(6-amidocaproate) (LC-SMCC); succinimidyl iodoacetate (SIA); succinimidyl (4-iodoacetyl)aminobenzoate (SIAB); succinimidyl 4-(p-maleimidophenyl)butyrate (SMPB); succinimidyl 6-((beta-maleimidopropionamido)hexanoate) (SMPH); 3-propargyloxypropanoic acid, succinimidyl ester (alkyne, succinimidyl ester); 1,4-bismaleimidobutane (BMB); bismaleimidohexane (BMH); bismaleimidoethane (BMOE); tris(2-maleimidoethyl)amine (TMEA); N-β-maleimidopropionic acid hydrazide; (BMPH); N-ε-maleimidocaproic acid hydrazide (EMCH); N-κ-maleimidoundecanoic acid hydrazide (KMUH); 4-(4-n-maleimidophenyl)butyric acid hydrazide (MBPH); or p-maleimidophenyl isocyanate (PMPI).

In some examples the flexible linker or mucin domain is positioned between epitope and pHLIP® peptide.

The mucin-domain of CX3CL1 and the nucleic acid sequence encoding mucin-domain of CX3CL1 is described below:

SEQ ID NO: 500

```
aatggcggcaccttcgagaagcagatcggcgaggtgaagcccaggaccacc

cctgccgccggggggaatggacgagtctgtggtcctggagcccgaagccaca
```

-continued

```
ggcgaaagcagtagcctggagccgactccttcttcccaggaagcacagagg

gccctggggacctccccagagctgccgacgggtgtgactggttcctcaggg

accaggctccccccgacgccaaaggctcaggatggagggcctgtgggcacg

gagcttttccgagtgcctcccgtctccactgccgccacgtggcagagttct

gctccccaccaacctgggcccagcctctgggctgaggcaaagacctctgag

gccccgtccacccaggacccctccacccaggcctccactgcgtcctcccca

gccccagaggagaatgctccgtctgaaggccagcgtgtgtggggtcagggg

cagagccccaggccagagaactctctggagcgggaggagatgggtcccgtg

ccagcgcacacggatgccttccaggactgggggcctggcagcatggcccac

gtctctgtggtccctgtctcctcagaagggacccccagcagggagccagtg

gcttcaggcagctggacccctaaggctgaggaacccatccatgccaccatg

gacccccagaggctgggcgtccttatcactcctgtccctgacgcccaggct

gccacccggaggcag
```

The sequence of mucin-domain of the human CX3CL1 protein (UniProt P78423 or NP_002987.1) is shown below (these are residues 111-141 from the human CX3CL1 protein):

SEQ ID NO: 526

```
gtfekqigev kprttpaagg mdesvvlepe atgessslep

tpssqeaqra lgtspelptg vtgssgtrlp ptpkaqdggp

vgtelfrvpp vstaatwqss aphqpgpslw aeaktseaps

tqdpstqast asspapeena psegqrvwgq gqsprpensl

ereemgpvpa htdafqdwgp gsmahvsvvp vssegtpsre

pvasgswtpk aeepihatmd pqrlgvlitp vpdaqaatrr q
```

The full length CXCL1 amino acid sequence is depicted below (NP_002987.1), and incorporated herein by reference.

SEQ ID NO: 527

```
  1 mapislswll rlatfchltv llagqhhgvt kcnitcskmt skipvallih yqqnqascgk

 61 raiiletrqh rlfcadpkeq wvkdamqhld rqaaaltrng gtfekqigev kprttpaagg

121 mdesvvlepe atgessslep tpssqeaqra lgtspelptg vtgssgtrlp ptpkaqdggp

181 vgtelfrvpp vstaatwqss aphqpgpslw aeaktseaps tqdpstqast asspapeena

241 psegqrvwgq gqsprpensl ereemgpvpa htdafqdwgp gsmahvsvvp vssegtpsre

301 pvasgswtpk aeepihatmd pqrlgvlitp vpdaqaatrr qavgllaflg llfclgvamf

361 tyqslqgcpr kmagemaegl ryiprscgsn syvlvpv
```

Exemplary landmark residues, domains, and fragments of CXCL1 include, but are not limited to residues 1-24 (signal peptide), residues 25-397 (mature peptide), or residues 111-141 (as described above). A fragment (e.g., a peptide or an epitope) of a CXCL1 protein is less than the length of the full length protein, e.g., a fragment is at least 3, 4, 5, 6, 7, 8, 9, 10, 20, 30, 40, 50, 100, 200 or more residues in length, but less than e.g., 397 residues in the case of CXCL1 above.

pHLIP® Peptides

In the schematic structure, Epitope-Linker-Peptide:

Peptide is a pHLIP® peptide (non-limiting example is pHLIP® comprising the Var3 sequence AXDDQNPWRAYLDLLFPTDTLLLDLLWA (SEQ ID NO: 18) or AXDQDNPWRAYLDLLFPTDTLLLDLLWA (SEQ ID NO: 495), where X is a functional group for conjugation purposes, selected from a lysine (Lys), a cysteine (Cys), or Azido-containing amino acid or others. The membrane non-inserting N-terminal flanking sequence of pHLIP® peptide can be extend. For example, the pHLIP® peptide shares the sequence: WRAYLDLLFPTDTLLLDLLW (SEQ ID NO: 112).

Non-limiting examples of the extension can be poly-Gly motif or AX(Z)nXPWRAYLDLLFPTDTLLLDLLWA (SEQ ID NO: 496), where "Z" indicates any amino acid residue, and n is any integer between and including 1-10 (e.g., 1≤n≤10). Additionally, (Z)n could be QDNDQN (SEQ ID NO: 497) or NENENN (SEQ ID NO: 528) or NDNDNN (SEQ ID NO: 529) or NDNDNDN (SEQ ID NO:530), any combination of polar residues, D, E, N or Q.

An example of a wild type (WT) pHLIP® peptide is AXEQNPIYWARYADWLFTTPLLLLDLALLVDADEGT (SEQ ID NO: 20) where X is a functional group for conjugation purposes, selected from a lysine (Lys), a cysteine (Cys), an Azido-containing amino acid, or others, and in which AEQNPIY (SEQ ID NO: 501) represents a flanking sequence, WARYADWLFTTPLLLLDLALLV (SEQ ID NO: 21) represents a membrane-inserting sequence, and DADEGT represents a flanking sequence.

The constructs may include a pHLIP® peptide with a N-terminal extension. For example, the N terminus of any of these peptide sequences can be extended by the addition of amino acids to space the epitope away from the cell surface, e.g. by including a (glycine) extension.

Other exemplary pHLIP® peptides are shown in the Tables below.

TABLE 1

Exemplary pHLIP ® peptides

| Name | Sequence | SEQ ID No. |
|---|---|---|
| Var3-1a | ACDQDNPWRAYLDLLFPTDTLLLDLLWA | SEQ. ID NO. 537 |
| Var3-1b | AKDQDNPWRAYLDLLFPTDTLLLDLLWA | SEQ. ID NO. 538 |
| Var3-2a | ACQDNDQNCPWRAYLDLLFPTDTLLLDLLWA | SEQ. ID NO. 539 |
| Var3-2b | AKQDNDQNKPWRAYLDLLFPTDTLLLDLLWA | SEQ. ID NO. 540 |
| WT-1 | GGEQNPIYWARYADWLFTTPLLLLDLALLVDADEGT | SEQ. ID NO. 22 |
| WT-2 | AEQNPIYWARYADWLFTTPLLLLDLALLVDADEGT | SEQ. ID NO. 23 |
| Var3-WT-Cys | ADDQNPWRAYLDLLFPTDTLLLDLLWDADECG | SEQ. I NO. 24 |
| Cys-Var3-WT | ACDDQNPWRAYLDLLFPTDTLLLDLLWDADEG | SEQ. I NO. 25 |
| Lys-Var3-WT | **AKDDQNPWRAYLDLLEPTDTELLDLLWDADEG** | SEQ. I NO. 26 |
| WT-Cys1 | AAEQNPIYWARYADWLFTTPLLLLDLALLVDADEGTCG | SEQ. ID NO. 27 |
| WT-Cys2 | Ac-AEQNPIYWARYADWLFTTPLLLLDLALLVDADEGCT | SEQ ID NO: 28 |
| WT-Cys3 | GGEQNPIYWARYADWLFTTPLLLLDLALLVDADEGTCG | SEQ. ID NO. 29 |
| Cys-WT1 | Ac-ACEQNPIYWARYADWLFTTPLLLLDLALLVDADEGTG | SEQ. ID NO. 30 |
| Var0-NT | ACEQNPIYWARYADWLFTTPLLLLDLALLVDADEGT | SEQ. ID NO. 31 |
| Lys-WT1 | AKEQNPIYWARYADWLFTTPLLLLDLALLVDADEGT | SEQ. ID NO. 32 |
| Lys-WT2 | Ac-AKEQNPIYWARYADWLFTTPLLLLDLALLVDADEGTG | SEQ ID NO: 33 |
| WT-KC | AAEQNPIYWARYADWLFTTPLLLLDLALLVDADEGTKCG | SEQ. ID NO. 34 |
| K-WT-C | AKEQNPIYWARYADWLFTTPLLLLDLALLVDADECT | SEQ. ID NO. 35 |
| N-pHLIP ® | ACEQNPIYWARYANWLFTTPLLLLNLALLVDADEGTG | SEQ. ID NO. 36 |
| N-pHLIP ®-b | ACEQNPIYWARYANWLFTTPLLLLNLALLVDADEGT | SEQ ID NO: 37 |
| K-pHLIP ® | ACEQNPIYWARYAKWLFTTPLLLLKLALLVDADEGTG | SEQ. ID NO. 38 |
| NNQ | GGEQNPIYWARYADWLFTTPLLLLDLALLVNANQGT | SEQ. ID NO. 39 |
| D25A | AAEQNPIYWARYADWLFTTPLLLLALALLVDADEGT | SEQ. ID NO. 40 |
| D25A-KC | Ac-AAEQNPIYWARYADWLFTTPLLLLELALLVDADEGTKCG | SEQ ID NO: 41 |
| D14A | AAEQNPIYWARYAAWLFTTPLLLLDLALLVDADEGT | SEQ. ID NO. 42 |
| P20A | AAEQNPIYWARYADWLFTTALLLLDLALLVDADEGT | SEQ. ID NO. 43 |
| D25E | AAEQNPIYWARYADWLFTTPLLLLELALLVDADEGT | SEQ. ID NO. 44 |

TABLE 1-continued

| Exemplary pHLIP ® peptides | | |
|---|---|---|
| Name | Sequence | SEQ ID No. |
| D14E | AAEQNPIYWARYAEWLFTTPLLLLDLALLVDADEGT | SEQ. ID NO. 45 |
| 3D | AAEQNPIIYWARYADWLFTDLPLLLLDLLALLVDADEGT | SEQ. ID NO. 46 |
| R11Q | GEQNPIYWAQYADWLFTTPLLLLDLALLVDADEGTCG | SEQ. ID NO. 47 |
| D25Up | GGEQNPIYWARYADWLFTTPLLLDLLALLVDADEGTCG | SEQ. ID NO. 48 |
| D25Down | GGEQNPIYWARYADWLFTTPLLLLLDALLVDADEGTCG | SEQ. ID NO. 49 |
| D14Up | GGEQNPIYWARYDAWLFTTPLLLLDLALLVDADEGTCG | SEQ. ID NO. 50 |
| D14Down | GGEQNPIYWARYAWDLFTTPLLLLDLALLVDADEGTCG | SEQ. ID NO. 51 |
| P20G | AAEQNPIYWARYADWLFTTGLLLLDLALLVDADEGT | SEQ. ID NO. 52 |
| H1-Cys | DDDEDNPIYWARYADWLFTTPLLLLHGALLVDADECT | SEQ. ID NO. 53 |
| H1 | DDDEDNPIYWARYADWLFTTPLLLLHGALLVDADET | SEQ ID NO: 54 |
| H2-Cys | DDDEDNPIYWARYAHWLFTTPLLLLHGALLVDADEGCT | SEQ. ID NO. 55 |
| Cys-H2 | CDDDEDNPIYWARYAHWLFTTPLLLLHGALLVDADET | SEQ ID NO: 56 |
| H2 | DDDEDNPIYWARYAHWLFTTPLLLLHGALLVDADEGT | SEQ ID NO: 57 |
| H2N-Cys | DDDEDNPIYWARYAHWLFTTPLLLLHGALLVNADECT | SEQ. ID NO. 58 |
| H2N | DDDEDNPIYWARYAHWLFTTPLLLLHGALLVNADEGT | SEQ ID NO: 59 |
| H2N2-Cys | DDDEDNPIYWARYAHWLFTTPLLLLHGALLVNANECT | SEQ. ID NO. 60 |
| H2N2 | DDDEDNPIYWARYAHWLFTTPLLLLHGALLVNANEGT | SEQ ID NO: 61 |
| 1a-Trp | AEQNPIYWARYADFLFTTPLLLLDLALLVDADET | SEQ. ID NO. 62 |
| 1b-Trp | AEQNPIYFARYADWLFTTPLLLLDLALLVDADEGT | SEQ. ID NO. 63 |
| 1c-Trp | AEQNPIYFARYADFLFTTPLLLLDLALLWDADET | SEQ. ID NO. 64 |
| Fast-1 or Var1 | AKEDQNPYWARYADWLFTTPLLLLDLALLVDG | SEQ. ID NO. 65 |
| Var1-2D1D | ACEDQNPYWARYADWLFTTPLLLLDLALLVDG | SEQ. ID NO. 66 |
| Fast1-Cys or Var1-2D1D-Cys | AEDQNPYWARYADWLFTTPLLLLDLALLVDCG | SEQ. ID NO. 67 |
| Fast1-E-Cys or Var1E | AEDQNPYWARYADWLFTTPLLLLELALLVECG | SEQ. ID NO. 68 |
| Fast1-E-Lys | AKEDQNDPYWARYADWLFTTPLLLLDLALLVG | SEQ ID NO: 69 |
| Fast2 or Var2 | AKEDQNPYWRAYADLFTPLTLLDLLALWDG | SEQ. ID NO. 70 |
| Fast2-E-Cys or Var2E | AEDQNPYWARYADWLFTTPLLLLELALLVCG | SEQ ID NO: 71 |
| Var2-2D1D | ACEDQNPYWRAYADLFTPLTLLDLLALWDG | SEQ. ID NO. 72 |
| Var3-3D | ACDDQNPWRAYLDLLFPTDTLLLDLLW | SEQ. ID NO. 73 |
| Var3-3D-cys | AKDDQNPWRAYLDLLFPTDTLLLDLLWC | SEQ ID NO: 74 |
| Var4-3E | ACEEQNPWRAYLELLFPTETLLLELLW | SEQ ID NO: 75 |
| Var5-3Da | ACDDQNPWARYLDWLFPTDTLLLDL | SEQ ID NO: 76 |
| Var6-3Db | CDNNNPWRAYLDLLFPTDTLLLDW | SEQ ID NO: 77 |
| Var8-3Eb | CEEQQPWAQYLELLFPTETLLLEW | SEQ ID NO: 78 |
| Var9-3Ec | CEEQQPWRAYLELLFPTETLLLEW | SEQ ID NO: 79 |

TABLE 1-continued

| Exemplary pHLIP ® peptides | | |
|---|---|---|
| Name | Sequence | SEQ ID No. |
| Var15-2N | CDDDDDNPNYWARYANWLFTTPLLLLNGALLVEAEET | SEQ ID NO: 80 |
| Var16-2P | CDDDDDNPNYWARYAPWLFTTPLLLLPGALLVEAEE | SEQ ID NO: 81 |

TABLE 2

| Exemplary pHLIP ® peptides | | |
|---|---|---|
| Name | Sequence | SEQ ID No. |
| Var14-Rev | Ac-TEDADVLLALDLLLLPTTFLW DAYRAWYPNQECA-Am | SEQ. ID NO. 82 |
| Sh | AEQNPIYWARYADWLFTTPL | SEQ. ID NO. 83 |
| Sh-Cys | AEQNPIYWARYADWLFTTPCL | SEQ. ID NO. 84 |
| Cys-Sh | ACEQNPIYWARYADWLFTTPL | SEQ. ID NO. 85 |
| Sh-1Trp | AEQNPIYFARYADWLFTTPL | SEQ. ID NO. 86 |
| Sh-W2 | AEQNPIYFARYADLLFPTTLAW | SEQ ID NO: 87 |
| Sh-W1 | AEQNPIYWARYADLLFPTTLAF | SEQ ID NO: 88 |
| Sh-2W | AEQNPIYWARYADLLFPTTLAW | SEQ ID NO: 89 |
| Sh-1D | KEDQNPWARYADLLFPTTLAW | SEQ. ID NO. 90 |
| Sh-1Db | KEDQNPWARYADLLFPTTLW | SEQ ID NO: 91 |
| Var12-1D | ACEDQNPWARYADLLFPTTLAW | SEQ. ID NO. 92 |
| Var10-2D | ACEDQNPWARYADWLFPTTLLLLD | SEQ. ID NO. 93 |
| Var13-1E | ACEEQNPWARYAELLFPTTLAW | SEQ. ID NO. 94 |
| Var11-2E | ACEEQNPWARYAEWLFPTTLLLLE | SEQ. ID NO. 95 |
| Var7-3E | ACEEQNPWARYLEWLFPTETLLLEL | SEQ. ID NO. 96 |
| Var7-3Eb | ACEEQNPQAEYAEWLFPTTLLLLE | SEQ ID NO: 97 |

"Ac" means Acetylated N-terminus
"Am" means Amidated C-terminus

TABLE 3

| Coded and exemplary non-coded amino acids including L-isomers, D-isomers, alpha-isomers, beta-isomers, glycol-, and methyl- modifications. | | |
|---|---|---|
| No. | Abbrev | Name |
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |

TABLE 3-continued

| Coded and exemplary non-coded amino acids including L-isomers, D-isomers, alpha-isomers, beta-isomers, glycol-, and methyl- modifications. | | |
|---|---|---|
| No. | Abbrev | Name |
| 18 | Trp | Tryptophan |
| 19 | Tyr | Tyrosine |
| 20 | Val | Valine |
| 21 | Sec | Selenocysteine |
| 22 | Sem | Selenomethionine |
| 23 | Pyl | Pyrrolysine |
| 24 | Aad | Alpha-aminoadipic acid |
| 25 | Acpa | Amino-caprylic acid |
| 26 | Aecys | Aminoethyl cysteine |
| 27 | Afa | Aminophenyl acetate |
| 28 | Gaba | Gamma-aminobutyric acid |
| 29 | Aiba | Aminoisobutyric acid |
| 30 | Aile | Alloisoleucine |
| 31 | AIg | Allylglycine |
| 32 | Aba | Amino-butyric acid |
| 33 | Aphe | Amino-phenylalanine |
| 34 | Brphe | Bromo-phenylalanine |
| 35 | Cha | Cyclo-hexylalanine |
| 36 | Cit | Citrulline |
| 37 | Clala | Chloroalanine |
| 38 | Cie | Cycloleucine |
| 39 | Clphe | Fenclonine (or chlorophenylalanine) |
| 40 | Cya | Cysteic acid |
| 41 | Dab | Diaminobutyric acid |
| 42 | Dap | Diaminopropionic acid |
| 43 | Dap | Diaminopimelic acid |
| 44 | Dhp | Dehydro-proline |
| 45 | Dhphe | DOPA (or 3,4-dihydroxyphenylalanine) |
| 46 | Fphe | Fluorophenylalanine |
| 47 | Gaa | Glucosaminic acid |
| 48 | Gla | Gamma-carboxyglutamic acid |
| 49 | Hag | Homoarginine |
| 50 | Hlys | Hydroxylysine |
| 51 | Hnvl | Hydroxynorvaline |
| 52 | Hog | Homoglutamine |
| 53 | Hoph | Homophenylalanine |
| 54 | Has | Homoserine |
| 55 | Hse | Homocysteine |
| 56 | Hpr | Hydroxyproline |
| 57 | Iphe | Iodo-phenylalanine |
| 58 | Ise | Isoserine |
| 59 | Mle | Methyl-leucine |
| 60 | Msmet | Methionine-methylsulfonium chloride |
| 61 | Nala | Naphthyl-alanine |
| 62 | Nle | Norleucine (or 2-aminohexanoic acid) |
| 63 | Nmala | N-methyl-alanine |
| 64 | Nva | Norvaline (or 2-aminopentanoic acid) |
| 65 | Obser | O-benzyl-serine |
| 66 | Obtyr | O-benzyl-tyrosine |
| 67 | Oetyr | O-ethyl-tyrosine |
| 68 | Omser | O-methyl-serine |
| 69 | Omthr | O-methy-threonine |
| 70 | Omtyr | O-methyl-tyrosine |
| 71 | Orn | Ornithine |
| 72 | Pen | Penicillamine |
| 73 | Pga | Pyroglutamic acid |
| 74 | Pip | Pipecolic acid |
| 75 | Sar | Sarcosine |
| 76 | Tfa | Trifluoro-alanine |
| 77 | Thphe | Hydroxy-Dopa |

TABLE 3-continued

Coded and exemplary non-coded amino acids including L-isomers, D-isomers, alpha-isomers, beta-isomers, glycol-, and methyl- modifications.

| No. | Abbrev | Name |
|---|---|---|
| 78 | Vig | Vinylglycine |
| 79 | Aaspa | Amino-aminoethylsulfanylpropanoic acid |
| 80 | Ahdna | Amino-hydroxy-dioxanonanolic acid |
| 81 | Ahoha | Amino-hydroxy-oxahexanoic acid |
| 82 | Ahsopa | Amino-hydroxyethylsulfanylpropanoic acid |
| 83 | Tyr(Me) | Methoxyphenyl-methylpropanyl oxycarbonylamino propanoic acid |
| 84 | MTrp | Methyl-tryptophan |
| 85 | pTyr | Phosphorylated Tyr |
| 86 | pSer | Phosphorylated Ser |
| 87 | pThr | Phosphorylated Thr |
| 88 | BLys | BiotinLys |
| 89 | Hyp | Hydroproline |
| 90 | Phg | Phenylglycine |
| 91 | Cha | Cyclohexyl-alanine |
| 92 | Chg | Cyclohexylglycine |
| 93 | Nal | Naphthylalanine |
| 94 | Pal | Pyridyl-alanine |
| 95 | Pra | Propargylglycine |
| 96 | Gly(allyl) | Pentenoic acid |
| 97 | Pen | Penicillamine |
| 98 | MetO | Methionine sulfoxide |
| 99 | Pca | Pyroglutamic acid |
| 100 | Ac-Lys | Acetylation of Lys |

TABLE 4

Non-limiting examples of protonatable residues and their substitutions including L-isomers, D-isomers, alpha-isomers, and beta-isomers.

| Original Residue | Exemplary amino acids substitution |
|---|---|
| Asp (D) | Glu (E); Gla (Gla); Aad (Aad) |
| Glu (E) | Asp (D); Gla (Gla); Aad (Aad) |

TABLE 5

Examples of coded amino acid substitutions

| Original Residue | Substitution |
|---|---|
| Ala (A) | Gly; Ile; Leu; Met; Phe; Pro; Trp; Tyr; Val |
| Arg (R) | Lys |
| Asn (N) | Gln; His |
| Asp (D) | Glu |
| Cys (C) | Ser; Met |
| Gln (Q) | Asn; His |
| Glu (E) | Asp |
| Gly (G) | Ala; Ile; Leu; Met; Phe; Pro; Trp; Tyr; Val |
| His (H) | Asn; Gln |
| Ile (I) | Ala; Gly; Leu; Met; Phe; Pro; Trp; Tyr; Val |
| Leu (L) | Ala; Gly; Ile; Met; Phe; Pro; Trp; Tyr; Val |
| Lys (K) | Arg |
| Met (M) | Ala; Gly; Leu; Ile; Phe; Pro; Trp; Tyr; Val |
| Phe (F) | Ala; Gly; Leu; Ile; Met; Pro; Trp; Tyr; Val |
| Pro (P) | Ala; Gly; Leu; Ile; Met; Phe; Trp; Tyr; Val |
| Ser (S) | Thr |
| Thr (T) | Ser |
| Trp (W) | Ala; Gly; Leu; Ile; Met; Pro; Phe; Tyr; Val |
| Tyr (Y) | Ala; Gly; Leu; Ile; Met; Pro; Phe; Trp; Val |
| Val (V) | Ala; Gly; Leu; Ile; Met; Pro; Phe; Trp; Tyr |

TABLE 6

Non-limiting examples of membrane-inserting sequences belonging to different groups of pHLIP ® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences |
|---|---|
| WT-BRC | WARYA**D**WLFTTPLLLL**D**LALL (SEQ ID NO: 98) |
| | YARYA**D**WLFTTPLLLL**D**LALL (SEQ ID NO: 99) |
| | WARYS**D**WLFTTPLLLY**D**LGLL (SEQ ID NO: 100) |
| | WARYT**D**WFTTPLLLY**D**LALLA (SEQ ID NO: 101) |
| | WARYT**D**WLFTTPLLLY**D**LGLL (SEQ ID NO: 102) |
| | WARYA**D**WLFTTPLLLL**D**LSLL (SEQ ID NO: 103) |
| WT-BRC Reverse | LLAL**D**LLLLPTTFLW**D**AYRAW (SEQ ID NO: 104) |
| | LLAL**D**LLLLPTTFLW**D**AYRAY (SEQ ID NO: 105) |
| | LLGL**D**YLLLPTTFLW**D**SYRAW (SEQ ID NO: 106) |
| | ALLAL**D**YLLLPTTFW**D**TYRAW (SEQ ID NO: 107) |
| | LLGL**D**YLLLPTTFLW**D**TYRAW (SEQ ID NO: 108) |
| | LLSL**D**LLLLPTTFLW**D**AYRAW (SEQ ID NO: 109) |
| ATRAM | GLAGLLGL**E**GLLGLPLGLL**E**GLWLGL (SEQ ID NO: 110) |
| ATRAM Reverse | LGLWLG**E**LLGLPLGLLG**E**LGLLGALG (SEQ ID NO: 111) |
| Var3 | WRAYL**D**LLFPT**D**TLLL**D**LLW (SEQ ID NO: 112) |
| Var3 Reverse | WLL**D**LLLT**D**TPFLL**D**LYARW (SEQ ID NO: 113) |
| Var7 | WARYL**E**WLFPT**E**TLLL**E**L (SEQ ID NO: 114) |
| | WAQYL**E**LLFPT**E**TLLL**E**W (SEQ ID NO: 115) |
| Var7 Reverse | LELLLT**E**TPFLW**E**LYRAW (SEQ ID NO: 116) |
| | WELLLT**E**TPFLL**E**LYQAW (SEQ ID NO: 117) |
| Single D/E | WLFTTPLLLLNGALLV**E** (SEQ ID NO: 118) |
| | WLFTTPLLLLPGALLV**E** (SEQ ID NO: 119) |
| | WARYA**D**LLFPTTLAW (SEQ ID NO: 120) |
| Single D/E Reverse | **E**VLLAGNLLLLPTTFLW (SEQ ID NO: 121) |
| | **E**VLLAGPLLLLPTTFLW (SEQ ID NO: 122) |
| | WALTTPFLL**D**AYRAW (SEQ ID NO: 123) |
| pHLIP ®-Rho | NL**E**GFFATLGG**E**IALWSLVVLAI**E** (SEQ ID NO: 124) |
| | **E**GFFATLGG**E**IALWSDVVLAI**E** (SEQ ID NO: 125) |
| | **E**GFFATLGG**E**IPLWSDVVLAI**E** (SEQ ID NO: 126) |
| pHLIP ®-Rho Reverse | **E**IALVVLSWLAI**E**GGLTAFFG**E**LN (SEQ ID NO: 127) |
| | **E**IALVVDSWLAI**E**GGLTAFFG**E** (SEQ ID NO: 128) |
| | **E**IALVVDSWLPI**E**GGLTAFFG**E** (SEQ ID NO: 129) |
| pHLIP ®-CA9 | IL**D**LVFGLLFAVTSV**D**FLVQW (SEQ ID NO: 130) |
| pHLIP ®-CA9 Reverse | WQVLF**D**VSTVAFLLGFVL**D**LI (SEQ ID NO: 131) |

TABLE 7

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 132 | WT-2D | AEQNPIYWARYADWLFTTPLLLLDLALLVDADET |
| SEQ ID NO: 133 | WT-6E | AEQNPIYWARYAEWLFTTPLLLLELALLVEAEET |
| SEQ ID NO: 134 | WT-3D | ADDQNPWRAYLDLLFPDTTDLLLLDLLWDADET |
| SEQ ID NO: 135 | WT-9E | AEEQNPWRAYLELLFPETTELLLLELLWEAEET |
| SEQ ID NO: 136 | WT-GlaD | AEQNPIYWARYA*Gla*WLFTTPLLLLDLALLVDADET |
| SEQ ID NO: 137 | WT-DGla | AEQNPIYWARYADWLFTTPLLLL*Gla*LALLVDADET |
| SEQ ID NO: 138 | WT-2Gla | AEQNPIYWARYA*Gla*WLFTTPLLLL*Gla*LALLVDADET |
| SEQ ID NO: 139 | WT-AadD | AEQNPIYWARYA*Aad*WLFTTPLLLLDLALLVDADET |
| SEQ ID NO: 140 | WT-DAad | AEQNPIYWARYADWLFTTPLLLL*Aad*LALLVDADET |
| SEQ ID NO: 141 | WT-2Aad | AEQNPIYWARYA*Aad*WLFTTPLLLL*Aad*LALLVDADET |
| SEQ ID NO: 142 | WT-GlaAad | AEQNPIYWARYA*Gla*WLFTTPLLLL*Aad*LALLVDADET |
| SEQ ID NO: 143 | WT-AadGla | AEQNPIYWARYA*Aad*WLFTTPLLLL*Gla*LALLVDADET |
| SEQ ID NO: 144 | WT-1 | GGEQNPIYWARYADWLFTTPLLLLDLALLVDADEGT |
| SEQ ID NO: 145 | WT-2 | GGEQNPIYWARYADWLFTTPLLLLDLALLVDADEGT |
| SEQ ID NO: 146 | WT-3 | AAEQNPIYWARYADWLFTTPLLLLDLALLVDADEGT |
| SEQ ID NO: 147 | WT-4 | AEQNPIYWARYADWLFTTPLLLLDLALLVDADEGT |
| SEQ ID NO: 148 | WT-2N | AEQNPIYWARYANWLFTTPLLLLNLALLVDADEGT |
| SEQ ID NO: 149 | WT-2K | AEQNPIYWARYAKWLFTTPLLLLKLALLVDADEGT |
| SEQ ID NO: 150 | WT-2DNANQ | GGEQNPIYWARYADWLFTTPLLLLDLALLVNANQGT |
| SEQ ID NO: 151 | WT-D25A | AAEQNPIYWARYADWLFTTPLLLLALALLVDADEGT |
| SEQ ID NO: 152 | WT-D14A | AAEQNPIYWARYAAWLFTTPLLLLDLALLVDADEGT |
| SEQ ID NO: 153 | WT-P20A | AAEQNPIYWARYADWLFTTALLLLDLALLVDADEGT |
| SEQ ID NO: 154 | WT-D25E | AAEQNPIYWARYADWLFTTPLLLLELALLVDADEGT |
| SEQ ID NO: 155 | WT-D14E | AAEQNPIYWARYAEWLFTTPLLLLDLALLVDADEGT |
| SEQ ID NO: 156 | WT-3D-2 | AAEQNPIIYWARYADWLFTDLPLLLLDLLALLVDADEGT |
| SEQ ID NO: 157 | WT-R11Q | GEQNPIYWAQYADWLFTTPLLLLDLALLVDADEG |
| SEQ ID NO: 158 | WT-D25Up | GGEQNPIYWARYADWLFTTPLLLDLLALLVDADEG |
| SEQ ID NO: 159 | WT-D25Down | GGEQNPIYWARYADWLFTTPLLLLLDALLVDADEG |
| SEQ ID NO: 160 | WT-D14Up | GGEQNPIYWARYDAWLFTTPLLLLDLALLVDADEGT |
| SEQ ID NO: 161 | WT-D14Down | GGEQNPIYWARYAWDLFTTPLLLLDLALLVDADEG |
| SEQ ID NO: 162 | WT-P20G | AAEQNPIYWARYADWLFTTGLLLLDLALLVDADEGT |
| SEQ ID NO: 163 | WT-DH | DDDEDNPIYWARYADWLFTTPLLLLHGALLVDAD |
| SEQ ID NO: 164 | WT-2H | DDDEDNPIYWARYAHWLFTTPLLLLHGALLVDADE |
| SEQ ID NO: 165 | WT-L16H | CEQNPIYWARYADWHFTTPLLLLDLALLVDADE |
| SEQ ID NO: 166 | WT-1Wa | AEQNPIYWARYADFLFTTPLLLLDLALLVDADET |
| SEQ ID NO: 167 | WT-1Wb | AEQNPIYFARYADWLFTTPLLLLDLALLVDADE |

TABLE 7-continued

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 168 | WT-1Wc | AEQNPIYFARYADFLFTTPLLLLDLALLWDADET |
| SEQ ID NO: 169 | WT-W6 | ADNNPWIYARYADLTTFPLLLLDLALLVDFDD |
| SEQ ID NO: 170 | WT-W17 | ADNNPFIYARYADLTTWPLLLLDLALLVDFDD |
| SEQ ID NO: 171 | WT-W30 | ADNNPFIYARYADLTTFPLLLLDLALLVDWDD |
| SEQ ID NO: 172 | WT-W17-P7 | ADNNPFPYARYADLTTWILLLLDLALLVDFDD |
| SEQ ID NO: 173 | WT-W39-R11 | ADNNPFIYAYRADLTTFPLLLLDLALLVDWDD |
| SEQ ID NO: 174 | WT-W30-R15 | ADNNPFIYATYADLRTFPLLLLDLALLVDWDD |
| SEQ ID NO: 175 | WT-Rev | Ac-TEDADVLLALDLLLLPTTFLWDAYRAWYPNQEA-Am |
| SEQ ID NO: 176 | Var1-3D | AEDQNPYWARYADWLFTTPLLLLDLALLVD |
| SEQ ID NO: 177 | Var1-1D2E | AEDQNPYWARYADWLFTTPLLLLELALLVE |
| SEQ ID NO: 178 | Var2-3D | AEDQNPYWRAYADLFTPLTLLDLLALWD |
| SEQ ID NO: 179 | Var3-3D | ADDQNPWRAYLDLLFPTDTLLLDLLW |
| SEQ ID NO: 180 | Var3-WT | ADDQNPWRAYLDLLFPTDTLLLDLLWDADE |
| SEQ ID NO: 181 | Var3-Gla2D | ADDQNPWRAYL*Gla*LLFPTDTLLLDLLW |
| SEQ ID NO: 182 | Var3-DGlaD | ADDQNPWRAYLDLLFPT*Gla*TLLLDLLW |
| SEQ ID NO: 183 | Var3-2DGla | ADDQNPWRAYLDLLFPTDTLLL*Gla*LLW |
| SEQ ID NO: 184 | Var3-2GlaD | ADDQNPWRAYL*Gla*LLFPT*Gla*TLLLDLLW |
| SEQ ID NO: 185 | Var3-GlaDGla | ADDQNPWRAYL*Gla*LLFPTDTLLL*Gla*LLW |
| SEQ ID NO: 186 | Var3-D2Gla | ADDQNPWRAYLDLLFPT*Gla*TLLL*Gla*LLW |
| SEQ ID NO: 187 | Var3-3Gla | ADDQNPWRAYL*Gla*LLFPT*Gla*TLLL*Gla*LLW |
| SEQ ID NO: 188 | Var3-Aad2D | ADDQNPWRAYL*Aad*LLFPTDTLLLDLLW |
| SEQ ID NO: 189 | Var3-DAadD | ADDQNPWRAYLDLLFPT*Aad*TLLLDLLW |
| SEQ ID NO: 190 | Var3-2DAad | ADDQNPWRAYLDLLFPTDTLLL*Aad*LLW |
| SEQ ID NO: 191 | Var3-2AadD | ADDQNPWRAYL*Aad*LLFPT*Aad*TLLLDLLW |
| SEQ ID NO: 191 | Var3-AadDAad | ADDQNPWRAYL*Aad*LLFPTDTLLL*Aad*LLW |
| SEQ ID NO: 192 | Var3-D2Aad | ADDQNPWRAYLDLLFPT*Aad*TLLL*Aad*LLW |
| SEQ ID NO: 193 | Var3-3Aad | ADDQNPWRAYL*Aad*LLFPT*Aad*TLLL*Aad*LLW |
| SEQ ID NO: 194 | Var3-GlaAadD | ADDQNPWRAYL*Gla*LLFPT*Aad*TLLLDLLW |
| SEQ ID NO: 195 | Var3-GlaDAad | ADDQNPWRAYL*Gla*LLFPTDTLLL*Aad*LLW |
| SEQ ID NO: 196 | Var3-2GlaAad | **ADDQNPWRAYL*Gla*LLFPT*Gla*TLLL*Aad*LLW** |
| SEQ ID NO: 197 | Var3-AadGlaD | **ADDQNPWRAYL*Aad*LLFPT*Gla*TLLLDLLW** |
| SEQ ID NO: 198 | Var3-AadDGla | **ADDQNPWRAYL*Aad*LLFPTDTLLL*Gla*LLW** |
| SEQ ID NO: 199 | Var3-GlaAadGla | **ADDQNPWRAYL*Gla*LLFPT*Aad*TLLL*Gla*LLW** |
| SEQ ID NO: 200 | Var3-GLL | **GEEQNPWLGAYLDLLFPLELLGLLELGLW** |
| SEQ ID NO: 201 | Var3-M | ADDDDDDPWQAYLDLLFPTDTLLLDLLW |
| SEQ ID NO: 202 | Var4-3E | AEEQNPWRAYLELLFPTETLLLELLW |

TABLE 7-continued

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 203 | Var5-3Da | ADDQNPWARYLDWLFPTDTLLLDL |
| SEQ ID NO: 204 | Var6-3Db | DNNNPWRAYLDLLFPTDTLLLDW |
| SEQ ID NO: 205 | Var7-3E | AEEQNPWARYLEWLFPTETLLLEL |
| SEQ ID NO: 206 | Var7-M | DDDDDDPWQAYLDLFPTDTLALDLW |
| SEQ ID NO: 207 | Var8-3E | EEQQPWAQYLELLFPTETLLLEW |
| SEQ ID NO: 208 | Var9-3E | EEQQPWRAYLELLFPTETLLLEW |
| SEQ ID NO: 209 | Var10-2D | AEDQNPWARYADWLFPTTLLLLD |
| SEQ ID NO: 210 | Var11-2E | AEEQNPWARYAEWLFPTTLLLLE |
| SEQ ID NO: 211 | Var12-1D | AEDQNPWARYADLLFPTTLAW |
| SEQ ID NO: 212 | Var13-1E | AEEQNPWARYAELLFPTTLAW |
| SEQ ID NO: 213 | Var15-2N | DDDDDNPNYWARYANWLFTTPLLLLNGALLVEAEET |
| SEQ ID NO: 214 | Var16-2P | DDDDDNPNYWARYAPWLFTTPLLLLPGALLVEAEET |
| SEQ ID NO: 215 | Var17 | AEQNPIYFARYADFLFTTPLLLLDLALLWDADET |
| SEQ ID NO: 216 | Var18 | AEQNPIYWARYADFLFTTPLLLLDLALLVDADET |
| SEQ ID NO: 217 | Var19a | AEQNPIYWARYADWLFTTPL |
| SEQ ID NO: 218 | Var20 | AEQNPIYFARYADLLFPTTLAW |
| SEQ ID NO: 219 | Var21 | AEQNPIYWARYADLLFPTTLAF |
| SEQ ID NO: 220 | Var22 | AEQNPIYWARYADLLFPTTLAW |
| SEQ ID NO: 221 | Var23 | AEQNPIYFARYADWLFTTPL |
| SEQ ID NO: 222 | Var24 | EDQNPWARYADLLFPTTLAW |
| SEQ ID NO: 223 | ATRAM | GLAGLAGLLGLEGLLGLPLGLLEGLWLGLELEGN |
| SEQ ID NO: 224 | pHLIP ®-CA9 | EQNPIYILDLVFGLLFAVTSVDFLVQWDDAGD |
| SEQ ID NO: 225 | pHLIP ®-Rho | NLEGFFATLGGEIALWSLVVLAIE |
| SEQ ID NO: 226 | pHLIP ®-RhoM1 | NNEGFFATLGGEIALWSDVVLAIE |
| SEQ ID NO: 227 | pHLIP ®-RhoM2 | DNNEGFFATLGGEIPLWSDVVLAIE |

Epitopes may also be delivered to the cell surface of target cells (tumor cells and other diseased tissues/cells) using cyclic pHLIP® peptides. A cyclic peptide is one that comprises a circle geometry or structure. For example, the entire structure of the peptide is circular or a portion of the structure is circular. For example, in the latter case the peptide comprises a cyclic portion and a linear (or tail) portion. In various embodiments, a pH triggered peptide comprises at least 4 amino acids, where (a) at least 2 of the at least 4 amino acids of the peptide are non-polar amino acids, (b) at least 1 of the at least 4 amino acids of the peptide is a protonatable amino acid, and (c) the peptide has a higher affinity to a membrane lipid bilayer at pH 5.0 compared to at pH 8.0. Such pHLIP® peptides are described in International Patent Application No. PCT/US2017/023458 (PCT publication no. WO2017/165452A1, hereby incorporated by reference.

Exemplary cyclic pHLIP® peptides are described and shown below. A lowercase "c" at the beginning of a sequence herein denotes a cyclic peptide (e.g., as in c[(WE) 3WC]) (SEQ ID NO: 1), and a lowercase "1" denotes a linear peptide (e.g., as in 1(CW(EW)4)) (SEQ ID NO: 188). In the case of cyclic structures that comprise a tail, the cyclic portion of the compound is within brackets, and the tail portion follows (is to the right of) the brackets. For example, in the compound c[EsK]WsC, c[EsK] is the cyclic peptide portion, and WsC is the peptide tail portion. As another example, in c[EsK]W4C, the cyclic peptide portion is c[EsK] and the peptide tail portion is W4C.

With respect to cyclic peptides, the amino acids within brackets may be present in the order listed in brackets from left to right, or in any order. For example, a cyclic peptide c[X2Y2] may have the corresponding linear sequence: XXYY, XYXY, YXXY, XYYX, or YXYX. In some cases, multiple examples of corresponding linear sequences for an exemplary cyclic peptide are listed in Table 3.

Table 8 provides a summary of peptide sequences.

TABLE 8 provides a summary of peptide sequences

| Peptide | Sequence | Linear Sequence | SEQ ID NO |
|---|---|---|---|
| 1 | c[(WE)$_3$WC] | WEWEWEWC | 228 |
| 2 | c[(WE)$_4$WC] | WEWEWEWEWC | 229 |
| 3 | c[(WE)$_5$WC] | WEWEWEWEWEWC | 230 |
| 4 | c[(LE)$_4$WC] | LELELELEWC | 231 |

TABLE 8-continued provides a summary of peptide sequences

| Peptide | Sequence | Linear Sequence | SEQ ID NO |
|---|---|---|---|
| 5 | c[E$_4$W$_5$C] | EEEEWWWWWC | 232 |
| 6 | l(CW(EW)$_4$) | CWEWEWEWEW | 233 |
| 7 | c[R$_4$W$_5$C] | RRRRWWWWWC | 234 |

In column 2 ("Sequence", the lower case "c" indicates "circular peptide, and the lower case "l" indicated linear peptide.

Table 9 provides additional non-limiting examples of peptide sequences.

TABLE 9 provides additional non-limiting examples of peptide sequences.

| Cyclic Peptide | Circular Sequence | Linear Sequence | SEQ ID NO |
|---|---|---|---|
| 1 | c[E$_3$W$_5$C] | EEEWWWWWC | 235 |
| 2 | c[E$_3$W$_5$C] | EWEWWWWEC | 236 |
| 3 | c[E$_3$W$_5$C] | EWWEWWWEC | 237 |
| 4 | c[E$_3$W$_5$C] | EWWWEWWEC | 238 |
| 5 | c[E$_3$W$_5$C] | EWWWWEWEC | 239 |
| 6 | c[E$_3$W$_5$C] | EWWWWWEEC | 240 |
| 7 | c[E$_3$W$_5$C] | EWEEWWWWC | 241 |
| 8 | c[E$_3$W$_5$C] | EWWEEWWWC | 242 |
| 9 | c[E$_3$W$_5$C] | EWWWEEWWC | 243 |
| 10 | c[E$_3$W$_5$C] | EWWWWEEWC | 244 |
| 11 | c[E$_3$W$_5$C] | WEEEWWWWC | 245 |
| 12 | c[E$_3$W$_5$C] | WWEEEWWWC | 246 |
| 13 | c[E$_3$W$_5$C] | WWWEEEWWC | 247 |
| 14 | c[E$_3$W$_5$C] | WWWWEEEWC | 248 |
| 15 | c[E$_3$W$_5$C] | WEWEEWWWC | 249 |
| 16 | c[E$_3$W$_5$C] | WEWWEEWWC | 250 |
| 17 | c[E$_3$W$_5$C] | WEWWWEEWC | 251 |
| 18 | c[E$_3$W$_5$C] | WEWWWWEEC | 252 |
| 19 | c[E$_3$W$_5$] | EEEWWWWW | 253 |
| 20 | c[E$_3$W$_5$] | EWEWWWWE | 254 |
| 21 | c[E$_3$W$_5$] | EWWEWWWE | 255 |
| 22 | c[E$_3$W$_5$] | EWWWEWWE | 256 |
| 23 | c[E$_3$W$_5$] | EWWWWEWE | 257 |
| 24 | c[E$_3$W$_5$] | EWWWWWEE | 258 |
| 25 | c[E$_3$W$_5$] | EWEEWWWW | 259 |
| 26 | c[E$_3$W$_5$] | EWWEEWWW | 260 |
| 27 | c[E$_3$W$_5$] | EWWWEEWW | 261 |

TABLE 9-continued provides additional non-limiting examples of peptide sequences.

| Cyclic Peptide | Circular Sequence | Linear Sequence | SEQ ID NO |
|---|---|---|---|
| 28 | c[$E_3W_5$] | EWWWWEEW | 262 |
| 29 | c[$E_3W_5$] | WEEEWWWW | 263 |
| 30 | c[$E_3W_5$] | WWEEEWWW | 264 |
| 31 | c[$E_3W_5$] | WWWEEEWW | 265 |
| 32 | c[$E_3W_5$] | WWWWEEEW | 266 |
| 33 | c[$E_3W_5$] | WEWEEWWW | 267 |
| 34 | c[$E_3W_5$] | WEWWEEWW | 268 |
| 35 | c[$E_3W_5$] | WEWWWEEW | 269 |
| 36 | c[$E_3W_5$] | WEWWWWEE | 270 |
| 37 | c[$D_3W_5C$] | DDDWWWWWC | 271 |
| 38 | c[$D_3W_5C$] | DWDWWWWDC | 272 |
| 39 | c[$D_3W_5C$] | DWWDWWWDC | 273 |
| 40 | c[$D_3W_5C$] | DWWWDWWDC | 274 |
| 41 | c[$D_3W_5C$] | DWWWWDWDC | 275 |
| 42 | c[$D_3W_5C$] | DWWWWWDDC | 276 |
| 43 | c[$D_3W_5C$] | DWDDWWWWC | 277 |
| 44 | c[$D_3W_5C$] | DWWDDWWWC | 278 |
| 45 | c[$D_3W_5C$] | DWWWDDWWC | 279 |
| 46 | c[$D_3W_5C$] | DWWWWDDWC | 280 |
| 47 | c[$D_3W_5C$] | WDDDWWWWC | 281 |
| 48 | c[$D_3W_5C$] | WWDDDWWWC | 282 |
| 49 | c[$D_3W_5C$] | WWWDDDWWC | 283 |
| 50 | c[$D_3W_5C$] | WWWWDDDWC | 284 |
| 51 | c[$D_3W_5C$] | WDWDDWWWC | 285 |
| 52 | c[$D_3W_5C$] | WDWWDDWWC | 286 |
| 53 | c[$D_3W_5C$] | WDWWWDDWC | 287 |
| 54 | c[$D_3W_5C$] | WDWWWWDDC | 288 |
| 55 | c[$D_3W_5$] | DDDWWWWW | 289 |
| 56 | c[$D_3W_5$] | DWDWWWWD | 290 |
| 57 | c[$D_3W_5$] | DWWDWWWD | 291 |
| 58 | c[$D_3W_5$] | DWWWDWWD | 292 |
| 59 | c[$D_3W_5$] | DWWWWDWD | 293 |
| 60 | c[$D_3W_5$] | DWWWWWDD | 294 |
| 61 | c[$D_3W_5$] | DWDDWWWW | 295 |
| 62 | c[$D_3W_5$] | DWWDDWWW | 296 |
| 63 | c[$D_3W_5$] | DWWWDDWW | 297 |

TABLE 9-continued provides additional non-limiting examples of peptide sequences.

| Cyclic Peptide | Circular Sequence | Linear Sequence | SEQ ID NO |
|---|---|---|---|
| 64 | c[$D_3W_5$] | DWWWWDDW | 298 |
| 65 | c[$D_3W_5$] | WDDDWWWW | 299 |
| 66 | c[$D_3W_5$] | WWDDDWWW | 300 |
| 67 | c[$D_3W_5$] | WWWDDDWW | 301 |
| 68 | c[$D_3W_5$] | WWWWDDDW | 302 |
| 69 | c[$D_3W_5$] | WDWDDWWW | 303 |
| 70 | c[$D_3W_5$] | WDWWDDWW | 304 |
| 71 | c[$D_3W_5$] | WDWWWDDW | 305 |
| 72 | c[$D_3W_5$] | WDWWWWDD | 306 |
| 73 | c[$Gla_3W_5$] | GlaGlaGlaWWWWW | 307 |
| 74 | c[$Gla_3W_5$] | GlaWGlaWWWWGla | 308 |
| 75 | c[$Gla_3W_5$] | GlaWWGlaWWWGla | 309 |
| 76 | c[$Gla_3W_5$] | GlaWWWGlaWWGla | 310 |
| 77 | c[$Gla_3W_5$] | GlaWWWWGlaWGla | 311 |
| 78 | c[$Gla_3W_5$] | GlaWWWWWGlaGla | 312 |
| 79 | c[$Gla_3W_5$] | GlaWGlaGlaWWWW | 313 |
| 80 | c[$Gla_3W_5$] | GlaWWGlaGlaWWW | 314 |
| 81 | c[$Gla_3W_5$] | GlaWWWGlaGlaWW | 315 |
| 82 | c[$Gla_3W_5$] | GlaWWWWGlaGlaW | 316 |
| 83 | c[$Gla_3W_5$] | WGlaGlaGlaWWWW | 317 |
| 84 | c[$Gla_3W_5$] | WWGlaGlaGlaWWW | 318 |
| 85 | c[$Gla_3W_5$] | WWWGlaGlaGlaWW | 319 |
| 86 | c[$Gla_3W_5$] | WWWWGlaGlaGlaW | 320 |
| 87 | c[$Gla_3W_5$] | WGlaWGlaGlaWWW | 321 |
| 88 | c[$Gla_3W_5$] | WGlaWWGlaGlaWW | 322 |
| 89 | c[$Gla_3W_5$] | WGlaWWWGlaGlaW | 323 |
| 90 | c[$Gla_3W_5$] | WGlaWWWWGlaGla | 324 |
| 91 | c[$E_3W_4C$] | EEEWWWWC | 325 |
| 92 | c[$E_3W_4C$] | EWEWWWEC | 326 |
| 93 | c[$E_3W_4C$] | EWWEWWEC | 327 |
| 94 | c[$E_3W_4C$] | EWWWEWEC | 328 |
| 95 | c[$E_3W_4C$] | EWWWWEEC | 329 |
| 96 | c[$E_3W_4C$] | EWEEWWWC | 330 |
| 97 | c[$E_3W_4C$] | EWWEEWWC | 331 |
| 98 | c[$E_3W_4C$] | EWWWEEWC | 332 |
| 99 | c[$E_3W_4C$] | EWWWWEEC | 333 |
| 100 | c[$E_3W_4C$] | WEEEWWWC | 334 |

TABLE 9-continued provides additional non-limiting examples of peptide sequences.

| Cyclic Peptide | Circular Sequence | Linear Sequence | SEQ ID NO |
|---|---|---|---|
| 101 | c[$E_3W_4C$] | WWEEEWWC | 335 |
| 102 | c[$E_3W_4C$] | WWWEEEWC | 336 |
| 103 | c[$E_3W_4C$] | WWWWEEEC | 337 |
| 104 | c[$E_3W_4C$] | WEWEEWWC | 338 |
| 105 | c[$E_3W_4C$] | WEWWEEWC | 339 |
| 106 | c[$E_3W_4C$] | WEWWWEEC | 340 |
| 107 | c[$E_3W_4$] | EEEWWWW | 341 |
| 108 | c[$E_3W_4$] | EWEWWWE | 342 |
| 119 | c[$E_3W_4$] | EWWEWWE | 343 |
| 110 | c[$E_3W_4$] | EWWWEWE | 344 |
| 111 | c[$E_3W_4$] | EWWWWEE | 345 |
| 112 | c[$E_3W_4$] | EWEEWWW | 346 |
| 113 | c[$E_3W_4$] | EWWEEWW | 347 |
| 114 | c[$E_3W_4$] | EWWWEEW | 348 |
| 115 | c[$E_3W_4$] | EWWWWEE | 349 |
| 116 | c[$E_3W_4$] | WEEEWWW | 350 |
| 117 | c[$E_3W_4$] | WWEEEWW | 351 |
| 118 | c[$E_3W_4$] | WWWEEEW | 352 |
| 119 | c[$E_3W_4$] | WWWWEEE | 353 |
| 120 | c[$E_3W_4$] | WEWEEWW | 354 |
| 121 | c[$E_3W_4$] | WEWWEEW | 355 |
| 122 | c[$E_3W_4$] | WEWWWEE | 356 |
| 123 | c[$D_3W_4C$] | DDDWWWWC | 357 |
| 124 | c[$D_3W_4C$] | DWDWWWDC | 358 |
| 125 | c[$D_3W_4C$] | DWWDWWDC | 359 |
| 126 | c[$D_3W_4C$] | DWWWDWDC | 360 |
| 127 | c[$D_3W_4C$] | DWWWWDDC | 361 |
| 128 | c[$D_3W_4C$] | DWDDWWWC | 362 |
| 129 | c[$D_3W_4C$] | DWWDDWWC | 363 |
| 130 | c[$D_3W_4C$] | DWWWDDWC | 364 |
| 131 | c[$D_3W_4C$] | DWWWWDDC | 365 |
| 132 | c[$D_3W_4C$] | WDDDWWWC | 366 |
| 133 | c[$D_3W_4C$] | WWDDDWWC | 367 |
| 134 | c[$D_3W_4C$] | WWWDDDWC | 368 |
| 135 | c[$D_3W_4C$] | WWWWDDDC | 369 |
| 136 | c[$D_3W_4C$] | WDWDDWWC | 370 |

TABLE 9-continued provides additional non-limiting examples of peptide sequences.

| Cyclic Peptide | Circular Sequence | Linear Sequence | SEQ ID NO |
|---|---|---|---|
| 137 | c[$D_3W_4C$] | WDWWDDWC | 371 |
| 138 | c[$D_3W_4C$] | WDWWWDDC | 372 |
| 139 | c[$D_3W_4$] | DDDWWWW | 373 |
| 140 | c[$D_3W_4$] | DWDWWWD | 374 |
| 141 | c[$D_3W_4$] | DWWDWWD | 375 |
| 142 | c[$D_3W_4$] | DWWWDWD | 376 |
| 143 | c[$D_3W_4$] | DWWWWDD | 377 |
| 144 | c[$D_3W_4$] | DWDDWWW | 378 |
| 145 | c[$D_3W_4$] | DWWDDWW | 379 |
| 146 | c[$D_3W_4$] | DWWWDDW | 380 |
| 147 | c[$D_3W_4$] | DWWWWDD | 381 |
| 148 | c[$D_3W_4$] | WDDDWWW | 382 |
| 149 | c[$D_3W_4$] | WWDDDWW | 383 |
| 150 | c[$D_3W_4$] | WWWDDDW | 385 |
| 151 | c[$D_3W_4$] | WWWWDDD | 386 |
| 152 | c[$D_3W_4$] | WDWDDWW | 387 |
| 153 | c[$D_3W_4$] | WDWWDDW | 388 |
| 154 | c[$D_3W_4$] | WDWWWDD | 399 |
| 155 | c[$Gla_3W_4$] | GlaGlaGlaWWWW | 400 |
| 156 | c[$Gla_3W_4$] | GlaWGlaWWWGla | 401 |
| 157 | c[$Gla_3W_4$] | GlaWWGlaWWGla | 402 |
| 158 | c[$Gla_3W_4$] | GlaWWWGlaWGla | 403 |
| 159 | c[$Gla_3W_4$] | GlaWWWWGlaGla | 404 |
| 160 | c[$Gla_3W_4$] | GlaWGlaGlaWWW | 405 |
| 161 | c[$Gla_3W_4$] | GlaWWGlaGlaWW | 406 |
| 162 | c[$Gla_3W_4$] | GlaWWWGlaGlaW | 407 |
| 163 | c[$Gla_3W_4$] | GlaWWWWGlaGla | 408 |
| 164 | c[$Gla_3W_4$] | WGlaGlaGlaWWW | 409 |
| 165 | c[$Gla_3W_4$] | WWGlaGlaGlaWW | 410 |
| 166 | c[$Gla_3W_4$] | WWWGlaGlaGlaW | 411 |
| 167 | c[$Gla_3W_4$] | WWWWGlaGlaGla | 412 |
| 168 | c[$Gla_3W_4$] | WGlaWGlaGlaWW | 413 |
| 169 | c[$Gla_3W_4$] | WGlaWWGlaGlaW | 414 |
| 170 | c[$Gla_3W_4$] | WGlaWWWGlaGla | 415 |
| 171 | c[$(WE)_3WC$] | WEWEWEWC | 416 |
| 172 | c[$(EW)_3WC$] | EWEWEWWC | 417 |
| 173 | c[$(WD)_3WC$] | WDWDWDWC | 418 |

TABLE 9-continued provides additional non-limiting examples of peptide sequences.

| Cyclic Peptide | Circular Sequence | Linear Sequence | SEQ ID NO |
|---|---|---|---|
| 174 | c[$(DW)_3$WC] | DWDWDWWC | 419 |
| 175 | c[$(WGla)_3$WC] | WGlaWGlaWDWC | 420 |
| 176 | c[$(GlaW)_3$WC] | DWDWDWDC | 421 |
| 177 | c[$(WE)_4$] | WEWEWEWE | 422 |
| 178 | c[$(EW)_4$] | EWEWEWEW | 423 |
| 179 | c[$(WD)_4$] | WDWDWDWD | 424 |
| 180 | c[$(DW)_4$] | DWDWDWDW | 425 |
| 181 | c[$(WGla)_4$] | WGlaWGlaWGlaWGla | 426 |
| 182 | c[$(GlaW)_4$] | GlaWGlaWGlaWGlaW | 427 |
| 183 | c[CW$(EW)_4$] | CWEWEWEWEW | 428 |
| 184 | c[$(WGla)_2$WDWC] | WGlaWGlaWDWC | 429 |
| 185 | c[$(EW)_3$EC] | EWEWEWEC | 430 |
| 186 | c[$(DW)_3$DC] | DWDWDWDC | 431 |
| 187 | c[$E_5$K]$W_5$C | Cyclic: EEEEEK<br>Tail: WWWWWC | 432 (cyclic portion),<br>433 (Tail) |
| 188 | c[$E_4$K]$W_5$C | Cyclic: EEEEK<br>Tail: WWWWWC | 434 (cyclic portion),<br>435 (Tail) |
| 189 | c[$E_5$K]$W_4$C | Cyclic: EEEEEK<br>Tail: WWWWC | 436 (cyclic portion),<br>437 (Tail) |
| 190 | c[$E_4$K]$W_4$C | Cyclic: EEEEK<br>Tail: WWWWC | 438 (cyclic portion),<br>439 (Tail) |
| 191 | c[$E_5$K]$W_5$ | Cyclic: EEEEEK<br>Tail: WWWWW | 440 (cyclic portion),<br>441 (Tail) |
| 192 | c[$E_4$K]$W_5$ | Cyclic: EEEEK<br>Tail: WWWWW | 442 (cyclic portion),<br>443 (Tail) |
| 193 | c[$E_5$K]$W_4$ | Cyclic: EEEEEK<br>Tail: WWWW | 444 (cyclic portion),<br>445 (Tail) |
| 194 | c[$E_4$K]$W_4$ | Cyclic: EEEEK<br>Tail: WWWW | 446 (cyclic portion),<br>447 (Tail) |
| 195 | c[$D_5$K]$W_5$C | Cyclic: DDDDDK<br>Tail: WWWWWC | 448 (cyclic portion),<br>449 (Tail) |
| 196 | c[$D_4$K]$W_5$C | Cyclic: DDDDK<br>Tail: WWWWWC | 450 (cyclic portion),<br>451 (Tail) |
| 197 | c[$D_5$K]$W_4$C | Cyclic: DDDDDK<br>Tail: WWWWC | 452 (cyclic portion),<br>453 (Tail) |
| 198 | c[$D_4$K]$W_4$C | Cyclic: DDDDK<br>Tail: WWWWC | 454 (cyclic portion),<br>455 (Tail) |
| 199 | c[$D_5$K]$W_5$ | Cyclic: DDDDDK<br>Tail: WWWWW | 456 (cyclic portion),<br>457 (Tail) |
| 200 | c[$D_4$K]$W_5$ | Cyclic: DDDDK<br>Tail: WWWWW | 458 (cyclic portion),<br>459 (Tail) |
| 201 | c[$D_5$K]$W_4$ | Cyclic: DDDDDK<br>Tail: WWWW | 460 (cyclic portion),<br>461 (Tail) |

TABLE 9-continued provides additional non-limiting examples of peptide sequences.

| Cyclic Peptide | Circular Sequence | Linear Sequence | SEQ ID NO |
|---|---|---|---|
| 202 | c[$D_4$K]$W_4$ | Cyclic: DDDDK Tail: WWWW | 462 (cyclic portion), 463 (Tail) |
| 203 | c[$Gla_5$K]$W_5$C | Cyclic: GlaGla GlaGlaGlaK Tail: WWWWWC | 464 (cyclic portion), 465 (Tail) |
| 204 | c[$Gla_4$K]$W_5$C | Cyclic: GlaGla GlaGlaK Tail: WWWWWC | 466 (cyclic portion), 467 (Tail) |
| 205 | c[$Gla_5$K]$W_4$C | Cyclic: GlaGla GlaGlaGlaK Tail: WWWWC | 468 (cyclic portion), 469 (Tail) |
| 206 | c[$Gla_4$K]$W_4$C | Cyclic: GlaGla GlaGlaK Tail: WWWWC | 470 (cyclic portion), 471 (Tail) |
| 207 | c[$Gla_5$K]$W_5$ | Cyclic: GlaGla GlaGlaGlaK Tail: WWWWW | 472 (cyclic portion), 473 (Tail) |
| 208 | c[$Gla_4$K]$W_5$ | Cyclic: GlaGla GlaGlaK Tail: WWWWW | 474 (cyclic portion), 475 (Tail) |
| 209 | c[$Gla_5$K]$W_4$ | Cyclic: GlaGla GlaGlaGlaK Tail: WWWW | 476 (cyclic portion), 477 (Tail) |
| 210 | c[$Gla_4$K]$W_4$ | Cyclic: GlaGla GlaGlaK Tail: WWWW | 478 (cyclic portion), 479 (Tail) |
| 211 | c[$E_5W_5$C] | EEEEEWWWWWC | 480 |
| 212 | c[$E_4W_4$C] | EEEEWWWWC | 481 |
| 213 | c[$(WE)_4$CW] | WEWEWEWECW | 482 |
| 214 | c[$(WR)_4$WC] | WRWRWRWRWC | 483 |

Production of Epitope-pHLIP® Peptide Compositions

To manufacture the constructs or compositions to decorate the cell surfaces of diseased cell, a variety of methods known in the art can be used, e.g.:

i) epitope synthesized and linked to the membrane non-inserting part of pHLIP® peptide; or ii) epitope synthesized as membrane non-inserting part of pHLIP® as a single peptide; or iii) epitope expressed as membrane non-inserting part of pHLIP® fusion protein.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Tethering Small Molecule Epitope Di-Nitrophenyl (DNP) to Cancer Cells by pHLIP® Promoted Cell Killing Three different pHLIP® constructs were synthesized with a DNP—(0-(2,4-dinitrophenyl)hydroxylamine):

i) DNP-pHLIP®, where DNP-malemide was conjugated with a single Cys residue at the N-terminal of the pHLIP® peptide;

ii) DNP-PEG4-pHLIP®, where DNP-PEG4-NHS was conjugated with a single Lys residue at the N-terminal of the pHLIP® peptide; and iii) DNP-PEG12-pHLIP®, where DNP-PEG12-NHS as conjugated with a single Lys residue at the N-terminal of pHLIP® peptide.

pHLIP® peptide with a single Cys residues used in the study for conjugation with DNP-malemide is the following: (ACDDQNPWRAYLDLLFPTDTLLLDLLWA (SEQ ID NO: 509) pHLIP® peptide with single Lys residue and acetylated N-terminus used in the study for conjugation with DNP-PEG4-NHS and DNP-PEG12-NHS is the following: Ac-AKDDQNPWRAYLDLLFPTDTLLLDLLWA (SEQ ID NO: 510)). Peptides were prepared by solid-phase synthesis. Progressions of coupling reactions and purifications were performed using reverse-phase HPLC (RP-HPLC) (the gradient: water and acetonitrile with 0.05% trifluoroacetic acid (TFA) followed by lyophilization. The purity and identity of the constructs were established by analytical RP-HPLC and surface-enhanced laser desorption/ionization time of flight (SELDI-TOF) mass spectroscopy, respectively. Constructs concentrations were calculated by absorbance at 280 nm using pHLIP® peptide extinction coefficient.

The key for induction of immunological response is a proper positioning of epitope at the surface of tumor cells, which was verified on 3-D tumor cancer cell culture (tumor spheroids). Briefly, a 2% agarose solution was made by dissolving in pH 7.4 PBS. 150 μL of the solution was pipetted into each well of a 48-well flat bottom tissue culture plate. After the agarose gel sufficiently settled (~1 h), 150 μL of DMEM supplemented with 10% FBS and ciprofloxacin-HCl was added to each well. The covered plate was left in a humidified atmosphere at 37° C. and 5% $CO_2$ in cell culture incubator for 24 h. On the next day, the excess medium was removed from the agarose layer. HeLa cells (10,000 cells) in 200 μL of DMEM containing 2% matrigel were added into each well and incubated for 3-4 days to allow the formation of spheroids. Matrigel was dissolved on ice overnight and added in ice cold DMEM at a concentration of 2.5% (to obtain a final concentration of 2% once added to the wells). Then the mixture was heated to 37° C. before being combined with the cells. Tumor spheroids were incubated in 50 μL of PBS buffer, pH 6.0-6.5 containing 0-2 μM DNP-pHLIP®, DNP-PEG4-pHLIP® or DNP-PEG12-pHLIP® in a humidified atmosphere of 5% $CO_2$ at 37° C. for 30 min. After treatment, the spheroids were washed several times in 1 mL of PBS. Next, spheroids were treated with anti-DNP antibody labeled with 647 nm fluorescent dye at pH 7.4 followed by washing. Spheroids were also stained with DAPI to mark cell nucleus.

Figure 6:
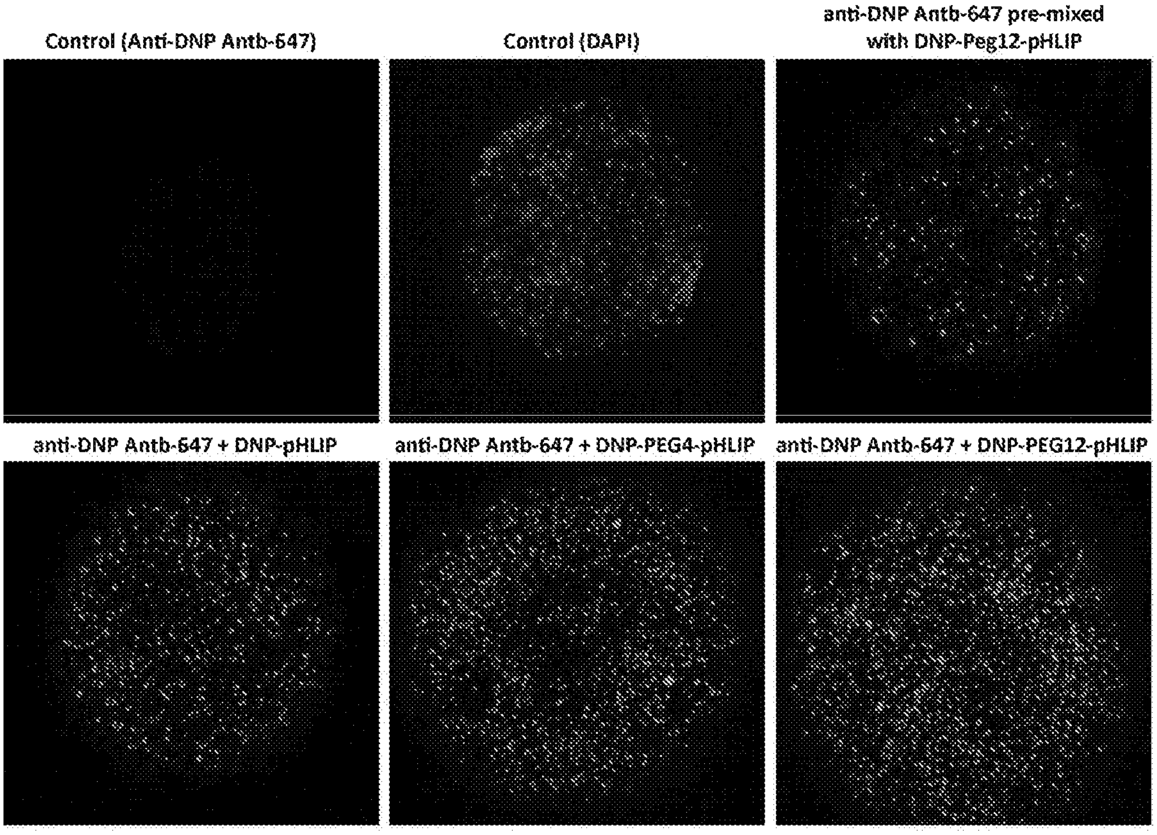
FIG. 6 depict fluorescent (647 nm) images obtained on tumor spheroids treated with an anti-DNP fluorescent antibody, DAPI, or an anti-DNP fluorescent antibody pre-mixed with DNP-PEG12-pHLIP® construct followed by washing and imaging (upper raw), and treated with DNP-pHLIP®, DNP-PEG4-pHLIP® D or DNP-PEG12-pHLIP® first, washed, and then treated with anti-DNP fluorescent antibody followed by washing and imaging of spheroids (bottom raw).

The spheroids were imaged using a fluorescent inverted confocal microscope. The representative images are shown in FIG. 6. The data clearly indicate that pHLIP® peptide positioned DNP epitope at the surface of cancer cells in 3-D cell culture, and the epitope was recognized by the corresponding antibody.

Figure 7:
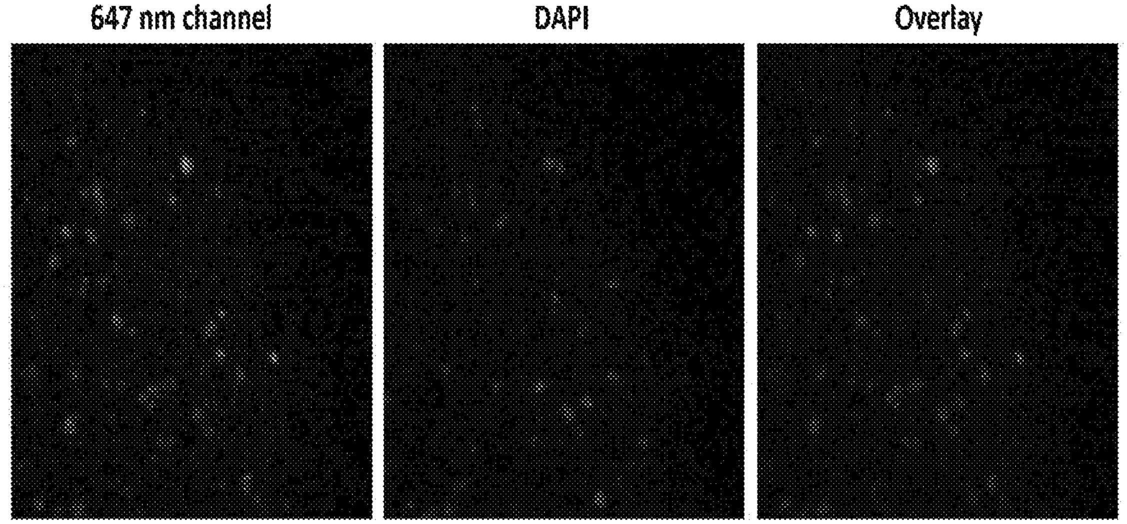
FIG. 7 depict fluorescent images obtained on tumor spheroids treated with DNP-PEG12-pHLIP® first, washed, and then treated with anti-DNP fluorescent antibody and DAPI, washing and imaging of tumor spheroids at different channels using an inverted confocal microscope and 40× objective.

Images presented in FIG. 7 were obtained at high magnification to demonstrate that fluorescent signal from the antibody coincided with the fluorescent signal from DAPI, which stains DNA in cell nucleus. There were multiple focal planes in 3-D tumor spheroid and focus for DAPI signal and 647 nm fluorescent light were different, however an overlay between fluorescence from the antibody and DAPI fluorescence is clearly observed.

Figure 8:
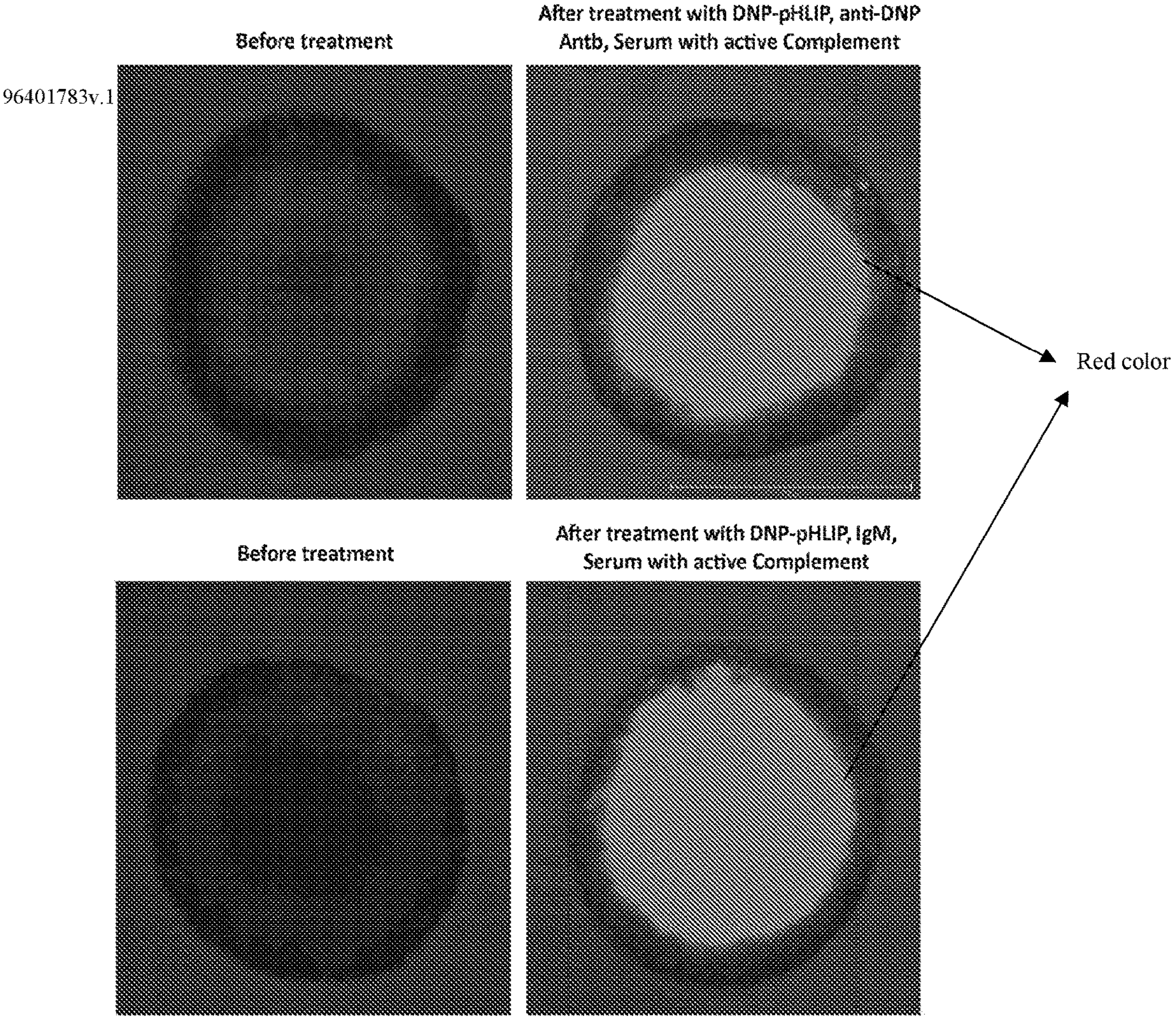
FIG. 8 depicts a representative overlay of fluorescent and brightfield images of tumor spheroids treated with DNP-PEG12-pHLIP®, washed, then treated with anti-DNP antibody or IgM followed by addition of human serum with active complement and PI fluorescent dye, followed by washing and imaging. The images were obtained 2 hours after the treatment.

To establish a biological effect, the tumor speroids were treated with 5 sM of DNP-pHLIP®, DNP-PEG4-pHLIP® or DNP-PEG12-pHLIP® for 1 hour in PBS pH6.5, washed followed by incubation with anti-DNP antibody or human IgM antibody for 1 hr in PBS pH7.4. Then human serum with active complement and propidium iodine (PI) were added, washed and spheroids were imaged. Cell impermeable PI dye stains only dead (or dying) cells with the compromised membrane. Therefore presence of red color on FIG. 8 indicated that plasma membrane of cells was comrpomized by complement-mediated attack and that the cells were dying.

Figure 5A:
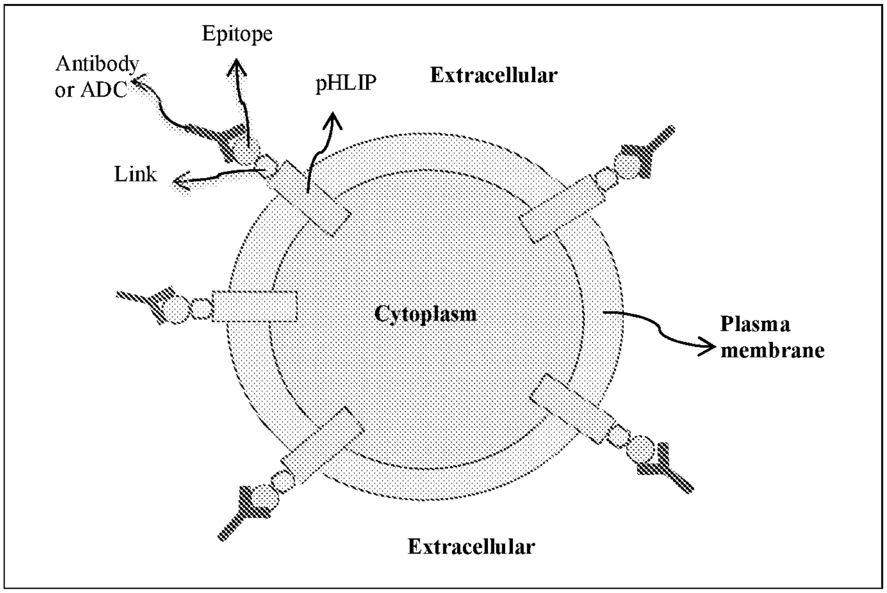
FIG. 5A is a schematic presentation of epitope tethered to the surface of cell by pHLIP®. As a result, the targeted cell becomes decorated with epitopes and endogenous (natural) antibodies, exogenous antibodies, ADCs administrated into body, antibodies which are produced (generated) in the course of vaccination, and bind the targeted cell to promote cell killing.
Figure 5B:
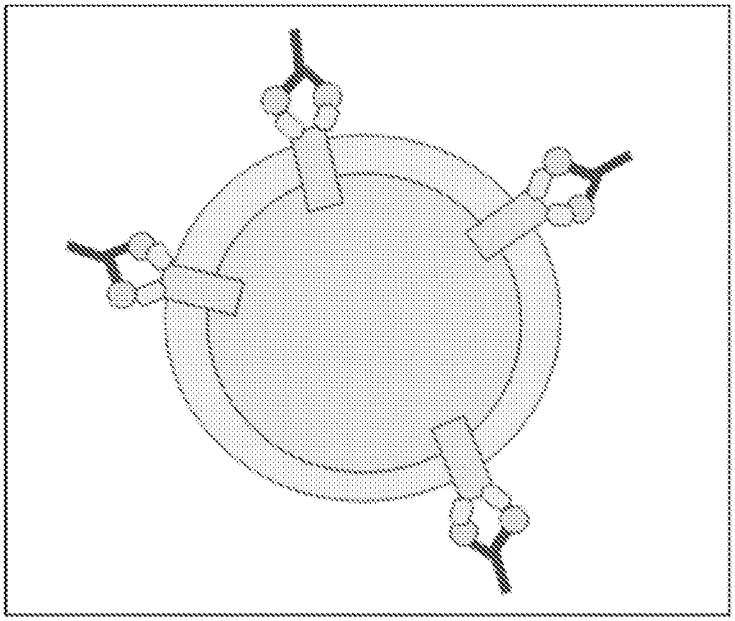
FIG. 5B is a schematic presentation of two epitopes tethered to the surface of cell by pHLIP® to bind two heads of one antibody molecule. As a result, the targeted cell becomes decorated with epitopes and endogenous (natural) antibodies, or exogenous antibodies, or ADCs administrated into body, or antibodies, which are produced (generated) in the course of vaccination bind targeted cell to promote cell killing.

Example 2: Tethering Two Peptide Epitopes by pHLIP® to Cancer Cells to Bind Two Heads of Ig Antibody To enhance performance of antibodies and enhance immune response, it is important to promote binding of both heads of IgG with 2 epitopes coupled to the same pHLIP® peptide (see, e.g., FIG. 5B). The pHLIP® peptide with 2 Lys residues (bold and underlined) (Ac-AKQNDDQNKP-WRAYLDLLFPTDTLLLDLLWA (SEQ ID NO: 511)) is conjugated with excess of NHS-PEG12-malemide and NHS-PEG24-malemide linkers, purified and, pHLIP-(PEG12)2 is coupled with an HA peptide epitope (YPYDVPDYAGGGCA (SEQ ID NO: 6)). pHLIP® and HA peptides are prepared by solid-phase synthesis. Progressions of both coupling reactions and purifications are performed using reverse-phase HPLC (RP-HPLC) (the gradient: water and acetonitrile with 0.05% TFA) followed by lyophilization. The concentration of the construct is measured by absorbance at 280 nm.

PEG12 and PEG24 are be stretched for 5 nm and 10 nm, respectively. The six residues (QNDDQN (SEQ ID NO: 541)) between points of PEG conjugation to pHLIP® provides additional space of few nanometers, for example, from 5 to 25 nm, or, from about 10-15 nm. Thus, two epitopes at the single pHLIP® construct bind two heads of Ig antibody, since the distance between heads is 10-15 nm.

HeLa cancer cells in 2D and 3D cell culture are stained with (HA)2-(PEG12)2-pHLIP®, $(HA)_2$-(PEG24)2-pHLIP®, HA-PEG12-pHLIP® and HA-PEG24-pHLIP®. Affinity of fluorescent antibody against HA peptide epitope is evaluated.

Example 3: Tethering CXCL10 Protein Chemokine Epitope by pHLIP® to Cancer Cells to Promote NK-Cells Binding Two fusion proteins with 2 different tags (His and cMyc) are expressed and purified:

CXCL10-mucin-2×-Myc-pHLIP®

```
                                  SEQ ID NO: 531
mnqtailicclifltlsgiqgvplsrtvrctcisisnqpvnprslekleii

pasqfcprveiiatmkkkgekrclnpeskaiknllkavskerskrspgtfe

kqigevkprttpaaggmdesvvlepeatgesssleptpssqeaqralgtsp

elptgvtgssgtrlpptpkaqdggpvgtelfrvppvstaatwqssaphqpg

pslwaeaktseapstqdpstqastasspapeenapsegqrvwgqgqsprpe

nslereemgpvpahtdafqdwgpgsmahvsvvpvssegtpsrepvasgswt

pkaeepihatmdpqrlgvlitpvpdaqaatrrqeqkliseedleqklisee

dladdqnpwrayidllfptdtllldllw
```

CXCL10-mucin-6×-His-pHLIP®

```
                                  SEQ ID NO: 532
mnqtailicclifltlsgiggvplsrtvrctcisisnqpvnprslekleii

pasqfcprveiiatmkkkgekrclnpeskaiknllkavskerskrspgtfe

kqigevkprttpaaggmdesvvlepeatgesssleptpssqeagralgtsp

elptgvtgssgtrlpptpkaqdggpvgtelfrvppvstaatwqssaphqpg

pslwaeaktseapstqdpstqastasspapeenapsegqrvwgqgqsprpe

nslereemgpvpahtdafqdwgpgsmahvsvvpvssegtpsrepvasgswt

pkaeepihatmdpqrlgvlitpvpdagaatrrqhhhhhhaddqnpwrayld

llfptdtllldllw
```

Both fusion proteins are treated with HeLa or HeLa-GFP cancer cells at pH 6.0-6.5 followed by washing and applying NK-cells loaded with red fluorescent dye DiI (1,1'-dioctadecyl-3,3,3',3'-tetramethylindocarbocyanine) for 30 min followed by gentle washing. Binding and adhesion of NK-cells to cancer cells decorated with CXCL10 chemokine pHLIP® constructs and non-decorated are compared under fluorescent microscope by analyzing green and red fluorescent signals coming from cancer cells and immune NK-cells, respectively.

pHLIP® Peptide-Mediated Epitope Tethering at Cell Surfaces: Summary I

The invention features compositions and methods for eliciting an immune response in a subject by administering to the subject a pHLIP® construct comprising an antibody recruiting molecule or an immune cell recruiting molecule. The antibody recruiting molecule or an immune cell recruiting molecule is linked to one or more pHLIP® peptides and wherein The construct increases the amount of antibody recruiting molecule or immune cell recruiting molecule on the surface of a diseased cell.

For example, the composition comprises the formula of:

Epitope-Linker-Pept

- wherein "Epitope" is an antibody or immune cell recruiting molecule;
- wherein "Linker" is a non-cleavable linker compound or a membrane non-inserting end of the pHLIP® peptide further comprises an amino acid extension;
- wherein "Pept" is a pHLIP® peptide comprising the sequence AXDDQNPWRAYLDLLFPTDTLLLDLLW (SEQ ID NO: 533) or AXDQDNPWRAYLDLLFPTDTLLLDLLW (SEQ ID NO: 534), where "X" is a functional group, selected from a lysine, a cysteine, or an Azido-containing amino acid;
- wherein each "—" is a covalent bond;

In some examples, the construct comprises an antibody recruiting molecule; in other examples, the construct comprises an immune cell recruiting molecule. Optionally, the construct comprises both an antibody recruiting molecule or an immune cell recruiting molecule In some embodiments, 2 antibody recruiting molecules are linked to pHLIP® peptide. Such an exemplary construct and method is described below. For example, the composition or method includes a construct that comprises the formula of Epitope1-Linker-Pept-Linker-Epitope1

- wherein "Epitope1" is an antibody recruiting molecule;
- wherein "Linker" is a polyethylene glycol linker;
- wherein "Pept" is a pHLIP® peptide comprising the sequence

```
                                        (SEQ ID NO: 511)
Ac-AKQNDDQNKPWRAYLDLLFPTDTLLLDLLWA
or
                                        (SEQ ID NO: 535)
Ac-AKQNDNDNKPWRAYLDLLFPTDTLLLDLLWA
or
                                        (SEQ ID NO: 536)
ACQNDDQNCPWRAYLDLLFPTDTLLLDLLWA
or
                                        (SEQ ID NO: 505)
ACQNDNDNCPWRAYLDLLFPTDTLLLDLLWA
```

wherein each "—" is a covalent bond.

As described above, exemplary recruiting molecules include one or more epitopes. For example, the epitope comprises a peptide with a length less than 50 amino acids.

The method of claim 1, wherein said antibody recruiting molecule or immune cell recruiting molecule comprises an epitope. In examples, the epitope comprises a peptide with a length less than 50 amino acids, e.g., the epitope comprises a length of between 5 to 20 amino acids. An exemplary epitope comprises an HA peptide. For example, the peptide comprises the amino acid sequence of YPYDVPDYA (SEQ ID NO: 6). Additional examples of epitopes include QVSHWVSGLAEGSFG (SEQ ID NO: 1), LSHTSGRVEGSVSLL (SEQ ID NO: 2), QMWAPQWGPD (SEQ ID NO: 3); MASMTGGQQMG (SEQ ID NO: 4); EQKLISEEDL (SEQ ID NO: 5); YTDIEMNRLGK (SEQ ID NO: 7); KETAAAKFERQHMDS (SEQ ID NO: 8); GKPIPNPLLGLDST (SEQ ID NO: 9); DYKDDDDK (SEQ ID NO: 10); GAPVPYPDPLEPR (SEQ ID NO: 11); HHHHHH (SEQ ID NO: 12); TKENPRSNQEESYDDNES (SEQ ID NO: 13); WSHPQFEK (SEQ ID NO: 14); or PDRVRAVSHWSS (SEQ ID NO: 15).

In examples, an epitope comprises a protein epitope with a length of 200 or less amino acids. For example, the protein epitope comprises a cytokine such as an interleukin (IL), e.g., IL-1, IL-2, IL-6, IL-7, IL-12, or IL-17. In some embodiments, the cytokine comprises tumor necrosis factor (TNF). In some some embodiments, the cytokine comprises a chemokine (CXC). Examples of chemokines include CXCL9, CXL10, or CXL11. For example, the chemokine comprises CXCL10 comprises the amino acid sequence:

```
                                        (SEQ ID NO: 514)
MNQTAILICCLIFLTLSGIQGVPLSRTVRCTCISISNQPVNPRSLEKLEII

PASQFCPRVEIIATMKKKGEKRCLNPESKAIKNLLKAVSKERSKRSP.
```

In yet other examples, the epitope comprises a small molecule. For example, the small molecule comprises a dinitrophenyl (DNP) or a derivative thereof.

The methods are useful to methods for eliciting an immune response in a subject. This clinically beneficial effect is accomplished by the pHLIP® construct that increases the amount of antibody recruiting molecule or immune cell recruiting molecule on the surface of a diseased cell. For example, the diseased cell comprises a tumor cell. In another example, the diseased cell comprises a cell in inflamed tissue.

Also within the invention is a composition comprising an antibody or immune cell recruiting molecule linked to one or more pHLIP® peptides by a non-cleavable linker compound. A composition comprising an epitope linked to one or more pHLIP® peptides, wherein the epitope is a protein epitope and is an extension of the non-inserting end of the pHLIP® peptide is also within the invention. For example, the non-inserting end of the pHLIP® peptide further comprises an amino acid extension, wherein the extension comprises a protein epitope. In another aspect, the invention encompasses a composition comprising an epitope linked to one or more pHLIP® peptides, wherein the epitope and the pHLIP® peptide are part of a single fusion construct.

In the methods or compositions, the pHLIP® construct comprises the formula of Epitope-Linker-Peptide, wherein Peptide is a pHLIP® peptide comprising the sequence AXDDQNPWRAYLDLLFPTDTLLLDLLWA (SEQ ID NO: 18) or AXDQDNPWRAYLDLLFPTDTLLLDLLWA (SEQ ID NO: 495), where "X" is a functional group, selected from a lysine, a cysteine, or an Azido-containing amino acid, wherein Linker is a linker or an extension of the pHLIP® peptide, and wherein each "—" is a covalent bond.

An exemplary composition comprises the formula of Epitope-Linker-Peptide, wherein Peptide is a pHLIP® peptide comprising the sequence AXDDQNPWRAYLDLL-FPTDTLLLDLLWA (SEQ ID NO: 18) or AXDQDNP-WRAYLDLLFPTDTLLLDLLWA (SEQ ID NO: 495, where X is a functional group, selected from a lysine, a cysteine, or an Azido-containing amino acid, and wherein Linker is a linker or an extension of the pHLIP® peptide, and wherein each "—" is a covalent bond. In some examples, two epitopes are linked to a single pHLIP® peptide.

As described above, the construct may comprise the formula of Epitope2-Linker2-Peptide, wherein Peptide is a pHLIP® peptide comprising the sequence AX(Z)nXP-WRAYLDLLFPTDTLLLDLLWA (SEQ ID NO: 496), wherein X is a functional group, selected from a lysine, a cysteine, an Azido-containing amino acid, or others, wherein Z comprises indicates any amino acid residue, wherein n is any integer between 1 and 10, wherein Linker is a linker or an extension of the pHLIP® peptide, and each "—" is a covalent bond. In another example, the composition or construct comprises the formula of Epitope2-Linker2-Pept, wherein "Pept" is a pHLIP® peptide comprising the sequence AX(Z)nXPWRAYLDLLFPTDTLLLDLLWA (SEQ ID NO: 496), where X is a functional group, selected from a lysine, a cysteine, an Azido-containing amino acid, wherein Z indicates any amino acid residue, wherein n is any integer between and including 1 and 10, wherein Linker is a linker or an extension of the pHLIP® peptide, and wherein each "—" is a covalent bond.

A method of inducing an immune response in a diseased tissue in a subject, which method comprises the step of administering to a subject a composition comprising an epitope and a pHLIP® peptide is also within the invention. For example, the subject comprises a solid tumor or the subject comprises an inflamed tissue. The pHLIP® compositions or constructs are administered in a variety of clinically-acceptable methods, e.g, the composition is injected directly into a diseased tissue tumor mass. In another example, the composition is systemically administered. The method is associated with numerous advantages, e.g., the biological effect of the composition in eliciting or promoting an antigen-specific (epitope-specific) immune response is at least 20% greater than that delivered in the absence of said composition. The response may be at least 25, 50, 75, 90% and even 2-fold, 3-fold, 5-fold, 10-fold or more greater than that delivered in the absence of pHLIP® composition or construct. Another significant advantage is that the composition targets preferentially to a diseased tissue compared to a healthy tissue, thereby minimizing damage to said healthy tissue.

Also within the invention is a method for promoting an immune response in a subject, comprising administering to a subject the pHLIP® compositions and constructs described herein, wherein the method comprises placement of the epitope on tumor cell or a cell in inflamed tissue of said subject.

pHLIP® Peptide-Mediated Epitope Tethering at Cell Surfaces: Summary II

Exemplary pHLIP® compositions comprise an epitope and a pHLIP® peptide.

In one example, the composition comprises the formula of

Epitope-Linker-Pept wherein "Epitope" is an antibody or immune cell recruiting molecule;

wherein "Linker" is a non-cleavable linker compound or a membrane non-inserting end of the pHLIP® peptide further comprises an amino acid extension;

wherein "Pept" is a pHLIP® peptide comprising the sequence AXDDQNPWRAYLDLLFPTDTLLLDLLW (SEQ ID NO: 533) or AXDQDNPWRAYLDLL-FPTDTLLLDLLW (SEQ ID NO: 534), where "X" is a functional group, selected from a lysine, a cysteine, or an Azido-containing amino acid;

wherein each "—" is a covalent bond.

Antibody Recruitment

In preferred embodiments, the epitope is an antibody recruiting molecule. For example, 2 antibody recruiting molecules are linked to pHLIP® peptide. An example of such a composition for recruiting antibodies includes a composition comprising the formula of Epitope1-Linker-Pept-Linker-Epitope1 wherein "Epitope1" is an antibody recruiting molecule;

wherein "Linker" is a polyethylene glycol linker;

wherein "Pept" is a pHLIP® peptide comprising the sequence (SEQ ID NO: 511)
Ac-AKQNDDQNKPWRAYLDLLFPTDTLLLDLLWA
or (SEQ ID NO: 535)
Ac-AKQNDNDNKPWRAYLDLLFPTDTLLLDLLWA
or (SEQ ID NO: 536)
ACQNDDQNCPWRAYLDLLFPTDTLLLDLLWA
or (SEQ ID NO: 505)
ACQNDNDNCPWRAYLDLLFPTDTLLLDLLWA wherein each "—" is a covalent bond;

For example, an epitope comprises a peptide with a length less than 50 amino acids, e.g., a length of between 5 to 20 amino acids. An exemplary epitope comprises an HA peptide, e.g., the peptide comprises the amino acid sequence of YPYDVPDYA (SEQ ID NO: 6).

Other epitopes include the following peptides: QVSH-WVSGLAEGSFG (SEQ ID NO: 1), LSHTSGRVEGSVSLL (SEQ ID NO: 2), QMWAPQWGPD (SEQ ID NO: 3); MASMTGGQQMG (SEQ ID NO: 4); EQKLISEEDL (SEQ ID NO: 5); KETAAAKFERQHMDS (SEQ ID NO: 8); GKPIPNPLLGLDST (SEQ ID NO: 9); DYKDDDDK (SEQ ID NO: 10); GAPVPYPDPLEPR (SEQ ID NO: 11); HHHHHH (SEQ ID NO: 12); TKENPRSNQEESYDDNES (SEQ ID NO: 13); WSHPQFEK (SEQ ID NO: 14); and/or PDRVRAVSHWSS (SEQ ID NO: 15).

In some examples, the epitope comprises a small molecule such as dinitrophenyl (DNP) or a derivative thereof.

Immune Cell Recruitment

In some examples the epitope is an immune cell recruiting molecule.

An exemplary composition, e.g. for recruiting immune cells, comprises the formula of Epitope2-Pept, wherein "Epitope2" is an immune cell recruiting molecule;

wherein "Pept" is a pHLIP® peptide comprising the sequence (SEQ ID NO: 179)
ADDQNPWRAYLDLLFPTDTLLLDLLW;

wherein "—" is a covalent bond. In such examples, the epitope comprises a protein epitope with a length of 350 or less amino acids. An exemplary protein epitope comprises a cytokine. For example, the cytokine comprises an interleukin (IL) such as IL-2, IL-6, IL-7, or IL-12. In other examples, the cytokine comprises tumor necrosis factor (TNF).

In some embodiments, the cytokine comprises a chemokine such as CXCL9, CXCL10, or CXCL11. For example, chemokine comprises CXCL10 comprising the amino acid sequence:

(SEQ ID NO: 514)
MNQTAILICCLIFLTLSGIQGVPLSRTVRCTCISISNQPVNPRSLEKLEII

PASQFCPRVEIIATMKKKGEKRCLNPESKAIKNLLKAVSKERSKRSP.

Compositions with Amino Acid Extension to pHLIP® Peptide

In some aspect, the invention features compositions, constructs, and methods comprising an epitope wherein the membrane non-inserting end of the pHLIP® peptide further comprises an amino acid extension. For example, the composition comprises an epitope and pHLIP® peptide comprises a fusion protein. For example, fusion protein comprises an epitope and a pHLIP® peptide. In other examples, a composition comprises an epitope linked to one or more pHLIP® peptides by a non-cleavable linker compound.

A variety of linkers may be used. For example, the linker is a chemical polymer, e.g., polyethylene glycol. In other examples, the linker is a biopolymer. Exemplary linkers include mucin domain, dextran, cellulose, chitin or starch.

Methods of Treatment

The invention also includes a method of inducing an immune response in a diseased tissue in a subject, comprising administering to a subject a composition comprising an epitope and a pHLIP® peptide. For example, the subject comprises a solid tumor. Alternatively, the subject comprises an inflamed tissue. In some cases, both conditions are present in the subject.

The subject is treated using a variety of clinically acceptable procedures, e.g, the composition is injected directly into a diseased tissue tumor mass. In another example, the composition is systemically administered. As described above, an advantage of the methods is that a biological effect of said composition is at least 20% or more greater than that delivered in the absence of said composition. Another advantage that contributes to the clinical safety and efficacy is that the composition targets preferentially to a diseased tissue compared to a healthy tissue, thereby minimizing damage to healthy tissue.

An exemplary method for promoting an immune response in a subject is carried out by administering to a subject the compositions and constructs described above. Such methods comprise, e.g., lead to, the placement of the epitope(s) on tumor cell or a cell in inflamed tissue of the subject. The increase amount or concentration of the epitope on the surface of the tumor cell or cell in an inflamed tissue leads to a more robust immune response, e.g., antibody-binding or immune cell binding, and subsequent killing and/or elimination of the diseased (or otherwise undesirable) cell. For example, the diseased cell comprises a tumor cell or a cell in inflamed tissue.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The term "alkyl," by itself or as part of another substituent, means, unless otherwise stated, a non-cyclic straight (i.e., unbranched) or branched chain, or combination thereof, which may be fully saturated, mono- or polyunsaturated and can include di- and multivalent radicals, having the number of carbon atoms designated (i.e., C1-C10 means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH2CH2CH2CH2-. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom (e.g. selected from the group consisting of O, N, P, S, Se and Si, and wherein the nitrogen, selenium, and sulfur atoms may optionally be oxidized, and the nitrogen heteroatom may optionally be quaternized). The heteroatom(s) 0, N, P, S, Se, and Si may be placed at any interior position of the heteroalkyl group or at the position at which the alkyl group is attached to the remainder of the molecule. Examples include, but are not limited to: —CH2-CH2-O—CH3, —CH2-CH2-NH—CH3, —CH2-CH2-N(CH3)—CH3, —CH2-S-CH2-CH3, —CH2-CH2, —S(O)—CH3, —CH2-CH2-S(O)2-CH3, —CH═CH—O—CH3, —Si(CH3)3, —CH2-CH═N—OCH3, —CH═CH—N(CH3)—CH3, —O—CH3, —O-CH2-CH3, and —CN. Up to two heteroatoms may be consecutive, such as, for example, —CH2-NH—OCH3.

Similarly, the term "heteroalkylene," by itself or as part of another substituent, means, unless otherwise stated, a divalent radical derived from heteroalkyl, as exemplified, but not limited by, —CH2-CH2-S-CH2-CH2- and —CH2-S-CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)2R'— represents both —C(O)2R'- and —R'C(O)2-. As described above, heteroalkyl groups, as used herein, include those groups that are attached to the remainder of the molecule through a heteroatom, such as —C(O)R', —C(O)NR', —NR'R", —OR', —SeR', —SR', and/or —SO2R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A"cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. selected from N, O, and S, wherein the nitrogen and sulfur atoms are optionally oxidized, and the nitrogen atom(s) are optionally quaternized). Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

Each of the above terms (e.g., "alkyl," "heteroalkyl," "aryl," and "heteroaryl") includes both substituted and unsubstituted forms of the indicated radical.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

An epitope is a molecular region of an antigen capable of eliciting an immune response and of combining with a specific antibody or immune cell produced by such a response. An epitope is also know as an antigenic determinant. For example, an epitope is a part of an antigen molecule to which an antibody attaches or to which an immune cell attaches.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (cutaneous T-cell lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

By, "small molecule" may be referred to broadly as an organic, inorganic or organometallic compound with a low molecular weight compound (e.g., a molecular weight of less than about 2,000 Da or less than about 1,000 Da). The small molecule may have a molecular weight of less than about 2,000 Da, a molecular weight of less than about 1,500 Da, a molecular weight of less than about 1,000 Da, a molecular weight of less than about 900 Da, a molecular weight of less than about 800 Da, a molecular weight of less than about 700 Da, a molecular weight of less than about 600 Da, a molecular weight of less than about 500 Da, a molecular weight of less than about 400 Da, a molecular weight of less than about 300 Da, a molecular weight of less than about 200 Da, a molecular weight of less than about 100 Da, or a molecular weight of less than about 50 Da.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

As used herein, the term “stereoisomers” refers to compounds made up of the same atoms having the same bond order but having different three-dimensional arrangements of atoms that are not interchangeable. The three-dimensional structures are called configurations. As used herein, the term “enantiomers” refers to two stereoisomers that are non-superimposable mirror images of one another. As used herein, the term “optical isomer” is equivalent to the term “enantiomer”. As used herein the term “diastereomer” refers to two stereoisomers which are not mirror images but also not superimposable. The terms “racemate”, “racemic mixture” or “racemic modification” refer to a mixture of equal parts of enantiomers. The term “chiral center” refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., “Enantiomers, Racemates, and Resolutions”, John Wiley and Sons, Inc. 1981).

As used herein, “pharmaceutically acceptable” carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

“Percentage of sequence identity” is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term “identical” or percent “identity,” in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be “substantially identical.” In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the “comparison window” refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
Sequence total quantity: 541
SEQ ID NO: 1          moltype = AA  length = 15
FEATURE               Location/Qualifiers
REGION                1..15
                      note = Description of Artificial Sequence: Synthetic peptide
source                1..15
                      mol_type = protein
                      organism = synthetic construct
SEQUENCE: 1
QVSHWVSGLA EGSFG                                                    15

SEQ ID NO: 2          moltype = AA  length = 15
FEATURE               Location/Qualifiers
REGION                1..15
                      note = Description of Artificial Sequence: Synthetic peptide
source                1..15
                      mol_type = protein
                      organism = synthetic construct
SEQUENCE: 2
LSHTSGRVEG SVSLL                                                    15

SEQ ID NO: 3          moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 3
QMWAPQWGPD                                                          10

SEQ ID NO: 4          moltype = AA  length = 11
FEATURE               Location/Qualifiers
```

-continued

```
REGION                 1..11
                       note = Description of Artificial Sequence: Synthetic peptide
source                 1..11
                       mol_type = protein
                       organism = synthetic construct
SEQUENCE: 4
MASMTGGQQM G                                                   11

SEQ ID NO: 5           moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 5
EQKLISEEDL                                                     10

SEQ ID NO: 6           moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 6
YPYDVPDYA                                                      9

SEQ ID NO: 7           moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 7
YTDIEMNRLG K                                                   11

SEQ ID NO: 8           moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 8
KETAAAKFER QHMDS                                               15

SEQ ID NO: 9           moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 9
GKPIPNPLLG LDST                                                14

SEQ ID NO: 10          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 10
DYKDDDDK                                                       8

SEQ ID NO: 11          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 11
GAPVPYPDPL EPR                                                 13

SEQ ID NO: 12          moltype = AA  length = 6
```

-continued

```
FEATURE                Location/Qualifiers
REGION                 1..6
                       note = Description of Artificial Sequence: Synthetic peptide
source                 1..6
                       mol_type = protein
                       organism = synthetic construct
SEQUENCE: 12
HHHHHH                                                                     6

SEQ ID NO: 13          moltype = AA  length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 13
TKENPRSNQE ESYDDNES                                                        18

SEQ ID NO: 14          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 14
WSHPQFEK                                                                   8

SEQ ID NO: 15          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 15
PDRVRAVSHW SS                                                              12

SEQ ID NO: 16          moltype =   length =
SEQUENCE: 16
000

SEQ ID NO: 17          moltype =   length =
SEQUENCE: 17
000

SEQ ID NO: 18          moltype = AA  length = 28
FEATURE                Location/Qualifiers
REGION                 1..28
                       note = Description of Artificial Sequence: Synthetic peptide
REGION                 1..28
                       note = See specification as filed for detailed description
                        of substitutions and preferred embodiments
source                 1..28
                       mol_type = protein
                       organism = synthetic construct
SITE                   2
                       note = Lys, Cys or an Azido-containing amino acid
SEQUENCE: 18
AXDDQNPWRA YLDLLFPTDT LLLDLLWA                                             28

SEQ ID NO: 19          moltype =   length =
SEQUENCE: 19
000

SEQ ID NO: 20          moltype = AA  length = 36
FEATURE                Location/Qualifiers
REGION                 1..36
                       note = Description of Artificial Sequence: Synthetic
                        polypeptide
REGION                 1..36
                       note = See specification as filed for detailed description
                        of substitutions and preferred embodiments
source                 1..36
                       mol_type = protein
                       organism = synthetic construct
SITE                   2
                       note = Lys, Cys or an Azido-containing amino acid
```

```
SEQUENCE: 20
AXEQNPIYWA RYADWLFTTP LLLLDLALLV DADEGT                        36

SEQ ID NO: 21           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 21
WARYADWLFT TPLLLLDLAL LV                                       22

SEQ ID NO: 22           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 22
GGEQNPIYWA RYADWLFTTP LLLLDLALLV DADEGT                        36

SEQ ID NO: 23           moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 23
AEQNPIYWAR YADWLFTTPL LLLDLALLVD ADEGT                         35

SEQ ID NO: 24           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 24
ADDQNPWRAY LDLLFPTDTL LLDLLWDADE CG                            32

SEQ ID NO: 25           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 25
ACDDQNPWRA YLDLLFPTDT LLLDLLWDAD EG                            32

SEQ ID NO: 26           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 26
AKDDQNPWRA YLDLLFPTDT LLLDLLWDAD EG                            32

SEQ ID NO: 27           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 27
AAEQNPIYWA RYADWLFTTP LLLLDLALLV DADEGTCG                      38
```

-continued

```
SEQ ID NO: 28          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 28
AEQNPIYWAR YADWLFTTPL LLLDLALLVD ADEGCT                            36

SEQ ID NO: 29          moltype = AA  length = 38
FEATURE                Location/Qualifiers
REGION                 1..38
                       note = Description of Artificial Sequence: Synthetic
                        polypeptide
source                 1..38
                       mol_type = protein
                       organism = synthetic construct
SEQUENCE: 29
GGEQNPIYWA RYADWLFTTP LLLLDLALLV DADEGTCG                          38

SEQ ID NO: 30          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 30
ACEQNPIYWA RYADWLFTTP LLLLDLALLV DADEGTG                           37

SEQ ID NO: 31          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 31
ACEQNPIYWA RYADWLFTTP LLLLDLALLV DADEGT                            36

SEQ ID NO: 32          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 32
AKEQNPIYWA RYADWLFTTP LLLLDLALLV DADEGT                            36

SEQ ID NO: 33          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 33
AKEQNPIYWA RYADWLFTTP LLLLDLALLV DADEGTG                           37

SEQ ID NO: 34          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 34
AAEQNPIYWA RYADWLFTTP LLLLDLALLV DADEGTKCG                         39

SEQ ID NO: 35          moltype = AA  length = 36
FEATURE                Location/Qualifiers
```

```
REGION                 1..36
                       note = Description of Artificial Sequence: Synthetic
                        polypeptide
source                 1..36
                       mol_type = protein
                       organism = synthetic construct
SEQUENCE: 35
AKEQNPIYWA RYADWLFTTP LLLLDLALLV DADECT                            36

SEQ ID NO: 36          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 36
ACEQNPIYWA RYANWLFTTP LLLLNLALLV DADEGTG                           37

SEQ ID NO: 37          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 37
ACEQNPIYWA RYANWLFTTP LLLLNLALLV DADEGT                            36

SEQ ID NO: 38          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 38
ACEQNPIYWA RYAKWLFTTP LLLLKLALLV DADEGTG                           37

SEQ ID NO: 39          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 39
GGEQNPIYWA RYADWLFTTP LLLLDLALLV NANQGT                            36

SEQ ID NO: 40          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 40
AAEQNPIYWA RYADWLFTTP LLLLALALLV DADEGT                            36

SEQ ID NO: 41          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 41
AAEQNPIYWA RYADWLFTTP LLLLELALLV DADEGTKCG                         39

SEQ ID NO: 42          moltype = AA  length = 36
FEATURE                Location/Qualifiers
REGION                 1..36
                       note = Description of Artificial Sequence: Synthetic
```

```
                         polypeptide
source                  1..36
                        mol_type = protein
                        organism = synthetic construct
SEQUENCE: 42
AAEQNPIYWA RYAAWLFTTP LLLLDLALLV DADEGT                            36

SEQ ID NO: 43           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 43
AAEQNPIYWA RYADWLFTTA LLLLDLALLV DADEGT                            36

SEQ ID NO: 44           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 44
AAEQNPIYWA RYADWLFTTP LLLLELALLV DADEGT                            36

SEQ ID NO: 45           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 45
AAEQNPIYWA RYAEWLFTTP LLLLDLALLV DADEGT                            36

SEQ ID NO: 46           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 46
AAEQNPIIYW ARYADWLFTD LPLLLLDLLA LLVDADEGT                         39

SEQ ID NO: 47           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 47
GEQNPIYWAQ YADWLFTTPL LLLDLALLVD ADEGTCG                           37

SEQ ID NO: 48           moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 48
GGEQNPIYWA RYADWLFTTP LLLDLLALLV DADEGTCG                          38

SEQ ID NO: 49           moltype = AA  length = 38
FEATURE                 Location/Qualifiers
REGION                  1..38
                        note = Description of Artificial Sequence: Synthetic
                         polypeptide
source                  1..38
```

-continued

```
                         mol_type = protein
                         organism = synthetic construct
SEQUENCE: 49
GGEQNPIYWA RYADWLFTTP LLLLLDALLV DADEGTCG                            38

SEQ ID NO: 50            moltype = AA  length = 38
FEATURE                  Location/Qualifiers
REGION                   1..38
                         note = Description of Artificial Sequence: Synthetic
                          polypeptide
source                   1..38
                         mol_type = protein
                         organism = synthetic construct
SEQUENCE: 50
GGEQNPIYWA RYDAWLFTTP LLLLDLALLV DADEGTCG                            38

SEQ ID NO: 51            moltype = AA  length = 38
FEATURE                  Location/Qualifiers
REGION                   1..38
                         note = Description of Artificial Sequence: Synthetic
                          polypeptide
source                   1..38
                         mol_type = protein
                         organism = synthetic construct
SEQUENCE: 51
GGEQNPIYWA RYAWDLFTTP LLLLDLALLV DADEGTCG                            38

SEQ ID NO: 52            moltype = AA  length = 36
FEATURE                  Location/Qualifiers
REGION                   1..36
                         note = Description of Artificial Sequence: Synthetic
                          polypeptide
source                   1..36
                         mol_type = protein
                         organism = synthetic construct
SEQUENCE: 52
AAEQNPIYWA RYADWLFTTG LLLLDLALLV DADEGT                              36

SEQ ID NO: 53            moltype = AA  length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
SEQUENCE: 53
DDDEDNPIYW ARYADWLFTT PLLLLHGALL VDADECT                             37

SEQ ID NO: 54            moltype = AA  length = 36
FEATURE                  Location/Qualifiers
REGION                   1..36
                         note = Description of Artificial Sequence: Synthetic
                          polypeptide
source                   1..36
                         mol_type = protein
                         organism = synthetic construct
SEQUENCE: 54
DDDEDNPIYW ARYADWLFTT PLLLLHGALL VDADET                              36

SEQ ID NO: 55            moltype = AA  length = 38
FEATURE                  Location/Qualifiers
REGION                   1..38
                         note = Description of Artificial Sequence: Synthetic
                          polypeptide
source                   1..38
                         mol_type = protein
                         organism = synthetic construct
SEQUENCE: 55
DDDEDNPIYW ARYAHWLFTT PLLLLHGALL VDADEGCT                            38

SEQ ID NO: 56            moltype = AA  length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
```

```
SEQUENCE: 56
CDDDEDNPIY WARYAHWLFT TPLLLLHGAL LVDADET                        37

SEQ ID NO: 57          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 57
DDDEDNPIYW ARYAHWLFTT PLLLLHGALL VDADEGT                        37

SEQ ID NO: 58          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 58
DDDEDNPIYW ARYAHWLFTT PLLLLHGALL VNADECT                        37

SEQ ID NO: 59          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 59
DDDEDNPIYW ARYAHWLFTT PLLLLHGALL VNADEGT                        37

SEQ ID NO: 60          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 60
DDDEDNPIYW ARYAHWLFTT PLLLLHGALL VNANECT                        37

SEQ ID NO: 61          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 61
DDDEDNPIYW ARYAHWLFTT PLLLLHGALL VNANEGT                        37

SEQ ID NO: 62          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 62
AEQNPIYWAR YADFLFTTPL LLLDLALLVD ADET                           34

SEQ ID NO: 63          moltype = AA  length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 63
AEQNPIYFAR YADWLFTTPL LLLDLALLVD ADEGT                          35
```

```
SEQ ID NO: 64          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 64
AEQNPIYFAR YADFLFTTPL LLLDLALLWD ADET                              34

SEQ ID NO: 65          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 65
AKEDQNPYWA RYADWLFTTP LLLLDLALLV DG                                32

SEQ ID NO: 66          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 66
ACEDQNPYWA RYADWLFTTP LLLLDLALLV DG                                32

SEQ ID NO: 67          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 67
AEDQNPYWAR YADWLFTTPL LLLDLALLVD CG                                32

SEQ ID NO: 68          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 68
AEDQNPYWAR YADWLFTTPL LLLELALLVE CG                                32

SEQ ID NO: 69          moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 69
AKEDQNDPYW ARYADWLFTT PLLLLDLALL VG                                32

SEQ ID NO: 70          moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 70
AKEDQNPYWR AYADLFTPLT LLDLLALWDG                                   30

SEQ ID NO: 71          moltype = AA  length = 31
```

```
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 71
AEDQNPYWAR YADWLFTTPL LLLELALLVC G                                31

SEQ ID NO: 72          moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 72
ACEDQNPYWR AYADLFTPLT LLDLLALWDG                                  30

SEQ ID NO: 73          moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 73
ACDDQNPWRA YLDLLFPTDT LLLDLLW                                     27

SEQ ID NO: 74          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 74
AKDDQNPWRA YLDLLFPTDT LLLDLLWC                                    28

SEQ ID NO: 75          moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 75
ACEEQNPWRA YLELLFPTET LLLELLW                                     27

SEQ ID NO: 76          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 76
ACDDQNPWAR YLDWLFPTDT LLLDL                                       25

SEQ ID NO: 77          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 77
CDNNNPWRAY LDLLFPTDTL LLDW                                        24

SEQ ID NO: 78          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 78
```

```
CEEQQPWAQY LELLFPTETL LLEW                                        24

SEQ ID NO: 79          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 79
CEEQQPWRAY LELLFPTETL LLEW                                        24

SEQ ID NO: 80          moltype = AA  length = 37
FEATURE                Location/Qualifiers
REGION                 1..37
                       note = Description of Artificial Sequence: Synthetic
                        polypeptide
source                 1..37
                       mol_type = protein
                       organism = synthetic construct
SEQUENCE: 80
CDDDDDNPNY WARYANWLFT TPLLLLNGAL LVEAEET                          37

SEQ ID NO: 81          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 81
CDDDDDNPNY WARYAPWLFT TPLLLLPGAL LVEAEE                           36

SEQ ID NO: 82          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 82
TEDADVLLAL DLLLLPTTFL WDAYRAWYPN QECA                             34

SEQ ID NO: 83          moltype = AA  length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 83
AEQNPIYWAR YADWLFTTPL                                             20

SEQ ID NO: 84          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 84
AEQNPIYWAR YADWLFTTPC L                                           21

SEQ ID NO: 85          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 85
ACEQNPIYWA RYADWLFTTP L                                           21

SEQ ID NO: 86          moltype = AA  length = 20
FEATURE                Location/Qualifiers
REGION                 1..20
                       note = Description of Artificial Sequence: Synthetic peptide
```

```
source                  1..20
                        mol_type = protein
                        organism = synthetic construct
SEQUENCE: 86
AEQNPIYFAR YADWLFTTPL                                                20

SEQ ID NO: 87           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 87
AEQNPIYFAR YADLLFPTTL AW                                             22

SEQ ID NO: 88           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 88
AEQNPIYWAR YADLLFPTTL AF                                             22

SEQ ID NO: 89           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 89
AEQNPIYWAR YADLLFPTTL AW                                             22

SEQ ID NO: 90           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 90
KEDQNPWARY ADLLFPTTLA W                                              21

SEQ ID NO: 91           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 91
KEDQNPWARY ADLLFPTTLW                                                20

SEQ ID NO: 92           moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 92
ACEDQNPWAR YADLLFPTTL AW                                             22

SEQ ID NO: 93           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 93
ACEDQNPWAR YADWLFPTTL LLLD                                           24

SEQ ID NO: 94           moltype = AA  length = 22
FEATURE                 Location/Qualifiers
REGION                  1..22
```

```
                        note = Description of Artificial Sequence: Synthetic peptide
source                  1..22
                        mol_type = protein
                        organism = synthetic construct
SEQUENCE: 94
ACEEQNPWAR YAELLFPTTL AW                                                22

SEQ ID NO: 95           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 95
ACEEQNPWAR YAEWLFPTTL LLLE                                              24

SEQ ID NO: 96           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 96
ACEEQNPWAR YLEWLFPTET LLLEL                                             25

SEQ ID NO: 97           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 97
ACEEQNPQAE YAEWLFPTTL LLLE                                              24

SEQ ID NO: 98           moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 98
WARYADWLFT TPLLLLDLAL L                                                 21

SEQ ID NO: 99           moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 99
YARYADWLFT TPLLLLDLAL L                                                 21

SEQ ID NO: 100          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 100
WARYSDWLFT TPLLLYDLGL L                                                 21

SEQ ID NO: 101          moltype = AA  length = 21
FEATURE                 Location/Qualifiers
REGION                  1..21
```

```
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 101
WARYTDWFTT PLLLYDLALL A                                              21

SEQ ID NO: 102          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 102
WARYTDWLFT TPLLLYDLGL L                                              21

SEQ ID NO: 103          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 103
WARYADWLFT TPLLLLDLSL L                                              21

SEQ ID NO: 104          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 104
LLALDLLLLP TTFLWDAYRA W                                              21

SEQ ID NO: 105          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 105
LLALDLLLLP TTFLWDAYRA Y                                              21

SEQ ID NO: 106          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 106
LLGLDYLLLP TTFLWDSYRA W                                              21

SEQ ID NO: 107          moltype = AA  length = 21
FEATURE                 Location/Qualifiers
REGION                  1..21
                        note = Description of Artificial Sequence: Synthetic peptide
```

-continued

```
REGION                  1..21
                        note = See specification as filed for detailed description
                         of substitutions and preferred embodiments
source                  1..21
                        mol_type = protein
                        organism = synthetic construct
SEQUENCE: 107
ALLALDYLLL PTTFWDTYRA W                                             21

SEQ ID NO: 108          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 108
LLGLDYLLLP TTFLWDTYRA W                                             21

SEQ ID NO: 109          moltype = AA  length = 21
FEATURE                 Location/Qualifiers
REGION                  1..21
                        note = Description of Artificial Sequence: Synthetic peptide
REGION                  1..21
                        note = See specification as filed for detailed description
                         of substitutions and preferred embodiments
source                  1..21
                        mol_type = protein
                        organism = synthetic construct
SEQUENCE: 109
LLSLDLLLLP TTFLWDAYRA W                                             21

SEQ ID NO: 110          moltype = AA  length = 26
FEATURE                 Location/Qualifiers
REGION                  1..26
                        note = Description of Artificial Sequence: Synthetic peptide
REGION                  1..26
                        note = See specification as filed for detailed description
                         of substitutions and preferred embodiments
source                  1..26
                        mol_type = protein
                        organism = synthetic construct
SEQUENCE: 110
GLAGLLGLEG LLGLPLGLLE GLWLGL                                        26

SEQ ID NO: 111          moltype = AA  length = 26
FEATURE                 Location/Qualifiers
REGION                  1..26
                        note = Description of Artificial Sequence: Synthetic peptide
REGION                  1..26
                        note = See specification as filed for detailed description
                         of substitutions and preferred embodiments
source                  1..26
                        mol_type = protein
                        organism = synthetic construct
SEQUENCE: 111
LGLWLGELLG LPLGLLGELG LLGALG                                        26

SEQ ID NO: 112          moltype = AA  length = 20
FEATURE                 Location/Qualifiers
REGION                  1..20
                        note = Description of Artificial Sequence: Synthetic peptide
REGION                  1..20
                        note = See specification as filed for detailed description
                         of substitutions and preferred embodiments
source                  1..20
                        mol_type = protein
                        organism = synthetic construct
SEQUENCE: 112
WRAYLDLLFP TDTLLLDLLW                                               20

SEQ ID NO: 113          moltype = AA  length = 20
FEATURE                 Location/Qualifiers
REGION                  1..20
                        note = Description of Artificial Sequence: Synthetic peptide
REGION                  1..20
```

```
                         note = See specification as filed for detailed description
                          of substitutions and preferred embodiments
source                   1..20
                         mol_type = protein
                         organism = synthetic construct
SEQUENCE: 113
WLLDLLLTDT PFLLDLYARW                                                20

SEQ ID NO: 114           moltype = AA  length = 18
FEATURE                  Location/Qualifiers
REGION                   1..18
                         note = Description of Artificial Sequence: Synthetic peptide
REGION                   1..18
                         note = See specification as filed for detailed description
                          of substitutions and preferred embodiments
source                   1..18
                         mol_type = protein
                         organism = synthetic construct
SEQUENCE: 114
WARYLEWLFP TETLLLEL                                                  18

SEQ ID NO: 115           moltype = AA  length = 18
FEATURE                  Location/Qualifiers
REGION                   1..18
                         note = Description of Artificial Sequence: Synthetic peptide
REGION                   1..18
                         note = See specification as filed for detailed description
                          of substitutions and preferred embodiments
source                   1..18
                         mol_type = protein
                         organism = synthetic construct
SEQUENCE: 115
WAQYLELLFP TETLLLEW                                                  18

SEQ ID NO: 116           moltype = AA  length = 18
FEATURE                  Location/Qualifiers
REGION                   1..18
                         note = Description of Artificial Sequence: Synthetic peptide
REGION                   1..18
                         note = See specification as filed for detailed description
                          of substitutions and preferred embodiments
source                   1..18
                         mol_type = protein
                         organism = synthetic construct
SEQUENCE: 116
LELLLTETPF LWELYRAW                                                  18

SEQ ID NO: 117           moltype = AA  length = 18
FEATURE                  Location/Qualifiers
REGION                   1..18
                         note = Description of Artificial Sequence: Synthetic peptide
REGION                   1..18
                         note = See specification as filed for detailed description
                          of substitutions and preferred embodiments
source                   1..18
                         mol_type = protein
                         organism = synthetic construct
SEQUENCE: 117
WELLLTETPF LLELYQAW                                                  18

SEQ ID NO: 118           moltype = AA  length = 17
FEATURE                  Location/Qualifiers
REGION                   1..17
                         note = Description of Artificial Sequence: Synthetic peptide
REGION                   1..17
                         note = See specification as filed for detailed description
                          of substitutions and preferred embodiments
source                   1..17
                         mol_type = protein
                         organism = synthetic construct
SEQUENCE: 118
WLFTTPLLLL NGALLVE                                                   17

SEQ ID NO: 119           moltype = AA  length = 17
FEATURE                  Location/Qualifiers
REGION                   1..17
                         note = Description of Artificial Sequence: Synthetic peptide
REGION                   1..17
                         note = See specification as filed for detailed description
```

```
                        of substitutions and preferred embodiments
source                 1..17
                       mol_type = protein
                       organism = synthetic construct
SEQUENCE: 119
WLFTTPLLLL PGALLVE                                          17

SEQ ID NO: 120         moltype = AA  length = 15
FEATURE                Location/Qualifiers
REGION                 1..15
                       note = Description of Artificial Sequence: Synthetic peptide
REGION                 1..15
                       note = See specification as filed for detailed description
                        of substitutions and preferred embodiments
source                 1..15
                       mol_type = protein
                       organism = synthetic construct
SEQUENCE: 120
WARYADLLFP TTLAW                                            15

SEQ ID NO: 121         moltype = AA  length = 17
FEATURE                Location/Qualifiers
REGION                 1..17
                       note = Description of Artificial Sequence: Synthetic peptide
REGION                 1..17
                       note = See specification as filed for detailed description
                        of substitutions and preferred embodiments
source                 1..17
                       mol_type = protein
                       organism = synthetic construct
SEQUENCE: 121
EVLLAGNLLL LPTTFLW                                          17

SEQ ID NO: 122         moltype = AA  length = 17
FEATURE                Location/Qualifiers
REGION                 1..17
                       note = Description of Artificial Sequence: Synthetic peptide
REGION                 1..17
                       note = See specification as filed for detailed description
                        of substitutions and preferred embodiments
source                 1..17
                       mol_type = protein
                       organism = synthetic construct
SEQUENCE: 122
EVLLAGPLLL LPTTFLW                                          17

SEQ ID NO: 123         moltype = AA  length = 15
FEATURE                Location/Qualifiers
REGION                 1..15
                       note = Description of Artificial Sequence: Synthetic peptide
REGION                 1..15
                       note = See specification as filed for detailed description
                        of substitutions and preferred embodiments
source                 1..15
                       mol_type = protein
                       organism = synthetic construct
SEQUENCE: 123
WALTTPFLLD AYRAW                                            15

SEQ ID NO: 124         moltype = AA  length = 24
FEATURE                Location/Qualifiers
REGION                 1..24
                       note = Description of Artificial Sequence: Synthetic peptide
REGION                 1..24
                       note = See specification as filed for detailed description
                        of substitutions and preferred embodiments
source                 1..24
                       mol_type = protein
                       organism = synthetic construct
SEQUENCE: 124
NLEGFFATLG GEIALWSLVV LAIE                                  24

SEQ ID NO: 125         moltype = AA  length = 22
FEATURE                Location/Qualifiers
REGION                 1..22
                       note = Description of Artificial Sequence: Synthetic peptide
REGION                 1..22
                       note = See specification as filed for detailed description
                        of substitutions and preferred embodiments
```

```
source                 1..22
                       mol_type = protein
                       organism = synthetic construct
SEQUENCE: 125
EGFFATLGGE IALWSDVVLA IE                                           22

SEQ ID NO: 126         moltype = AA  length = 22
FEATURE                Location/Qualifiers
REGION                 1..22
                       note = Description of Artificial Sequence: Synthetic peptide
REGION                 1..22
                       note = See specification as filed for detailed description
                        of substitutions and preferred embodiments
source                 1..22
                       mol_type = protein
                       organism = synthetic construct
SEQUENCE: 126
EGFFATLGGE IPLWSDVVLA IE                                           22

SEQ ID NO: 127         moltype = AA  length = 24
FEATURE                Location/Qualifiers
REGION                 1..24
                       note = Description of Artificial Sequence: Synthetic peptide
REGION                 1..24
                       note = See specification as filed for detailed description
                        of substitutions and preferred embodiments
source                 1..24
                       mol_type = protein
                       organism = synthetic construct
SEQUENCE: 127
EIALVVLSWL AIEGGLTAFF GELN                                         24

SEQ ID NO: 128         moltype = AA  length = 22
FEATURE                Location/Qualifiers
REGION                 1..22
                       note = Description of Artificial Sequence: Synthetic peptide
REGION                 1..22
                       note = See specification as filed for detailed description
                        of substitutions and preferred embodiments
source                 1..22
                       mol_type = protein
                       organism = synthetic construct
SEQUENCE: 128
EIALVVDSWL AIEGGLTAFF GE                                           22

SEQ ID NO: 129         moltype = AA  length = 22
FEATURE                Location/Qualifiers
REGION                 1..22
                       note = Description of Artificial Sequence: Synthetic peptide
REGION                 1..22
                       note = See specification as filed for detailed description
                        of substitutions and preferred embodiments
source                 1..22
                       mol_type = protein
                       organism = synthetic construct
SEQUENCE: 129
EIALVVDSWL PIEGGLTAFF GE                                           22

SEQ ID NO: 130         moltype = AA  length = 21
FEATURE                Location/Qualifiers
REGION                 1..21
                       note = Description of Artificial Sequence: Synthetic peptide
REGION                 1..21
                       note = See specification as filed for detailed description
                        of substitutions and preferred embodiments
source                 1..21
                       mol_type = protein
                       organism = synthetic construct
SEQUENCE: 130
ILDLVFGLLF AVTSVDFLVQ W                                            21

SEQ ID NO: 131         moltype = AA  length = 21
FEATURE                Location/Qualifiers
REGION                 1..21
                       note = Description of Artificial Sequence: Synthetic peptide
REGION                 1..21
                       note = See specification as filed for detailed description
                        of substitutions and preferred embodiments
source                 1..21
```

```
                        mol_type = protein
                        organism = synthetic construct
SEQUENCE: 131
WQVLFDVSTV AFLLGFVLDL I                                      21

SEQ ID NO: 132          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 132
AEQNPIYWAR YADWLFTTPL LLLDLALLVD ADET                        34

SEQ ID NO: 133          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 133
AEQNPIYWAR YAEWLFTTPL LLLELALLVE AEET                        34

SEQ ID NO: 134          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 134
ADDQNPWRAY LDLLFPDTTD LLLLDLLWDA DET                         33

SEQ ID NO: 135          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 135
AEEQNPWRAY LELLFPETTE LLLLELLWEA EET                         33

SEQ ID NO: 136          moltype = AA  length = 34
FEATURE                 Location/Qualifiers
REGION                  1..34
                        note = Description of Artificial Sequence: Synthetic
                         polypeptide
MOD_RES                 13
                        note = gamma-carboxyglutamic acid
source                  1..34
                        mol_type = protein
                        organism = synthetic construct
SEQUENCE: 136
AEQNPIYWAR YAXWLFTTPL LLLDLALLVD ADET                        34

SEQ ID NO: 137          moltype = AA  length = 34
FEATURE                 Location/Qualifiers
REGION                  1..34
                        note = Description of Artificial Sequence: Synthetic
                         polypeptide
MOD_RES                 24
                        note = gamma-carboxyglutamic acid
source                  1..34
                        mol_type = protein
                        organism = synthetic construct
SEQUENCE: 137
AEQNPIYWAR YADWLFTTPL LLLXLALLVD ADET                        34

SEQ ID NO: 138          moltype = AA  length = 34
FEATURE                 Location/Qualifiers
REGION                  1..34
                        note = Description of Artificial Sequence: Synthetic
```

```
                       polypeptide
MOD_RES                13
                       note = gamma-carboxyglutamic acid
MOD_RES                24
                       note = gamma-carboxyglutamic acid
source                 1..34
                       mol_type = protein
                       organism = synthetic construct
SEQUENCE: 138
AEQNPIYWAR YAXWLFTTPL LLLXLALLVD ADET                             34

SEQ ID NO: 139         moltype = AA  length = 34
FEATURE                Location/Qualifiers
REGION                 1..34
                       note = Description of Artificial Sequence: Synthetic
                        polypeptide
MOD_RES                13
                       note = Aad
source                 1..34
                       mol_type = protein
                       organism = synthetic construct
SEQUENCE: 139
AEQNPIYWAR YAXWLFTTPL LLLDLALLVD ADET                             34

SEQ ID NO: 140         moltype = AA  length = 34
FEATURE                Location/Qualifiers
REGION                 1..34
                       note = Description of Artificial Sequence: Synthetic
                        polypeptide
MOD_RES                24
                       note = Aad
source                 1..34
                       mol_type = protein
                       organism = synthetic construct
SEQUENCE: 140
AEQNPIYWAR YADWLFTTPL LLLXLALLVD ADET                             34

SEQ ID NO: 141         moltype = AA  length = 34
FEATURE                Location/Qualifiers
REGION                 1..34
                       note = Description of Artificial Sequence: Synthetic
                        polypeptide
MOD_RES                13
                       note = Aad
MOD_RES                24
                       note = Aad
source                 1..34
                       mol_type = protein
                       organism = synthetic construct
SEQUENCE: 141
AEQNPIYWAR YAXWLFTTPL LLLXLALLVD ADET                             34

SEQ ID NO: 142         moltype = AA  length = 34
FEATURE                Location/Qualifiers
REGION                 1..34
                       note = Description of Artificial Sequence: Synthetic
                        polypeptide
MOD_RES                13
                       note = gamma-carboxyglutamic acid
MOD_RES                24
                       note = Aad
source                 1..34
                       mol_type = protein
                       organism = synthetic construct
SEQUENCE: 142
AEQNPIYWAR YAXWLFTTPL LLLXLALLVD ADET                             34

SEQ ID NO: 143         moltype = AA  length = 34
FEATURE                Location/Qualifiers
REGION                 1..34
                       note = Description of Artificial Sequence: Synthetic
                        polypeptide
MOD_RES                13
                       note = Aad
MOD_RES                24
                       note = gamma-carboxyglutamic acid
source                 1..34
                       mol_type = protein
                       organism = synthetic construct
```

```
SEQUENCE: 143
AEQNPIYWAR YAXWLFTTPL LLLXLALLVD ADET                             34

SEQ ID NO: 144         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 144
GGEQNPIYWA RYADWLFTTP LLLLDLALLV DADEGT                           36

SEQ ID NO: 145         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 145
GGEQNPIYWA RYADWLFTTP LLLLDLALLV DADEGT                           36

SEQ ID NO: 146         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 146
AAEQNPIYWA RYADWLFTTP LLLLDLALLV DADEGT                           36

SEQ ID NO: 147         moltype = AA  length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 147
AEQNPIYWAR YADWLFTTPL LLLDLALLVD ADEGT                            35

SEQ ID NO: 148         moltype = AA  length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 148
AEQNPIYWAR YANWLFTTPL LLLNLALLVD ADEGT                            35

SEQ ID NO: 149         moltype = AA  length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 149
AEQNPIYWAR YAKWLFTTPL LLLKLALLVD ADEGT                            35

SEQ ID NO: 150         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 150
GGEQNPIYWA RYADWLFTTP LLLLDLALLV NANQGT                           36
```

```
SEQ ID NO: 151          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 151
AAEQNPIYWA RYADWLFTTP LLLLALALLV DADEGT                            36

SEQ ID NO: 152          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 152
AAEQNPIYWA RYAAWLFTTP LLLLDLALLV DADEGT                            36

SEQ ID NO: 153          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 153
AAEQNPIYWA RYADWLFTTA LLLLDLALLV DADEGT                            36

SEQ ID NO: 154          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 154
AAEQNPIYWA RYADWLFTTP LLLLELALLV DADEGT                            36

SEQ ID NO: 155          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 155
AAEQNPIYWA RYAEWLFTTP LLLLDLALLV DADEGT                            36

SEQ ID NO: 156          moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 156
AAEQNPIIYW ARYADWLFTD LPLLLLDLLA LLVDADEGT                         39

SEQ ID NO: 157          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 157
GEQNPIYWAQ YADWLFTTPL LLLDLALLVD ADEG                              34

SEQ ID NO: 158          moltype = AA  length = 35
```

```
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 158
GGEQNPIYWA RYADWLFTTP LLLDLLALLV DADEG                        35

SEQ ID NO: 159          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 159
GGEQNPIYWA RYADWLFTTP LLLLLDALLV DADEG                        35

SEQ ID NO: 160          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 160
GGEQNPIYWA RYDAWLFTTP LLLLDLALLV DADEGT                       36

SEQ ID NO: 161          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 161
GGEQNPIYWA RYAWDLFTTP LLLLDLALLV DADEG                        35

SEQ ID NO: 162          moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 162
AAEQNPIYWA RYADWLFTTG LLLLDLALLV DADEGT                       36

SEQ ID NO: 163          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 163
DDDEDNPIYW ARYADWLFTT PLLLLHGALL VDAD                         34

SEQ ID NO: 164          moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 164
DDDEDNPIYW ARYAHWLFTT PLLLLHGALL VDADE                        35

SEQ ID NO: 165          moltype = AA  length = 33
FEATURE                 Location/Qualifiers
REGION                  1..33
```

```
                        note = Description of Artificial Sequence: Synthetic
                         polypeptide
source                  1..33
                        mol_type = protein
                        organism = synthetic construct
SEQUENCE: 165
CEQNPIYWAR YADWHFTTPL LLLDLALLVD ADE                               33

SEQ ID NO: 166          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 166
AEQNPIYWAR YADFLFTTPL LLLDLALLVD ADET                              34

SEQ ID NO: 167          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 167
AEQNPIYFAR YADWLFTTPL LLLDLALLVD ADE                               33

SEQ ID NO: 168          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 168
AEQNPIYFAR YADFLFTTPL LLLDLALLWD ADET                              34

SEQ ID NO: 169          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 169
ADNNPWIYAR YADLTTFPLL LLDLALLVDF DD                                32

SEQ ID NO: 170          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 170
ADNNPFIYAR YADLTTWPLL LLDLALLVDF DD                                32

SEQ ID NO: 171          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 171
ADNNPFIYAR YADLTTFPLL LLDLALLVDW DD                                32

SEQ ID NO: 172          moltype = AA  length = 32
FEATURE                 Location/Qualifiers
REGION                  1..32
                        note = Description of Artificial Sequence: Synthetic
                         polypeptide
```

-continued

```
source                  1..32
                        mol_type = protein
                        organism = synthetic construct
SEQUENCE: 172
ADNNPFPYAR YADLTTWILL LLDLALLVDF DD                                     32

SEQ ID NO: 173          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 173
ADNNPFIYAY RADLTTFPLL LLDLALLVDW DD                                     32

SEQ ID NO: 174          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 174
ADNNPFIYAT YADLRTFPLL LLDLALLVDW DD                                     32

SEQ ID NO: 175          moltype = AA  length = 33
FEATURE                 Location/Qualifiers
REGION                  1..33
                        note = Description of Artificial Sequence: Synthetic
                         polypeptide
source                  1..33
                        mol_type = protein
                        organism = synthetic construct
SEQUENCE: 175
TEDADVLLAL DLLLLPTTFL WDAYRAWYPN QEA                                    33

SEQ ID NO: 176          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 176
AEDQNPYWAR YADWLFTTPL LLLDLALLVD                                        30

SEQ ID NO: 177          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 177
AEDQNPYWAR YADWLFTTPL LLLELALLVE                                        30

SEQ ID NO: 178          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 178
AEDQNPYWRA YADLFTPLTL LDLLALWD                                          28

SEQ ID NO: 179          moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 179
```

-continued

```
ADDQNPWRAY LDLLFPTDTL LLDLLW                                          26

SEQ ID NO: 180          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 180
ADDQNPWRAY LDLLFPTDTL LLDLLWDADE                                      30

SEQ ID NO: 181          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
source                  1..26
                        mol_type = protein
                        organism = synthetic construct
SEQUENCE: 181
ADDQNPWRAY LXLLFPTDTL LLDLLW                                          26

SEQ ID NO: 182          moltype = AA  length = 26
FEATURE                 Location/Qualifiers
REGION                  1..26
                        note = Description of Artificial Sequence: Synthetic peptide
MOD_RES                 18
                        note = gamma-carboxyglutamic acid
source                  1..26
                        mol_type = protein
                        organism = synthetic construct
SEQUENCE: 182
ADDQNPWRAY LDLLFPTXTL LLDLLW                                          26

SEQ ID NO: 183          moltype = AA  length = 26
FEATURE                 Location/Qualifiers
REGION                  1..26
                        note = Description of Artificial Sequence: Synthetic peptide
MOD_RES                 23
                        note = gamma-carboxyglutamic acid
source                  1..26
                        mol_type = protein
                        organism = synthetic construct
SEQUENCE: 183
ADDQNPWRAY LDLLFPTDTL LLXLLW                                          26

SEQ ID NO: 184          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 18
                        note = gamma-carboxyglutamic acid
source                  1..26
                        mol_type = protein
                        organism = synthetic construct
SEQUENCE: 184
ADDQNPWRAY LXLLFPTXTL LLDLLW                                          26

SEQ ID NO: 185          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 23
                        note = gamma-carboxyglutamic acid
source                  1..26
                        mol_type = protein
                        organism = synthetic construct
SEQUENCE: 185
ADDQNPWRAY LXLLFPTDTL LLXLLW                                          26

SEQ ID NO: 186          moltype = AA  length = 26
FEATURE                 Location/Qualifiers
```

-continued

```
REGION                  1..26
                        note = Description of Artificial Sequence: Synthetic peptide
MOD_RES                 18
                        note = Gla
MOD_RES                 23
                        note = Gla
source                  1..26
                        mol_type = protein
                        organism = synthetic construct
SEQUENCE: 186
ADDQNPWRAY LDLLFPTXTL LLXLLW                                        26

SEQ ID NO: 187          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 18
                        note = gamma-carboxyglutamic acid
MOD_RES                 23
                        note = gamma-carboxyglutamic acid
source                  1..26
                        mol_type = protein
                        organism = synthetic construct
SEQUENCE: 187
ADDQNPWRAY LXLLFPTXTL LLXLLW                                        26

SEQ ID NO: 188          moltype = AA  length = 26
FEATURE                 Location/Qualifiers
REGION                  1..26
                        note = Description of Artificial Sequence: Synthetic peptide
MOD_RES                 12
                        note = Aad
source                  1..26
                        mol_type = protein
                        organism = synthetic construct
SEQUENCE: 188
ADDQNPWRAY LXLLFPTDTL LLDLLW                                        26

SEQ ID NO: 189          moltype = AA  length = 26
FEATURE                 Location/Qualifiers
REGION                  1..26
                        note = Description of Artificial Sequence: Synthetic peptide
MOD_RES                 18
                        note = Aad
source                  1..26
                        mol_type = protein
                        organism = synthetic construct
SEQUENCE: 189
ADDQNPWRAY LDLLFPTXTL LLDLLW                                        26

SEQ ID NO: 190          moltype = AA  length = 26
FEATURE                 Location/Qualifiers
REGION                  1..26
                        note = Description of Artificial Sequence: Synthetic peptide
MOD_RES                 23
                        note = Aad
source                  1..26
                        mol_type = protein
                        organism = synthetic construct
SEQUENCE: 190
ADDQNPWRAY LDLLFPTDTL LLXLLW                                        26

SEQ ID NO: 191          moltype = AA  length = 26
FEATURE                 Location/Qualifiers
REGION                  1..26
                        note = Description of Artificial Sequence: Synthetic peptide
MOD_RES                 12
                        note = Aad
MOD_RES                 18
                        note = Aad
source                  1..26
                        mol_type = protein
                        organism = synthetic construct
SEQUENCE: 191
ADDQNPWRAY LXLLFPTXTL LLDLLW                                        26

SEQ ID NO: 192          moltype = AA  length = 26
```

-continued

```
FEATURE                 Location/Qualifiers
REGION                  1..26
                        note = Description of Artificial Sequence: Synthetic peptide
MOD_RES                 18
                        note = Aad
MOD_RES                 23
                        note = Aad
source                  1..26
                        mol_type = protein
                        organism = synthetic construct
SEQUENCE: 192
ADDQNPWRAY LDLLFPTXTL LLXLLW                                       26

SEQ ID NO: 193          moltype = AA  length = 26
FEATURE                 Location/Qualifiers
REGION                  1..26
                        note = Description of Artificial Sequence: Synthetic peptide
MOD_RES                 12
                        note = Aad
MOD_RES                 18
                        note = Aad
MOD_RES                 23
                        note = Aad
source                  1..26
                        mol_type = protein
                        organism = synthetic construct
SEQUENCE: 193
ADDQNPWRAY LXLLFPTXTL LLXLLW                                       26

SEQ ID NO: 194          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 18
                        note = Aad
source                  1..26
                        mol_type = protein
                        organism = synthetic construct
SEQUENCE: 194
ADDQNPWRAY LXLLFPTXTL LLDLLW                                       26

SEQ ID NO: 195          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 23
                        note = Aad
source                  1..26
                        mol_type = protein
                        organism = synthetic construct
SEQUENCE: 195
ADDQNPWRAY LXLLFPTDTL LLXLLW                                       26

SEQ ID NO: 196          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 18
                        note = gamma-carboxyglutamic acid
MOD_RES                 23
                        note = Aad
source                  1..26
                        mol_type = protein
                        organism = synthetic construct
SEQUENCE: 196
ADDQNPWRAY LXLLFPTXTL LLXLLW                                       26

SEQ ID NO: 197          moltype = AA  length = 26
FEATURE                 Location/Qualifiers
REGION                  1..26
                        note = Description of Artificial Sequence: Synthetic peptide
MOD_RES                 12
                        note = Aad
```

```
MOD_RES                 18
                        note = gamma-carboxyglutamic acid
source                  1..26
                        mol_type = protein
                        organism = synthetic construct
SEQUENCE: 197
ADDQNPWRAY LXLLFPTXTL LLDLLW                                       26

SEQ ID NO: 198          moltype = AA  length = 26
FEATURE                 Location/Qualifiers
REGION                  1..26
                        note = Description of Artificial Sequence: Synthetic peptide
MOD_RES                 12
                        note = Aad
MOD_RES                 23
                        note = gamma-carboxyglutamic acid
source                  1..26
                        mol_type = protein
                        organism = synthetic construct
SEQUENCE: 198
ADDQNPWRAY LXLLFPTDTL LLXLLW                                       26

SEQ ID NO: 199          moltype = AA  length = 26
FEATURE                 Location/Qualifiers
REGION                  1..26
                        note = Description of Artificial Sequence: Synthetic peptide
MOD_RES                 12
                        note = gamma-carboxyglutamic acid
MOD_RES                 18
                        note = Aad
MOD_RES                 23
                        note = gamma-carboxyglutamic acid
source                  1..26
                        mol_type = protein
                        organism = synthetic construct
SEQUENCE: 199
ADDQNPWRAY LXLLFPTXTL LLXLLW                                       26

SEQ ID NO: 200          moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 200
GEEQNPWLGA YLDLLFPLEL LGLLELGLW                                    29

SEQ ID NO: 201          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 201
ADDDDDDPWQ AYLDLLFPTD TLLLDLLW                                     28

SEQ ID NO: 202          moltype = AA  length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 202
AEEQNPWRAY LELLFPTETL LLELLW                                       26

SEQ ID NO: 203          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 203
ADDQNPWARY LDWLFPTDTL LLDL                                         24

SEQ ID NO: 204          moltype = AA  length = 23
```

-continued

```
FEATURE                Location/Qualifiers
REGION                 1..23
                       note = Description of Artificial Sequence: Synthetic peptide
source                 1..23
                       mol_type = protein
                       organism = synthetic construct
SEQUENCE: 204
DNNNPWRAYL DLLFPTDTLL LDW                                         23

SEQ ID NO: 205         moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 205
AEEQNPWARY LEWLFPTETL LLEL                                        24

SEQ ID NO: 206         moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 206
DDDDDDPWQA YLDLFPTDTL ALDLW                                       25

SEQ ID NO: 207         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 207
EEQQPWAQYL ELLFPTETLL LEW                                         23

SEQ ID NO: 208         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 208
EEQQPWRAYL ELLFPTETLL LEW                                         23

SEQ ID NO: 209         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 209
AEDQNPWARY ADWLFPTTLL LLD                                         23

SEQ ID NO: 210         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 210
AEEQNPWARY AEWLFPTTLL LLE                                         23

SEQ ID NO: 211         moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 211
AEDQNPWARY ADLLFPTTLA W                                           21
```

-continued

```
SEQ ID NO: 212         moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 212
AEEQNPWARY AELLFPTTLA W                                                    21

SEQ ID NO: 213         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 213
DDDDDNPNYW ARYANWLFTT PLLLLNGALL VEAEET                                    36

SEQ ID NO: 214         moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 214
DDDDDNPNYW ARYAPWLFTT PLLLLPGALL VEAEET                                    36

SEQ ID NO: 215         moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 215
AEQNPIYFAR YADFLFTTPL LLLDLALLWD ADET                                      34

SEQ ID NO: 216         moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 216
AEQNPIYWAR YADFLFTTPL LLLDLALLVD ADET                                      34

SEQ ID NO: 217         moltype = AA  length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 217
AEQNPIYWAR YADWLFTTPL                                                      20

SEQ ID NO: 218         moltype = AA  length = 22
FEATURE                Location/Qualifiers
REGION                 1..22
                       note = Description of Artificial Sequence: Synthetic peptide
source                 1..22
                       mol_type = protein
                       organism = synthetic construct
SEQUENCE: 218
AEQNPIYFAR YADLLFPTTL AW                                                   22

SEQ ID NO: 219         moltype = AA  length = 22
FEATURE                Location/Qualifiers
REGION                 1..22
                       note = Description of Artificial Sequence: Synthetic peptide
source                 1..22
```

```
                        mol_type = protein
                        organism = synthetic construct
SEQUENCE: 219
AEQNPIYWAR YADLLFPTTL AF                                      22

SEQ ID NO: 220          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 220
AEQNPIYWAR YADLLFPTTL AW                                      22

SEQ ID NO: 221          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 221
AEQNPIYFAR YADWLFTTPL                                         20

SEQ ID NO: 222          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 222
EDQNPWARYA DLLFPTTLAW                                         20

SEQ ID NO: 223          moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 223
GLAGLAGLLG LEGLLGLPLG LLEGLWLGLE LEGN                         34

SEQ ID NO: 224          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 224
EQNPIYILDL VFGLLFAVTS VDFLVQWDDA GD                           32

SEQ ID NO: 225          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 225
NLEGFFATLG GEIALWSLVV LAIE                                    24

SEQ ID NO: 226          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 226
NNEGFFATLG GEIALWSDVV LAIE                                    24

SEQ ID NO: 227          moltype = AA  length = 25
FEATURE                 Location/Qualifiers
```

-continued

```
REGION                 1..25
                       note = Description of Artificial Sequence: Synthetic peptide
source                 1..25
                       mol_type = protein
                       organism = synthetic construct
SEQUENCE: 227
DNNEGFFATL GGEIPLWSDV VLAIE                                   25

SEQ ID NO: 228         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 228
WEWEWEWC                                                      8

SEQ ID NO: 229         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 229
WEWEWEWEWC                                                    10

SEQ ID NO: 230         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 230
WEWEWEWEWE WC                                                 12

SEQ ID NO: 231         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 231
LELELELEWC                                                    10

SEQ ID NO: 232         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 232
EEEEWWWWWC                                                    10

SEQ ID NO: 233         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 233
CWEWEWEWEW                                                    10

SEQ ID NO: 234         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 234
RRRRWWWWWC                                                    10

SEQ ID NO: 235         moltype = AA  length = 9
```

-continued

```
FEATURE                Location/Qualifiers
REGION                 1..9
                       note = Description of Artificial Sequence: Synthetic peptide
source                 1..9
                       mol_type = protein
                       organism = synthetic construct
SEQUENCE: 235
EEEWWWWWC                                                                    9

SEQ ID NO: 236         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 236
EWEWWWWEC                                                                    9

SEQ ID NO: 237         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 237
EWWEWWWEC                                                                    9

SEQ ID NO: 238         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 238
EWWWEWWEC                                                                    9

SEQ ID NO: 239         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 239
EWWWWEWEC                                                                    9

SEQ ID NO: 240         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 240
EWWWWWEEC                                                                    9

SEQ ID NO: 241         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 241
EWEEWWWWC                                                                    9

SEQ ID NO: 242         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 242
EWWEEWWWC                                                                    9
```

```
SEQ ID NO: 243          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 243
EWWWEEWWC                                                    9

SEQ ID NO: 244          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 244
EWWWWEEWC                                                    9

SEQ ID NO: 245          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 245
WEEEWWWWC                                                    9

SEQ ID NO: 246          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 246
WWEEEWWWC                                                    9

SEQ ID NO: 247          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 247
WWWEEEWWC                                                    9

SEQ ID NO: 248          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 248
WWWWEEEWC                                                    9

SEQ ID NO: 249          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 249
WEWEEWWWC                                                    9

SEQ ID NO: 250          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 250
WEWWEEWWC                                                    9
```

-continued

```
SEQ ID NO: 251          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 251
WEWWWEEWC                                                         9

SEQ ID NO: 252          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 252
WEWWWWEEC                                                         9

SEQ ID NO: 253          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 253
EEEWWWWW                                                          8

SEQ ID NO: 254          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 254
EWEWWWWE                                                          8

SEQ ID NO: 255          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 255
EWWEWWWE                                                          8

SEQ ID NO: 256          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 256
EWWWEWWE                                                          8

SEQ ID NO: 257          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 257
EWWWWEWE                                                          8

SEQ ID NO: 258          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 258
```

```
EWWWWWEE                                                          8

SEQ ID NO: 259          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 259
EWEEWWWW                                                          8

SEQ ID NO: 260          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 260
EWWEEWWW                                                          8

SEQ ID NO: 261          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 261
EWWWEEWW                                                          8

SEQ ID NO: 262          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 262
EWWWWEEW                                                          8

SEQ ID NO: 263          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 263
WEEEWWWW                                                          8

SEQ ID NO: 264          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 264
WWEEEWWW                                                          8

SEQ ID NO: 265          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 265
WWWEEEWW                                                          8

SEQ ID NO: 266          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

```
SEQUENCE: 266
WWWWEEEW                                                      8

SEQ ID NO: 267          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 267
WEWEEWWW                                                      8

SEQ ID NO: 268          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 268
WEWWEEWW                                                      8

SEQ ID NO: 269          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 269
WEWWWEEW                                                      8

SEQ ID NO: 270          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 270
WEWWWWEE                                                      8

SEQ ID NO: 271          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 271
DDDWWWWWC                                                     9

SEQ ID NO: 272          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 272
DWDWWWWDC                                                     9

SEQ ID NO: 273          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 273
DWWDWWWDC                                                     9

SEQ ID NO: 274          moltype = AA  length = 9
FEATURE                 Location/Qualifiers
REGION                  1..9
                        note = Description of Artificial Sequence: Synthetic peptide
source                  1..9
                        mol_type = protein
```

```
                        organism = synthetic construct
SEQUENCE: 274
DWWWDWWDC                                                  9

SEQ ID NO: 275          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 275
DWWWWDWDC                                                  9

SEQ ID NO: 276          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 276
DWWWWWDDC                                                  9

SEQ ID NO: 277          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 277
DWDDWWWWC                                                  9

SEQ ID NO: 278          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 278
DWWDDWWWC                                                  9

SEQ ID NO: 279          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 279
DWWWDDWWC                                                  9

SEQ ID NO: 280          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 280
DWWWWDDWC                                                  9

SEQ ID NO: 281          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 281
WDDDWWWWC                                                  9

SEQ ID NO: 282          moltype = AA  length = 9
FEATURE                 Location/Qualifiers
REGION                  1..9
                        note = Description of Artificial Sequence: Synthetic peptide
source                  1..9
```

```
                         mol_type = protein
                         organism = synthetic construct
SEQUENCE: 282
WWDDDWWWC                                                                9

SEQ ID NO: 283           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 283
WWWDDDWWC                                                                9

SEQ ID NO: 284           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 284
WWWWDDDWC                                                                9

SEQ ID NO: 285           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 285
WDWDDWWWC                                                                9

SEQ ID NO: 286           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 286
WDWWDDWWC                                                                9

SEQ ID NO: 287           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 287
WDWWWDDWC                                                                9

SEQ ID NO: 288           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 288
WDWWWWDDC                                                                9

SEQ ID NO: 289           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 289
DDDWWWWW                                                                 8

SEQ ID NO: 290           moltype = AA  length = 8
FEATURE                  Location/Qualifiers
REGION                   1..8
                         note = Description of Artificial Sequence: Synthetic peptide
```

-continued

```
source                  1..8
                        mol_type = protein
                        organism = synthetic construct
SEQUENCE: 290
DWDWWWWD                                                              8

SEQ ID NO: 291          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 291
DWWDWWWD                                                              8

SEQ ID NO: 292          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 292
DWWWDWWD                                                              8

SEQ ID NO: 293          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 293
DWWWWDWD                                                              8

SEQ ID NO: 294          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 294
DWWWWWDD                                                              8

SEQ ID NO: 295          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 295
DWDDWWWW                                                              8

SEQ ID NO: 296          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 296
DWWDDWWW                                                              8

SEQ ID NO: 297          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 297
DWWWDDWW                                                              8

SEQ ID NO: 298          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 298
DWWWWDDW                                                                  8

SEQ ID NO: 299          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 299
WDDDWWWW                                                                  8

SEQ ID NO: 300          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 300
WWDDDWWW                                                                  8

SEQ ID NO: 301          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 301
WWWDDDWW                                                                  8

SEQ ID NO: 302          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 302
WWWWDDDW                                                                  8

SEQ ID NO: 303          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 303
WDWDDWWW                                                                  8

SEQ ID NO: 304          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 304
WDWWDDWW                                                                  8

SEQ ID NO: 305          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 305
WDWWWDDW                                                                  8

SEQ ID NO: 306          moltype = AA  length = 8
FEATURE                 Location/Qualifiers
```

-continued

```
REGION                  1..8
                        note = Description of Artificial Sequence: Synthetic peptide
source                  1..8
                        mol_type = protein
                        organism = synthetic construct
SEQUENCE: 306
WDWWWWDD                                                                    8

SEQ ID NO: 307          moltype = AA  length = 8
FEATURE                 Location/Qualifiers
REGION                  1..8
                        note = Description of Artificial Sequence: Synthetic peptide
MOD_RES                 1..3
                        note = gamma-carboxyglutamic acid
source                  1..8
                        mol_type = protein
                        organism = synthetic construct
SEQUENCE: 307
XXXWWWWW                                                                    8

SEQ ID NO: 308          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 3
                        note = gamma-carboxyglutamic acid
MOD_RES                 8
                        note = gamma-carboxyglutamic acid
source                  1..8
                        mol_type = protein
                        organism = synthetic construct
SEQUENCE: 308
XWXWWWWX                                                                    8

SEQ ID NO: 309          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 4
                        note = gamma-carboxyglutamic acid
MOD_RES                 8
                        note = gamma-carboxyglutamic acid
source                  1..8
                        mol_type = protein
                        organism = synthetic construct
SEQUENCE: 309
XWWXWWWX                                                                    8

SEQ ID NO: 310          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 5
                        note = gamma-carboxyglutamic acid
MOD_RES                 8
                        note = gamma-carboxyglutamic acid
source                  1..8
                        mol_type = protein
                        organism = synthetic construct
SEQUENCE: 310
XWWWXWWX                                                                    8

SEQ ID NO: 311          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 6
                        note = gamma-carboxyglutamic acid
MOD_RES                 8
                        note = gamma-carboxyglutamic acid
source                  1..8
```

```
                        mol_type = protein
                        organism = synthetic construct
SEQUENCE: 311
XWWWWXWX                                                    8

SEQ ID NO: 312          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 7..8
                        note = gamma-carboxyglutamic acid
source                  1..8
                        mol_type = protein
                        organism = synthetic construct
SEQUENCE: 312
XWWWWWXX                                                    8

SEQ ID NO: 313          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 3..4
                        note = gamma-carboxyglutamic acid
source                  1..8
                        mol_type = protein
                        organism = synthetic construct
SEQUENCE: 313
XWXXWWWW                                                    8

SEQ ID NO: 314          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 4..5
                        note = gamma-carboxyglutamic acid
source                  1..8
                        mol_type = protein
                        organism = synthetic construct
SEQUENCE: 314
XWWXXWWW                                                    8

SEQ ID NO: 315          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 5..6
                        note = gamma-carboxyglutamic acid
source                  1..8
                        mol_type = protein
                        organism = synthetic construct
SEQUENCE: 315
XWWWXXWW                                                    8

SEQ ID NO: 316          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 6..7
                        note = gamma-carboxyglutamic acid
source                  1..8
                        mol_type = protein
                        organism = synthetic construct
SEQUENCE: 316
XWWWWXXW                                                    8

SEQ ID NO: 317          moltype = AA  length = 8
FEATURE                 Location/Qualifiers
REGION                  1..8
                        note = Description of Artificial Sequence: Synthetic peptide
```

```
MOD_RES                 2..4
                        note = gamma-carboxyglutamic acid
source                  1..8
                        mol_type = protein
                        organism = synthetic construct
SEQUENCE: 317
WXXXWWWW                                                                  8

SEQ ID NO: 318          moltype = AA  length = 8
FEATURE                 Location/Qualifiers
REGION                  1..8
                        note = Description of Artificial Sequence: Synthetic peptide
MOD_RES                 3..5
                        note = gamma-carboxyglutamic acid
source                  1..8
                        mol_type = protein
                        organism = synthetic construct
SEQUENCE: 318
WWXXXWWW                                                                  8

SEQ ID NO: 319          moltype = AA  length = 8
FEATURE                 Location/Qualifiers
REGION                  1..8
                        note = Description of Artificial Sequence: Synthetic peptide
MOD_RES                 4..6
                        note = gamma-carboxyglutamic acid
source                  1..8
                        mol_type = protein
                        organism = synthetic construct
SEQUENCE: 319
WWWXXXWW                                                                  8

SEQ ID NO: 320          moltype = AA  length = 8
FEATURE                 Location/Qualifiers
REGION                  1..8
                        note = Description of Artificial Sequence: Synthetic peptide
MOD_RES                 5..7
                        note = gamma-carboxyglutamic acid
source                  1..8
                        mol_type = protein
                        organism = synthetic construct
SEQUENCE: 320
WWWWXXXW                                                                  8

SEQ ID NO: 321          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 4..5
                        note = gamma-carboxyglutamic acid
source                  1..8
                        mol_type = protein
                        organism = synthetic construct
SEQUENCE: 321
WXWXXWWW                                                                  8

SEQ ID NO: 322          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 5..6
                        note = gamma-carboxyglutamic acid
source                  1..8
                        mol_type = protein
                        organism = synthetic construct
SEQUENCE: 322
WXWWXXWW                                                                  8

SEQ ID NO: 323          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 6..7
```

```
                        note = gamma-carboxyglutamic acid
source                  1..8
                        mol_type = protein
                        organism = synthetic construct
SEQUENCE: 323
WXWWWXXW                                                    8

SEQ ID NO: 324          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 7..8
                        note = gamma-carboxyglutamic acid
source                  1..8
                        mol_type = protein
                        organism = synthetic construct
SEQUENCE: 324
WXWWWWXX                                                    8

SEQ ID NO: 325          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 325
EEEWWWWC                                                    8

SEQ ID NO: 326          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 326
EWEWWWEC                                                    8

SEQ ID NO: 327          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 327
EWWEWWEC                                                    8

SEQ ID NO: 328          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 328
EWWWEWEC                                                    8

SEQ ID NO: 329          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 329
EWWWWEEC                                                    8

SEQ ID NO: 330          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 330
```

```
EWEEWWWC                                                        8

SEQ ID NO: 331          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 331
EWWEEWWC                                                        8

SEQ ID NO: 332          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 332
EWWWEEWC                                                        8

SEQ ID NO: 333          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 333
EWWWWEEC                                                        8

SEQ ID NO: 334          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 334
WEEEWWWC                                                        8

SEQ ID NO: 335          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 335
WWEEEWWC                                                        8

SEQ ID NO: 336          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 336
WWWEEEWC                                                        8

SEQ ID NO: 337          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 337
WWWWEEEC                                                        8

SEQ ID NO: 338          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

```
SEQUENCE: 338
WEWEEWWC                                                                  8

SEQ ID NO: 339          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 339
WEWWEEWC                                                                  8

SEQ ID NO: 340          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 340
WEWWWEEC                                                                  8

SEQ ID NO: 341          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 341
EEEWWWW                                                                   7

SEQ ID NO: 342          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 342
EWEWWWE                                                                   7

SEQ ID NO: 343          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 343
EWWEWWE                                                                   7

SEQ ID NO: 344          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 344
EWWWEWE                                                                   7

SEQ ID NO: 345          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 345
EWWWWEE                                                                   7

SEQ ID NO: 346          moltype = AA  length = 7
FEATURE                 Location/Qualifiers
REGION                  1..7
                        note = Description of Artificial Sequence: Synthetic peptide
source                  1..7
                        mol_type = protein
```

```
                         organism = synthetic construct
SEQUENCE: 346
EWEEWWW                                                                      7

SEQ ID NO: 347           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 347
EWWEEWW                                                                      7

SEQ ID NO: 348           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 348
EWWWEEW                                                                      7

SEQ ID NO: 349           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 349
EWWWWEE                                                                      7

SEQ ID NO: 350           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 350
WEEEWWW                                                                      7

SEQ ID NO: 351           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 351
WWEEEWW                                                                      7

SEQ ID NO: 352           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 352
WWWEEEW                                                                      7

SEQ ID NO: 353           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 353
WWWWEEE                                                                      7

SEQ ID NO: 354           moltype = AA  length = 7
FEATURE                  Location/Qualifiers
REGION                   1..7
                         note = Description of Artificial Sequence: Synthetic peptide
source                   1..7
```

```
                        mol_type = protein
                        organism = synthetic construct
SEQUENCE: 354
WEWEEWW                                                   7

SEQ ID NO: 355          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 355
WEWWEEW                                                   7

SEQ ID NO: 356          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 356
WEWWWEE                                                   7

SEQ ID NO: 357          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 357
DDDWWWWC                                                  8

SEQ ID NO: 358          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 358
DWDWWWDC                                                  8

SEQ ID NO: 359          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 359
DWWDWWDC                                                  8

SEQ ID NO: 360          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 360
DWWWDWDC                                                  8

SEQ ID NO: 361          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 361
DWWWWDDC                                                  8

SEQ ID NO: 362          moltype = AA  length = 8
FEATURE                 Location/Qualifiers
REGION                  1..8
                        note = Description of Artificial Sequence: Synthetic peptide
```

```
source                  1..8
                        mol_type = protein
                        organism = synthetic construct
SEQUENCE: 362
DWDDWWWC                                                                    8

SEQ ID NO: 363          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 363
DWWDDWWC                                                                    8

SEQ ID NO: 364          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 364
DWWWDDWC                                                                    8

SEQ ID NO: 365          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 365
DWWWWDDC                                                                    8

SEQ ID NO: 366          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 366
WDDDWWWC                                                                    8

SEQ ID NO: 367          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 367
WWDDDWWC                                                                    8

SEQ ID NO: 368          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 368
WWWDDDWC                                                                    8

SEQ ID NO: 369          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 369
WWWWDDDC                                                                    8

SEQ ID NO: 370          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 370
WDWDDWWC                                                                  8

SEQ ID NO: 371          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 371
WDWWDDWC                                                                  8

SEQ ID NO: 372          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 372
WDWWWDDC                                                                  8

SEQ ID NO: 373          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 373
DDDWWWW                                                                   7

SEQ ID NO: 374          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 374
DWDWWWD                                                                   7

SEQ ID NO: 375          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 375
DWWDWWD                                                                   7

SEQ ID NO: 376          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 376
DWWWDWD                                                                   7

SEQ ID NO: 377          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 377
DWWWWDD                                                                   7

SEQ ID NO: 378          moltype = AA  length = 7
FEATURE                 Location/Qualifiers
```

```
REGION                 1..7
                       note = Description of Artificial Sequence: Synthetic peptide
source                 1..7
                       mol_type = protein
                       organism = synthetic construct
SEQUENCE: 378
DWDDWWW                                                            7

SEQ ID NO: 379         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 379
DWWDDWW                                                            7

SEQ ID NO: 380         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 380
DWWWDDW                                                            7

SEQ ID NO: 381         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 381
DWWWWDD                                                            7

SEQ ID NO: 382         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 382
WDDDWWW                                                            7

SEQ ID NO: 383         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 383
WWDDDWW                                                            7

SEQ ID NO: 384         moltype =   length =
SEQUENCE: 384
000

SEQ ID NO: 385         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 385
WWWDDDW                                                            7

SEQ ID NO: 386         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
```

```
SEQUENCE: 386
WWWWDDD                                                         7

SEQ ID NO: 387          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 387
WDWDDWW                                                         7

SEQ ID NO: 388          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 388
WDWWDDW                                                         7

SEQ ID NO: 389          moltype =   length =
SEQUENCE: 389
000

SEQ ID NO: 390          moltype =   length =
SEQUENCE: 390
000

SEQ ID NO: 391          moltype =   length =
SEQUENCE: 391
000

SEQ ID NO: 392          moltype =   length =
SEQUENCE: 392
000

SEQ ID NO: 393          moltype =   length =
SEQUENCE: 393
000

SEQ ID NO: 394          moltype =   length =
SEQUENCE: 394
000

SEQ ID NO: 395          moltype =   length =
SEQUENCE: 395
000

SEQ ID NO: 396          moltype =   length =
SEQUENCE: 396
000

SEQ ID NO: 397          moltype =   length =
SEQUENCE: 397
000

SEQ ID NO: 398          moltype =   length =
SEQUENCE: 398
000

SEQ ID NO: 399          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 399
WDWWWDD                                                         7

SEQ ID NO: 400          moltype = AA  length = 7
FEATURE                 Location/Qualifiers
REGION                  1..7
                        note = Description of Artificial Sequence: Synthetic peptide
MOD_RES                 1..3
                        note = gamma-carboxyglutamic acid
```

-continued

```
source                  1..7
                        mol_type = protein
                        organism = synthetic construct
SEQUENCE: 400
XXXWWWW                                                                    7

SEQ ID NO: 401          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 3
                        note = gamma-carboxyglutamic acid
MOD_RES                 7
                        note = gamma-carboxyglutamic acid
source                  1..7
                        mol_type = protein
                        organism = synthetic construct
SEQUENCE: 401
XWXWWWX                                                                    7

SEQ ID NO: 402          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 4
                        note = gamma-carboxyglutamic acid
MOD_RES                 7
                        note = gamma-carboxyglutamic acid
source                  1..7
                        mol_type = protein
                        organism = synthetic construct
SEQUENCE: 402
XWWXWWX                                                                    7

SEQ ID NO: 403          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 5
                        note = gamma-carboxyglutamic acid
MOD_RES                 7
                        note = gamma-carboxyglutamic acid
source                  1..7
                        mol_type = protein
                        organism = synthetic construct
SEQUENCE: 403
XWWWXWX                                                                    7

SEQ ID NO: 404          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 6..7
                        note = gamma-carboxyglutamic acid
source                  1..7
                        mol_type = protein
                        organism = synthetic construct
SEQUENCE: 404
XWWWWXX                                                                    7

SEQ ID NO: 405          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 3..4
                        note = gamma-carboxyglutamic acid
source                  1..7
                        mol_type = protein
                        organism = synthetic construct
```

```
SEQUENCE: 405
XWXXWWW                                                      7

SEQ ID NO: 406          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 4..5
                        note = gamma-carboxyglutamic acid
source                  1..7
                        mol_type = protein
                        organism = synthetic construct
SEQUENCE: 406
XWWXXWW                                                      7

SEQ ID NO: 407          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 5..6
                        note = gamma-carboxyglutamic acid
source                  1..7
                        mol_type = protein
                        organism = synthetic construct
SEQUENCE: 407
XWWWXXW                                                      7

SEQ ID NO: 408          moltype = AA  length = 7
FEATURE                 Location/Qualifiers
REGION                  1..7
                        note = Description of Artificial Sequence: Synthetic peptide
MOD_RES                 1
                        note = gamma-carboxyglutamic acid
MOD_RES                 6..7
                        note = gamma-carboxyglutamic acid
source                  1..7
                        mol_type = protein
                        organism = synthetic construct
SEQUENCE: 408
XWWWWXX                                                      7

SEQ ID NO: 409          moltype = AA  length = 7
FEATURE                 Location/Qualifiers
REGION                  1..7
                        note = Description of Artificial Sequence: Synthetic peptide
MOD_RES                 2..4
                        note = gamma-carboxyglutamic acid
source                  1..7
                        mol_type = protein
                        organism = synthetic construct
SEQUENCE: 409
WXXXWWW                                                      7

SEQ ID NO: 410          moltype = AA  length = 7
FEATURE                 Location/Qualifiers
REGION                  1..7
                        note = Description of Artificial Sequence: Synthetic peptide
MOD_RES                 3..5
                        note = gamma-carboxyglutamic acid
source                  1..7
                        mol_type = protein
                        organism = synthetic construct
SEQUENCE: 410
WWXXXWW                                                      7

SEQ ID NO: 411          moltype = AA  length = 7
FEATURE                 Location/Qualifiers
REGION                  1..7
                        note = Description of Artificial Sequence: Synthetic peptide
MOD_RES                 4..6
                        note = gamma-carboxyglutamic acid
source                  1..7
                        mol_type = protein
                        organism = synthetic construct
SEQUENCE: 411
```

```
WWWXXXW                                                                  7

SEQ ID NO: 412          moltype = AA  length = 7
FEATURE                 Location/Qualifiers
REGION                  1..7
                        note = Description of Artificial Sequence: Synthetic peptide
MOD_RES                 5..7
                        note = gamma-carboxyglutamic acid
source                  1..7
                        mol_type = protein
                        organism = synthetic construct
SEQUENCE: 412
WWWWXXX                                                                  7

SEQ ID NO: 413          moltype = AA  length = 7
FEATURE                 Location/Qualifiers
REGION                  1..7
                        note = Description of Artificial Sequence: Synthetic peptide
MOD_RES                 2
                        note = gamma-carboxyglutamic acid
MOD_RES                 4..5
                        note = gamma-carboxyglutamic acid
source                  1..7
                        mol_type = protein
                        organism = synthetic construct
SEQUENCE: 413
WXWXXWW                                                                  7

SEQ ID NO: 414          moltype = AA  length = 7
FEATURE                 Location/Qualifiers
REGION                  1..7
                        note = Description of Artificial Sequence: Synthetic peptide
MOD_RES                 2
                        note = gamma-carboxyglutamic acid
MOD_RES                 5..6
                        note = Gla
source                  1..7
                        mol_type = protein
                        organism = synthetic construct
SEQUENCE: 414
WXWWXXW                                                                  7

SEQ ID NO: 415          moltype = AA  length = 7
FEATURE                 Location/Qualifiers
REGION                  1..7
                        note = Description of Artificial Sequence: Synthetic peptide
MOD_RES                 2
                        note = gamma-carboxyglutamic acid
MOD_RES                 6..7
                        note = gamma-carboxyglutamic acid
source                  1..7
                        mol_type = protein
                        organism = synthetic construct
SEQUENCE: 415
WXWWWXX                                                                  7

SEQ ID NO: 416          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 416
WEWEWEWC                                                                 8

SEQ ID NO: 417          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 417
EWEWEWWC                                                                 8

SEQ ID NO: 418          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 418
WDWDWDWC                                                                     8

SEQ ID NO: 419          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 419
DWDWDWWC                                                                     8

SEQ ID NO: 420          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 4
                        note = gamma-carboxyglutamic acid
source                  1..8
                        mol_type = protein
                        organism = synthetic construct
SEQUENCE: 420
WXWXWDWC                                                                     8

SEQ ID NO: 421          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 421
DWDWDWDC                                                                     8

SEQ ID NO: 422          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 422
WEWEWEWE                                                                     8

SEQ ID NO: 423          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 423
EWEWEWEW                                                                     8

SEQ ID NO: 424          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 424
WDWDWDWD                                                                     8

SEQ ID NO: 425          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 425
```

-continued

```
DWDWDWDW                                                            8

SEQ ID NO: 426          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 4
                        note = gamma-carboxyglutamic acid
MOD_RES                 6
                        note = gamma-carboxyglutamic acid
MOD_RES                 8
                        note = gamma-carboxyglutamic acid
source                  1..8
                        mol_type = protein
                        organism = synthetic construct
SEQUENCE: 426
WXWXWXWX                                                            8

SEQ ID NO: 427          moltype = AA  length = 8
FEATURE                 Location/Qualifiers
REGION                  1..8
                        note = Description of Artificial Sequence: Synthetic peptide
MOD_RES                 1
                        note = gamma-carboxyglutamic acid
MOD_RES                 3
                        note = gamma-carboxyglutamic acid
MOD_RES                 5
                        note = gamma-carboxyglutamic acid
MOD_RES                 7
                        note = gamma-carboxyglutamic acid
source                  1..8
                        mol_type = protein
                        organism = synthetic construct
SEQUENCE: 427
XWXWXWXW                                                            8

SEQ ID NO: 428          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 428
CWEWEWEWEW                                                          10

SEQ ID NO: 429          moltype = AA  length = 8
FEATURE                 Location/Qualifiers
REGION                  1..8
                        note = Description of Artificial Sequence: Synthetic peptide
MOD_RES                 2
                        note = gamma-carboxyglutamic acid
MOD_RES                 4
                        note = gamma-carboxyglutamic acid
source                  1..8
                        mol_type = protein
                        organism = synthetic construct
SEQUENCE: 429
WXWXWDWC                                                            8

SEQ ID NO: 430          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 430
EWEWEWEC                                                            8

SEQ ID NO: 431          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

```
SEQUENCE: 431
DWDWDWDC                                                                 8

SEQ ID NO: 432          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 432
EEEEEK                                                                   6

SEQ ID NO: 433          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 433
WWWWWC                                                                   6

SEQ ID NO: 434          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 434
EEEEK                                                                    5

SEQ ID NO: 435          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 435
WWWWWC                                                                   6

SEQ ID NO: 436          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 436
EEEEEK                                                                   6

SEQ ID NO: 437          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 437
WWWWC                                                                    5

SEQ ID NO: 438          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 438
EEEEK                                                                    5

SEQ ID NO: 439          moltype = AA  length = 5
FEATURE                 Location/Qualifiers
REGION                  1..5
                        note = Description of Artificial Sequence: Synthetic peptide
source                  1..5
                        mol_type = protein
```

```
                     organism = synthetic construct
SEQUENCE: 439
WWWWC                                                              5

SEQ ID NO: 440       moltype = AA  length = 6
FEATURE              Location/Qualifiers
REGION               1..6
                     note = Description of Artificial Sequence: Synthetic peptide
source               1..6
                     mol_type = protein
                     organism = synthetic construct
SEQUENCE: 440
EEEEEK                                                             6

SEQ ID NO: 441       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 441
WWWWW                                                              5

SEQ ID NO: 442       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 442
EEEEK                                                              5

SEQ ID NO: 443       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 443
WWWWW                                                              5

SEQ ID NO: 444       moltype = AA  length = 6
FEATURE              Location/Qualifiers
REGION               1..6
                     note = Description of Artificial Sequence: Synthetic peptide
source               1..6
                     mol_type = protein
                     organism = synthetic construct
SEQUENCE: 444
EEEEEK                                                             6

SEQ ID NO: 445       moltype = AA  length = 4
FEATURE              Location/Qualifiers
REGION               1..4
                     note = Description of Artificial Sequence: Synthetic peptide
source               1..4
                     mol_type = protein
                     organism = synthetic construct
SEQUENCE: 445
WWWW                                                               4

SEQ ID NO: 446       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 446
EEEEK                                                              5

SEQ ID NO: 447       moltype = AA  length = 4
FEATURE              Location/Qualifiers
REGION               1..4
                     note = Description of Artificial Sequence: Synthetic peptide
source               1..4
```

```
                        mol_type = protein
                        organism = synthetic construct
SEQUENCE: 447
WWWW                                                                4

SEQ ID NO: 448          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 448
DDDDDK                                                              6

SEQ ID NO: 449          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 449
WWWWWC                                                              6

SEQ ID NO: 450          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 450
DDDDK                                                               5

SEQ ID NO: 451          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 451
WWWWWC                                                              6

SEQ ID NO: 452          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 452
DDDDDK                                                              6

SEQ ID NO: 453          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 453
WWWWC                                                               5

SEQ ID NO: 454          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 454
DDDDK                                                               5

SEQ ID NO: 455          moltype = AA  length = 5
FEATURE                 Location/Qualifiers
REGION                  1..5
                        note = Description of Artificial Sequence: Synthetic peptide
```

```
source                  1..5
                        mol_type = protein
                        organism = synthetic construct
SEQUENCE: 455
WWWWC                                                                       5

SEQ ID NO: 456          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 456
DDDDDK                                                                      6

SEQ ID NO: 457          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 457
WWWWW                                                                       5

SEQ ID NO: 458          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 458
DDDDK                                                                       5

SEQ ID NO: 459          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 459
WWWWW                                                                       5

SEQ ID NO: 460          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 460
DDDDDK                                                                      6

SEQ ID NO: 461          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 461
WWWW                                                                        4

SEQ ID NO: 462          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 462
DDDDK                                                                       5

SEQ ID NO: 463          moltype = AA  length = 4
FEATURE                 Location/Qualifiers
REGION                  1..4
```

```
                        note = Description of Artificial Sequence: Synthetic peptide
source                  1..4
                        mol_type = protein
                        organism = synthetic construct
SEQUENCE: 463
WWWW                                                                        4

SEQ ID NO: 464          moltype =   length =
SEQUENCE: 464
000

SEQ ID NO: 465          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 465
WWWWWC                                                                      6

SEQ ID NO: 466          moltype =   length =
SEQUENCE: 466
000

SEQ ID NO: 467          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 467
WWWWWC                                                                      6

SEQ ID NO: 468          moltype =   length =
SEQUENCE: 468
000

SEQ ID NO: 469          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 469
WWWWC                                                                       5

SEQ ID NO: 470          moltype =   length =
SEQUENCE: 470
000

SEQ ID NO: 471          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 471
WWWWC                                                                       5

SEQ ID NO: 472          moltype =   length =
SEQUENCE: 472
000

SEQ ID NO: 473          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 473
WWWWW                                                                       5

SEQ ID NO: 474          moltype =   length =
SEQUENCE: 474
```

```
000

SEQ ID NO: 475          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 475
WWWWW                                                                  5

SEQ ID NO: 476          moltype =   length =
SEQUENCE: 476
000

SEQ ID NO: 477          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 477
WWWW                                                                   4

SEQ ID NO: 478          moltype =   length =
SEQUENCE: 478
000

SEQ ID NO: 479          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 479
WWWW                                                                   4

SEQ ID NO: 480          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 480
EEEEEWWWWW C                                                           11

SEQ ID NO: 481          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 481
EEEEWWWWC                                                              9

SEQ ID NO: 482          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 482
WEWEWEWECW                                                             10

SEQ ID NO: 483          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 483
WRWRWRWRWC                                                             10
```

```
SEQ ID NO: 484          moltype = AA  length = 26
FEATURE                 Location/Qualifiers
REGION                  1..26
                        note = Description of Artificial Sequence: Synthetic peptide
MOD_RES                 12
                        note = Aad
MOD_RES                 23
                        note = Aad
source                  1..26
                        mol_type = protein
                        organism = synthetic construct
SEQUENCE: 484
ADDQNPWRAY LXLLFPTDTL LLXLLW                                        26

SEQ ID NO: 485          moltype = AA  length = 1225
FEATURE                 Location/Qualifiers
source                  1..1225
                        mol_type = protein
                        organism = Homo sapiens
SEQUENCE: 485
MKLRLPASPE THLDMLRHLY QGCQVVQGNL ELTYLPTNAS LSFLQDIQEV QGYVLIAHNQ  60
VRQVPLQRLR IVRGTQLFED NYALAVLDNG DPLNNTTPVT GASPGGLREL QLRSLTEILK  120
GGVLIQRNPQ LCYQDTILWK DIFHKNNQLA LTLIDTNRSR ACHPCSPMCK GSRCWGESSE  180
DCQSLTRTVC AGGCARCKGP LPTDCCHEQC AAGCTGPKHS DCLACLHFNH SGICELHCPA  240
LVTYNTDTFE SMPNPEGRYT FGASCVTACP YNYLSTDVGS CTLVCPLHNQ EVTAEDGTQR  300
CEKCSKPCAR VCYGLGMEHL REVRAVTSAN IQEFAGCKKI FGSLAFLPES FDGDPASNTA  360
PLQPEQLQVF ETLEEITGYL YISAWPDSLP DLSVFQNLQV IRGRILHNGA YSLTLQGLGI  420
SWLGLRSLRE LGSGLALIHH NTHLCFVHTV PWDQLFRNPH QALLHTANRP EDECVGEGLA  480
CHQLCARGHC WGPGPTQCVN CSQFLRGQEC VEECRVLQGL PREYVNARHC LPCHPECQPQ  540
NGSVTCFGPE ADQCVACAHY KDPPFCVARC PSGVKPDLSY MPIWKFPDEE GACQPCPINC  600
THSCVDLDDK GCPAEQRASP LTSIISAVVG ILLVVVLGVV FGILIKRRQQ KIRKYTMRRL  660
LQETELVEPL TPSGAMPNQA QMRILKETEL RKVKVLGSGA FGTVYKGIWI PDGENVKIPV  720
AIKVLRENTS PKANKEILDE AYVMAGVGSP YVSRLLGICL TSTVQLVTQL MPYGCLLDHV  780
RENRGRLGSQ DLLNWCMQIA KGMSYLEDVR LVHRDLAARN VLVKSPNHVK ITDFGLARLL  840
DIDETEYHAD GGKVPIKWMA LESILRRRFT HQSDVWSYGV TVWELMTFGA KPYDGIPARE  900
IPDLLEKGER LPQPPICTID VYMIMVKCWM IDSECRPRFR ELVSEFSRMA RDPQRFVVIQ  960
NEDLGPASPL DSTFYRSLLE DDDMGDLVDA EEYLVPQQGF FCPDPAPGAG GMVHHRHRSS  1020
STRSGGGDLT LGLEPSEEEA PRSPLAPSEG AGSDVFDGDL GMGAAKGLQS LPTHDPSPLQ  1080
RYSEDPTVPL PSETDGYVAP LTCSPQPEYV NQPDVRPQPP SPREGPLPAA RPAGATLERP  1140
KTLSPGKNGV VKDVFAFGGA VENPEYLTPQ GGAAPQPHPP PAFSPAFDNL YYWDQDPPER  1200
GAPPSTFKGT PTAENPEYLG LDVPV                                         1225

SEQ ID NO: 486          moltype = DNA  length = 4889
FEATURE                 Location/Qualifiers
source                  1..4889
                        mol_type = other DNA
                        organism = Homo sapiens
SEQUENCE: 486
aagttcctgt gttctttatt ctactctccg ctgaagtcca cacagtttaa attaaagttc  60
ccggattttt gtgggcgcct gccccgcccc tcgtcccccct gctgtgtcca tatatcgagg  120
cgatagggtt aagggaaggc ggacgcctga tgggttaatg agcaaactga agtgttttcc  180
atgatctttt ttgagtcgca attgaagtac cacctcccga gggtgattgc ttccccatgc  240
ggggtagaac ctttgctgtc ctgttcacca ctctacctcc agcacagaat ttggcttatg  300
cctactcaat gtgaagatga tgaggatgaa aacctttgtg atgatccact tccacttaat  360
gaatggtggc aaagcaaagc tatattcaag accacatgca aagctactcc ctgagcaaag  420
agtcacagat aaaacggggg caccagtaga atggccagga caaacgcagt gcagcacaga  480
gactcagacc ctggcagcca tgcctgcgca ggcagtgatg agagtgacat gtactgttgt  540
ggacatgcac aaaagtgagt gtgcaccggc acagacatga agctgcggct ccctgccagt  600
cccgagaccc acctggacat gctccgccac ctctaccagg gctgccaggt ggtgcaggga  660
aacctggaac tcacctacct gcccaccaat gccagcctgt ccttcctgca ggatatccag  720
gaggtgcagg gctacgtgct catcgctcac aaccaagtga ggcaggtccc actgcagagg  780
ctgcggattg tgcgaggcac ccagctcttt gaggacaact atgccctggc cgtgctagac  840
aatggagacc cgctgaacaa taccacccct gtcacagggg cctccccagg aggcctgcgg  900
gagctgcagc ttcgaagcct cacagagatc ttgaaaggag gggtcttgat ccagcggaac  960
ccccagctct gctaccagga cacgattttg tggaaggaca tcttccacaa gaacaaccag  1020
ctggctctca cactgataga caccaaccgc tctcgggcct gccacccctg ttctccgatg  1080
tgtaagggct cccgctgctg gggagagagt tctgaggatt gtcagagcct gacgcgcact  1140
gtctgtgccg gtggctgtgc ccgctgcaag ggcccactgc ccactgactg ctgccatgag  1200
cagtgtgctg ccggctgcac gggccccaag cactctgact gcctggcctg cctccacttc  1260
aaccacagtg gcatctgtga gctgcactgc ccagccctgg tcacctacaa cacagacacg  1320
tttgagtcca tgcccaatcc cgagggccgg tatacattcg gcgccagctg tgtgactgcc  1380
tgtccctaca actacctttc tacggacgtg ggatcctgca ccctcgtctg ccccctgcac  1440
aaccaagagg tgacagcaga ggatggaaca cagcggtgtg agaagtgcag caagccctgt  1500
gccccgagtgt gctatggtct gggcatggag cacttgcgag aggtgagggc agttaccagt  1560
gccaatatcc aggagtttgc tggctgcaag aagatctttg ggagcctggc atttctgccg  1620
gagagctttg atggggaccc agcctccaac actgccccgc tccagccaga gcagctccaa  1680
gtgtttgaga ctctggaaga gatcacaggt tacctataca tctcagcatg gccggacagc  1740
ctgcctgacc tcagcgtctt ccagaacctg caagtaatcc ggggacgaat tctgcacaat  1800
```

```
ggcgcctact cgctgaccct gcaagggctg ggcatcagct ggctggggct gcgctcactg  1860
agggaactgg gcagtggact ggccctcatc caccataaca cccacctctg cttcgtgcac  1920
acggtgccct gggaccagct ctttcggaac ccgcaccaag ctctgctcca cactgccaac  1980
cggccagagg acgagtgtgt gggcgagggc ctggcctgcc accagctgtg cgcccgaggg  2040
cactgctggg gtccagggcc cacccagtgt gtcaactgca gccagttcct tcggggccag  2100
gagtgcgtgg aggaatgccg agtactgcag gggctcccca gggagtatgt gaatgccagg  2160
cactgtttgc cgtgccaccc tgagtgtcag ccccagaatg gctcagtgac ctgttttgga  2220
ccggaggctg accagtgtgt ggcctgtgcc cactataagg accctccctt ctgcgtggcc  2280
cgctgcccca gcggtgtgaa acctgacctc tcctacatgc ccatctggaa gtttccagat  2340
gaggagggcg catgccagcc ttgccccatc aactgcaccc actcctgtgt ggacctggat  2400
gacaagggct gccccgccga gcagagagcc agccctctga cgtccatcat ctctgcggtg  2460
gttggcattc tgctggtcgt ggtcttgggg gtggtctttg ggatcctcat caagcgacgg  2520
cagcagaaga tccggaagta cacgatgcgg agactgctgc aggaaacgga gctggtggag  2580
ccgctgacac ctagcggagc gatgcccaac caggcgcaga tgcggatcct gaaagagacg  2640
gagctgagga aggtgaaggt gcttggatct ggcgcttttg gcacagtcta caagggcatc  2700
tggatccctg atggggagaa tgtgaaaatt ccagtggcca tcaaagtgtt gagggaaaac  2760
acatccccca aagccaacaa agaaatctta gacgaagcat acgtgatggc tggtgtgggc  2820
tccccatatg tctcccgcct tctgggcatc tgcctgacat ccacggtgca gctggtgaca  2880
cagcttatgc cctatggctg cctcttagac catgtccggg aaaaccgcgg acgcctgggc  2940
tcccaggacc tgctgaactg gtgtatgcag attgccaagg ggatgagcta cctggaggat  3000
gtgcggctcg tacacaggga cttggccgct cggaacgtgc tggtcaagag tcccaaccat  3060
gtcaaaatta cagacttcgg gctggctcgg ctgctggaca ttgacgagac agagtaccat  3120
gcagatgggg gcaaggtgcc catcaagtgg atggcgctgg agtccattct ccgccggcgg  3180
ttcacccacc agagtgatgt gtggagttat ggtgtgactg tgtgggagct gatgactttt  3240
ggggccaaac cttacgatgg gatcccagcc cgggagatcc ctgacctgct ggaaaagggg  3300
gagcggctgc cccagccccc catctgcacc attgatgtct acatgatcat ggtcaaatgt  3360
tggatgattg actctgaatg tcggccaaga ttccgggagt tggtgtctga attctcccgc  3420
atggccaggg acccccagcg ctttgtggtc atccagaatg aggacttggg cccagccagt  3480
cccttggaca gcaccttcta ccgctcactg ctggaggacg atgacatggg ggacctggtg  3540
gatgctgagg agtatctggt accccagcag ggcttcttct gtccagaccc tgccccgggc  3600
gctgggggca tggtccacca caggcaccgc agctcatcta ccaggagtgg cggtggggac  3660
ctgacactag ggctggagcc ctctgaagag gaggccccca ggtctccact ggcaccctcc  3720
gaaggggctg gctccgatgt atttgatggt gacctgggaa tgggggcagc caaggggctg  3780
caaagcctcc ccacacatga ccccagccct ctacagcggt acagtgagga ccccacagta  3840
cccctgccct ctgagactga tggctacgtt gcccccctga cctgcagccc ccagcctgaa  3900
tatgtgaacc agccagatgt tcggccccag cccccttcgc cccgagaggg ccctctgcct  3960
gctgcccgac ctgctggtgc cactctggaa aggcccaaga ctctctcccc agggaagaat  4020
ggggtcgtca aagacgtttt tgcctttggg ggtgccgtgg agaaccccga gtacttgaca  4080
ccccagggag gagctgcccc tcagccccac cctcctcctg ccttcagccc agccttcgac  4140
aacctctatt actgggacca ggacccacca gagcgggggg ctccacccag caccttcaaa  4200
gggacaccta cggcagagaa cccagagtac ctgggtctgg acgtgccagt gtgaaccaga  4260
aggccaagtc cgcagaagcc ctgatgtgtc ctcagggagc agggaaggcc tgacttctgc  4320
tggcatcaag aggtgggagg gccctccgac cacttccagg ggaacctgcc atgccaggaa  4380
cctgtcctaa ggaaccttcc ttcctgcttg agttcccaga tggctggaag gggtccagcc  4440
tcgttggaag aggaacagca ctggggagtc tttgtggatt ctgaggccct gcccaatgag  4500
actctagggt ccagtggatg ccacagccca gcttggccct ttccttccag atcctgggta  4560
ctgaaagcct tagggaagct ggcctgagag gggaagcggc cctaagggag tgtctaagaa  4620
caaaagcgac ccattcagag actgtccctg aaacctagta ctgcccccca tgaggaagga  4680
acagcaatgg tgtcagtatc caggctttgt acagagtgct ttctgttta gtttttactt  4740
tttttgtttt gttttttttaa agatgaaata aagacccagg gggagaatgg gtgttgtatg  4800
gggaggcaag tgtggggggt ccttctccac acccactttg tccatttgca aatatatttt  4860
ggaaaacagc taaaaaaaaa aaaaaaaaa                                     4889
```

```
SEQ ID NO: 487         moltype = AA  length = 153
FEATURE                Location/Qualifiers
source                 1..153
                       mol_type = protein
                       organism = Homo sapiens
SEQUENCE: 487
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153
```

```
SEQ ID NO: 488         moltype = DNA  length = 1029
FEATURE                Location/Qualifiers
source                 1..1029
                       mol_type = other DNA
                       organism = Homo sapiens
SEQUENCE: 488
ctatcaccta agtgtgggct aatgtaacaa agagggattt cacctacatc cattcagtca  60
gtctttgggg gtttaaagaa attccaaaga gtcatcagaa gaggaaaaat gaaggtaatg  120
ttttttcaga caggtaaagt ctttgaaaat atgtgtaata tgtaaaacat tttgacaccc  180
ccataatatt tttccagaat taacagtata aattgcatct cttgttcaag agttccctat  240
cactctcttt aatcactact cacagtaacc tcaactcctg ccacaatgta caggatgcaa  300
ctcctgtctt gcattgcact aagtcttgca cttgtcacaa acagtgcacc tacttcaagt  360
tctacaaaga aaacacagct acaactggag catttactgc tggatttaca gatgattttg  420
aatggaatta ataattacaa gaatcccaaa ctcaccagga tgctcacatt taagttttac  480
atgcccaaga aggccacaga actgaaacat cttcagtgtc tagaagaaga actcaaacct  540
ctggaggaag tgctaaattt agctcaaagc aaaaactttc acttaagacc cagggactta  600
```

```
atcagcaata tcaacgtaat agttctggaa ctaaagggat ctgaaacaac attcatgtgt  660
gaatatgctg atgagacagc aaccattgta gaatttctga acagatggat taccttttgt  720
caaagcatca tctcaacact gacttgataa ttaagtgctt cccacttaaa acatatcagg  780
ccttctattt atttaaatat ttaaatttta tatttattgt tgaatgtatg gtttgctacc  840
tattgtaact attattctta atcttaaaac tataaatatg gatcttttat gattcttttt  900
gtaagcccta ggggctctaa aatggtttca cttatttatc ccaaaatatt tattattatg  960
ttgaatgtta aatatagtat ctatgtagat tggttagtaa aactatttaa taaatttgat  1020
aaatataaa                                                          1029

SEQ ID NO: 489         moltype = AA  length = 212
FEATURE                Location/Qualifiers
source                 1..212
                       mol_type = protein
                       organism = Homo sapiens
SEQUENCE: 489
MNSFSTSAFG PVAFSLGLLL VLPAAFPAPV PPGEDSKDVA APHRQPLTSS ERIDKQIRYI  60
LDGISALRKE TCNKSNMCES SKEALAENNL NLPKMAEKDG CFQSGFNEET CLVKIITGLL  120
EFEVYLEYLQ NRFESSEEQA RAVQMSTKVL IQFLQKKAKN LDAITTPDPT TNASLLTKLQ  180
AQNQWLQDMT THLILRSFKE FLQSSLRALR QM                                212

SEQ ID NO: 490         moltype = DNA  length = 1127
FEATURE                Location/Qualifiers
source                 1..1127
                       mol_type = other DNA
                       organism = Homo sapiens
SEQUENCE: 490
attctgccct cgagcccacc gggaacgaaa gagaagctct atctcccctc caggagccca  60
gctatgaact ccttctccac aagcgccttc ggtccagttg ccttctccct ggggctgctc  120
ctggtgttgc ctgctgcctt ccctgcccca gtacccccag gagaagattc caaagatgta  180
gccgccccac acagacagcc actcacctct tcagaacgaa ttgacaaaca aattcggtac  240
atcctcgacg gcatctcagc cctgagaaag gagacatgta acaagagtaa catgtgtgaa  300
agcagcaaag aggcactggc agaaaacaac ctgaaccttc caaagatggc tgaaaaagat  360
ggatgcttcc aatctggatt caatgaggag acttgcctgg tgaaaatcat cactggtctt  420
ttggagtttg aggtatacct agagtacctc cagaacagat ttgagagtag tgaggaacaa  480
gccagagctg tgcagatgag tacaaaagtc ctgatccagt tcctgcagaa aaaggcaaag  540
aatctagatg caataaccac ccctgaccca accacaaatg ccagcctgct gacgaagctg  600
caggcacaga accagtggct gcaggacatg acaactcatc tcattctgcg cagctttaag  660
gagttcctgc agtccagcct gagggctctt cggcaaatgt agcatgggca cctcagattg  720
ttgttgttaa tgggcattcc ttcttctggt cagaaacctg tccactgggc acagaactta  780
tgttgttctc tatggagaac taaaagtatg agcgttagga cactatttta attattttta  840
atttattaat atttaaatat gtgaagctga gttaatttat gtaagtcata tttatatttt  900
taagaagtac cacttgaaac attttatgta ttagttttga aataataatg gaaagtggct  960
atgcagtttg aatatccttt gtttcagagc cagatcattt cttggaaagt gtaggcttac  1020
ctcaaataaa tggctaactt atacatattt ttaaagaaat atttatattg tatttatata  1080
atgtataaat ggtttttata ccaataaatg gcattttaaa aaattca                1127

SEQ ID NO: 491         moltype = AA  length = 177
FEATURE                Location/Qualifiers
source                 1..177
                       mol_type = protein
                       organism = Homo sapiens
SEQUENCE: 491
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH      177

SEQ ID NO: 492         moltype = DNA  length = 2016
FEATURE                Location/Qualifiers
source                 1..2016
                       mol_type = other DNA
                       organism = Homo sapiens
SEQUENCE: 492
acacttgtgg cttccgtgca cacattaaca actcatggtt ctagctccca gtcgccaagc  60
gttgccaagg cgttgagaga tcatctggga agtcttttac ccagaattgc tttgattcag  120
gccagctggt ttttcctgcg gtgattcgga aattcgcgaa ttcctctggt cctcatccag  180
gtgcgcggga agcaggtgcc caggagagag gggataatga agattccatg ctgatgatcc  240
caaagattga acctgcagac caagcgcaaa gtagaaactg aaagtacact gctggcggat  300
cctacggaag ttatggaaaa ggcaaagcgc agagccacgc cgtagtgtgt gccgcccccc  360
ttgggatgga tgaaactgca gtcgcggcgt gggtaagagg aaccagctgc agagatcacc  420
ctgcccaaca cagactcggc aactccgcgg aagaccaggg tcctgggagt gactatgggc  480
ggtgagagct tgctcctgct ccagttgcgg tcatcatgac tacgcccgcc tcccgcagac  540
catgttccat gtttctttta ggtatatctt tggacttcct cccctgatcc ttgttctgtt  600
gccagtagca tcatctgatt gtgatattga aggtaaagat ggcaaacaat atgagagtgt  660
tctaatggtc agcatcgatc aattattgga cagcatgaaa gaaattggta gcaattgcct  720
gaataatgaa tttaactttt ttaaaagaca tatctgtgat gctaataagg aaggtatgtt  780
tttattccgt gctgctcgca agttgaggca atttcttaaa atgaatagca ctggtgattt  840
tgatctccac ttattaaaag tttcagaagg cacaacaata ctgttgaact gcactggcca  900
ggttaaagga agaaaaccag ctgccctggg tgaagcccaa ccaacaaaga gtttggaaga  960
aaataaatct ttaaaggaac agaaaaaact gaatgacttg tgtttcctaa agagactatt  1020
```

-continued

```
acaagagata aaaacttgtt ggaataaaat tttgatgggc actaaagaac actgaaaaat  1080
atggagtggc aatatagaaa cacgaacttt agctgcatcc tccaagaatc tatctgctta  1140
tgcagttttt cagagtggaa tgcttcctag aagttactga atgcaccatg gtcaaaacgg  1200
attagggcat ttgagaaatg catattgtat tactagaaga tgaatacaaa caatggaaac  1260
tgaatgctcc agtcaacaaa ctatttctta tatatgtgaa catttatcaa tcagtataat  1320
tctgtactga tttttgtaag acaatccatg taaggtatca gttgcaataa tacttctcaa  1380
acctgtttaa atatttcaag acattaaatc tatgaagtat ataatggttt caaagattca  1440
aaattgacat tgctttactg tcaaaataat tttatggctc actatgaatc tattatactg  1500
tattaagagt gaaaattgtc ttcttctgtg ctggagatgt tttagagtta acaatgatat  1560
atggataatg ccggtgagaa taagagagtc ataaacctta agtaagcaac agcataacaa  1620
ggtccaagat acctaaaaga gatttcaaga gatttaatta atcatgaatg tgtaacacag  1680
tgccttcaat aaatggtata gcaaatgttt tgacatgaaa aaaggacaat ttcaaaaaaa  1740
taaaataaaa taaaaataaa ttcacctagt ctaaggatgc taaaccttag tactgagtta  1800
cattgtcatt tatatagatt ataacttgtc taaataagtt tgcaatttgg gagatatatt  1860
tttaagataa taatatatgt ttacctttta attaatgaaa tatctgtatt taattttgac  1920
actatatctg tatataaaat attttcatac agcattacaa attgcttact ttggaataca  1980
tttctccttt gataaaataa atgagctatg tattaa                          2016

SEQ ID NO: 493         moltype = AA  length = 219
FEATURE                Location/Qualifiers
source                 1..219
                       mol_type = protein
                       organism = Homo sapiens
SEQUENCE: 493
MCPARSLLLV ATLVLLDHLS LARNLPVATP DPGMFPCLHH SQNLLRAVSN MLQKARQTLE  60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                        219

SEQ ID NO: 494         moltype = DNA  length = 762
FEATURE                Location/Qualifiers
source                 1..762
                       mol_type = other DNA
                       organism = Homo sapiens
SEQUENCE: 494
atgtggcccc ctgggtcagc ctcccagcca ccgccctcac ctgccgcggc cacaggtctg  60
catccagcgg ctcgccctgt gtccctgcag tgccggctca gcatgtgtcc agcgcgcagc  120
ctcctccttg tggctaccct ggtcctcctg gaccacctca gtttggccag aaacctcccc  180
gtggccactc cagacccagg aatgttccca tgccttcacc actcccaaaa cctgctgagg  240
gccgtcagca acatgctcca gaaggccaga caaactctag aattttaccc ttgcacttct  300
gaagagattg atcatgaaga tatcacaaaa gataaaacca gcacagtgga ggcctgttta  360
ccattggaat taaccaagaa tgagagttgc ctaaattcca gagagacctc tttcataact  420
aatgggagtt gcctggcctc cagaaagacc tcttttatga tggccctgtg ccttagtagt  480
atttatgaag acttgaagat gtaccaggtg gagttcaaga ccatgaatgc aaagcttctg  540
atggatccta agaggcagat ctttctagat caaaacatgc tggcagttat tgatgagctg  600
atgcaggccc tgaatttcaa cagtgagact gtgccacaaa aatcctccct tgaagaaccg  660
gatttttata aaactaaaat caagctctgc atacttcttc atgctttcag aattcgggca  720
gtgactattg atagagtgat gagctatctg aatgcttcct aa                    762

SEQ ID NO: 495         moltype = AA  length = 28
FEATURE                Location/Qualifiers
REGION                 1..28
                       note = Description of Artificial Sequence: Synthetic peptide
REGION                 1..28
                       note = See specification as filed for detailed description
                        of substitutions and preferred embodiments
source                 1..28
                       mol_type = protein
                       organism = synthetic construct
SITE                   2
                       note = Lys, Cys or an Azido-containing amino acid
SEQUENCE: 495
AXDQDNPWRA YLDLLFPTDT LLLDLLWA                                    28

SEQ ID NO: 496         moltype = AA  length = 35
FEATURE                Location/Qualifiers
REGION                 1..35
                       note = Description of Artificial Sequence: Synthetic
                        polypeptide
REGION                 1..35
                       note = See specification as filed for detailed description
                        of substitutions and preferred embodiments
source                 1..35
                       mol_type = protein
                       organism = synthetic construct
SITE                   2
                       note = Lys, Cys or an Azido-containing amino acid
SITE                   13
                       note = Lys, Cys or an Azido-containing amino acid
```

-continued

```
REGION                  3..12
                        note = This region may encompass 1-10 residues
SEQUENCE: 496
AXXXXXXXXX XXXPWRAYLD LLFPTDTLLL DLLWA                          35

SEQ ID NO: 497          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 497
QDNDQN                                                          6

SEQ ID NO: 498          moltype = DNA  length = 308
FEATURE                 Location/Qualifiers
source                  1..308
                        mol_type = other DNA
                        organism = Homo sapiens
SEQUENCE: 498
ccagtctcag caccatgaat caaactgcca ttctgatttg ctgccttatc tttctgactc  60
taagtggcat tcaaggagta cctctctcta gaactgtacg ctgtacctgc atcagcatta  120
gtaatcaacc tgttaatcca aggtctttag aaaaacttga aattattcct gcaagccaat  180
tttgtccacg tgttgagatc attgctacaa tgaaaaagaa gggtgagaag agatgtctga  240
atccagaatc gaaggccatc aagaatttac tgaaagcagt tagcaaggaa aggtctaaaa  300
gatctcct                                                        308

SEQ ID NO: 499          moltype =   length =
SEQUENCE: 499
000

SEQ ID NO: 500          moltype = DNA  length = 729
FEATURE                 Location/Qualifiers
misc_feature            1..729
                        note = Description of Artificial Sequence: Synthetic
                         polynucleotide
source                  1..729
                        mol_type = other DNA
                        organism = synthetic construct
SEQUENCE: 500
aatggcggca ccttcgagaa gcagatcggc gaggtgaagc ccaggaccac ccctgccgcc  60
gggggaatgg acgagtctgt ggtcctggag cccgaagcca caggcgaaag cagtagcctg  120
gagccgactc cttcttccca ggaagcacag agggccctgg ggacctcccc agagctgccg  180
acgggtgtga ctggttcctc agggaccagg ctccccccga cgccaaaggc tcaggatgga  240
gggcctgtgg gcacggagct tttccgagtg cctcccgtct ccactgccgc cacgtggcag  300
agttctgctc cccaccaacc tgggcccagc ctctgggctg aggcaaagac ctctgaggcc  360
ccgtccaccc aggacccctc cacccaggcc tccactgcgt cctccccagc cccagaggag  420
aatgctccgt ctgaaggcca gcgtgtgtgg ggtcaggggc agagccccag gccagagaac  480
tctctggagc gggaggagat gggtcccgtg ccagcgcaca cggatgcctt ccaggactgg  540
gggcctggca gcatggccca cgtctctgtg gtccctgtct cctcagaagg gacccccagc  600
agggagccag tggcttcagg cagctggacc cctaaggctg aggaacccat ccatgccacc  660
atggaccccc agaggctggg cgtccttatc actcctgtcc ctgacgccca ggctgccacc  720
cggaggcag                                                       729

SEQ ID NO: 501          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 501
AEQNPIY                                                         7

SEQ ID NO: 502          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 502
DADEGT                                                          6

SEQ ID NO: 503          moltype = AA  length = 28
FEATURE                 Location/Qualifiers
REGION                  1..28
                        note = Description of Artificial Sequence: Synthetic peptide
```

-continued

```
source                  1..28
                        mol_type = protein
                        organism = synthetic construct
SEQUENCE: 503
ACDQDNPWRA YLDLLFPTDT LLLDLLWA                                       28

SEQ ID NO: 504          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 504
AKDQDNPWRA YLDLLFPTDT LLLDLLWA                                       28

SEQ ID NO: 505          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 505
ACQDNDQNCP WRAYLDLLFP TDTLLLDLLW A                                   31

SEQ ID NO: 506          moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 506
AKQDNDQNKP WRAYLDLLFP TDTLLLDLLW A                                   31

SEQ ID NO: 507          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 507
WWWWWC                                                               6

SEQ ID NO: 508          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 508
WWWWC                                                                5

SEQ ID NO: 509          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 509
ACDDQNPWRA YLDLLFPTDT LLLDLLWA                                       28

SEQ ID NO: 510          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 510
AKDDQNPWRA YLDLLFPTDT LLLDLLWA                                       28

SEQ ID NO: 511          moltype = AA  length = 31
```

-continued

```
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 511
AKQNDDQNKP WRAYLDLLFP TDTLLLDLLW A                                 31

SEQ ID NO: 512         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 512
YPYDVPDYAG GGCA                                                    14

SEQ ID NO: 513         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 513
QNDDQN                                                             6

SEQ ID NO: 514         moltype = AA  length = 98
FEATURE                Location/Qualifiers
source                 1..98
                       mol_type = protein
                       organism = Homo sapiens
SEQUENCE: 514
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSP                          98

SEQ ID NO: 515         moltype = AA  length = 35
FEATURE                Location/Qualifiers
REGION                 1..35
                       note = Description of Artificial Sequence: Synthetic
                        polypeptide
REGION                 3..12
                       note = This region may encompass 1-10 residues
REGION                 1..35
                       note = See specification as filed for detailed description
                        of substitutions and preferred embodiments
source                 1..35
                       mol_type = protein
                       organism = synthetic construct
SEQUENCE: 515
AXXXXXXXXX XXXPWRAYLD LLFPTDTLLL DLLWA                             35

SEQ ID NO: 516         moltype = AA  length = 30
FEATURE                Location/Qualifiers
source                 1..30
                       mol_type = protein
                       organism = Homo sapiens
SEQUENCE: 516
MELAALCRWG LLLALLPPGA ASTQVCTGTD                                   30

SEQ ID NO: 517         moltype = DNA  length = 1175
FEATURE                Location/Qualifiers
source                 1..1175
                       mol_type = other DNA
                       organism = Homo sapiens
SEQUENCE: 517
gagacattcc tcaattgctt agacatattc tgagcctaca gcagaggaac ctccagtctc  60
agcaccatga atcaaactgc cattctgatt tgctgcctta tctttctgac tctaagtggc  120
attcaaggag tacctctctc tagaactgta cgctgtacct gcatcagcat tagtaatcaa  180
cctgttaatc caaggtcttt agaaaaactt gaaattattc ctgcaagcca attttgtcca  240
cgtgttgaga tcattgctac aatgaaaaag aagggtgaga agagatgtct gaatccagaa  300
tcgaaggcca tcaagaattt actgaaagca gttagcaagg aaaggtctaa aagatctcct  360
taaaaccaga ggggagcaaa atcgatgcag tgcttccaag gatggaccac acagaggctg  420
cctctcccat cacttcccta catggagtat atgtcaagcc ataattgttc ttagtttgca  480
gttacactaa aaggtgacca atgatggtca ccaaatcagc tgctactact cctgtaggaa  540
ggttaatgtt catcatccta agctattcag taataactct accctggcac tataatgtaa  600
```

```
gctctactga ggtgctatgt tcttagtgga tgttctgacc ctgcttcaaa tatttccctc  660
acctttccca tcttccaagg gtactaagga atctttctgc tttggggttt atcagaattc  720
tcagaatctc aaataactaa aaggtatgca atcaaatctg ctttttaaag aatgctcttt  780
acttcatgga cttccactgc catcctccca aggggcccaa attctttcag tggctaccta  840
catacaattc caaacacata caggaaggta gaaatatctg aaaatgtatg tgtaagtatt  900
cttatttaat gaaagactgt acaaagtaga agtcttagat gtatatattt cctatattgt  960
tttcagtgta catggaataa catgtaatta agtactatgt atcaatgagt aacaggaaaa  1020
ttttaaaaat acagatagat atatgctctg catgttacat aagataaatg tgctgaatgg  1080
ttttcaaaat aaaaatgagg tactctcctg gaaatattaa gaaagactat ctaaatgttg  1140
aaagatcaaa aggttaataa agtaattata actaa                           1175

SEQ ID NO: 518         moltype = AA  length = 125
FEATURE                Location/Qualifiers
source                 1..125
                       mol_type = protein
                       organism = Homo sapiens
SEQUENCE: 518
MKKSGVLFLL GIILLVLIGV QGTPVVRKGR CSCISTNQGT IHLQSLKDLK QFAPSPSCEK  60
IEIIATLKNG VQTCLNPDSA DVKELIKKWE KQVSQKKKQK NGKKHQKKKV LKVRKSQRSR  120
QKKTT                                                            125

SEQ ID NO: 519         moltype = DNA  length = 2761
FEATURE                Location/Qualifiers
source                 1..2761
                       mol_type = other DNA
                       organism = Homo sapiens
SEQUENCE: 519
aaagaatttc tcaggctcaa aatccaatac aggagtgact tggaactcca ttctatcact  60
atgaagaaaa gtggtgttct tttcctcttg ggcatcatct tgctggttct gattggagtg  120
caaggaaccc cagtagtgag aaagggtcgc tgttcctgca tcagcaccaa ccaagggact  180
atccacctac aatccttgaa agaccttaaa caatttgccc caagcccttc ctgcgagaaa  240
attgaaatca ttgctacact gaagaatgga gttcaaacat gtctaaaccc agattcagca  300
gatgtgaagg aactgattaa aaagtgggag aaacaggtca gccaaaagaa aaagcaaaag  360
aatgggaaaa aacatcaaaa aaagaaagtt ctgaaagttc gaaaatctca acgttctcgt  420
caaaagaaga ctacataaga gaccacttca ccaataagta ttctgtgtta aaaatgttct  480
attttaatta taccgctatc attccaaagg aggatggcat ataatacaaa ggcttattaa  540
tttgactaga aaatttaaaa cattactctg aaattgtaac taaagttaga aagttgattt  600
taagaatcca aacgttaaga attgttaaag gctatgattg tctttgttct tctaccaccc  660
accagttgaa tttcatcatg cttaaggcca tgattttagc aatacccatg tctacacaga  720
tgttcaccca accacatccc actcacaaca gctgcctgga agagcagccc taggcttcca  780
cgtactgcag cctccagaga gtatctgagg cacatgtcag caagtcctaa gcctgttagc  840
atgctggtga gccaagcagt ttgaaattga gctggacctc accaagctgc tgtggccatc  900
aacctctgta tttgaatcag cctacaggcc tcacacacaa tgtgtctgag agattcatgc  960
tgattgttat tgggtatcac cactggagat caccagtgtg tggctttcag agcctccttt  1020
ctggctttgg aagccatgtg attccatctt gcccgctcag gctgaccact ttatttcttt  1080
ttgttcccct ttgcttcatt caagtcagct cttctccatc ctaccacaat gcagtgcctt  1140
tcttctctcc agtgcacctg tcatatgctc tgatttatct gagtcaactc ctttctcatc  1200
ttgtccccaa caccccacag aagtgctttc ttctcccaat tcatcctcac tcagtccagc  1260
ttagttcaag tcctgcctct taaataaacc tttttggaca cacaaattat cttaaaactc  1320
ctgtttcact tggttcagta ccacatgggt gaacactcaa tggttaacta attcttgggt  1380
gtttatccta tctctccaac cagattgtca gctccttgag ggcaagagcc acagtatatt  1440
tccctgtttc ttccacagtg cctaataata ctgtggaact aggttttaat aattttttaa  1500
ttgatgttgt tatgggcagg atggcaacca gaccattgtc tcagagcagg tgctggctct  1560
ttcctggcta ctccatgttg gctagcctct ggtaacctct tacttattat cttcaggaca  1620
ctcactacag ggaccaggga tgatgcaaca tccttgtctt tttatgacag gatgtttgct  1680
cagcttctcc aacaataaga agcacgtggt aaaacacttg cggatattct ggactgtttt  1740
taaaaaatat acagtttacc gaaaatcata taatcttaca atgaaaagga ctttatagat  1800
cagccagtga ccaacctttt cccaaccata caaaaattcc ttttcccgaa ggaaaagggc  1860
tttctcaata agcctcagct ttctaagatc taacaagata gccaccgaga tccttatcga  1920
aactcatttt aggcaaatat gagttttatt gtccgtttac ttgtttcaga gtttgtattg  1980
tgattatcaa ttaccacacc atctcccatg aagaaaggga acggtgaagt actaagcgct  2040
agaggaagca gccaagtcgg ttagtggaag catgattggt gcccagttag cctctgcagg  2100
atgtggaaac ctccttccag gggaggttca gtgaattgtg taggagaggt tgtctgtggc  2160
cagaatttaa acctatactc actttcccaa attgaatcac tgctcacact gctgatgatt  2220
tagagtgctg tccggtggag atcccacccg aacgtcttat ctaatcatga aactccctag  2280
ttccttcatg taacttccct gaaaaatcta agtgtttcat aaatttgaga gtctgtgacc  2340
cacttacctt gcatctcaca ggtagacagt atataactaa caaccaaaga ctacatattg  2400
tcactgacac acacgttata atcatttatc atatatatac atacatgcat acactctcaa  2460
agcaaataat ttttcacttc aaaacagtat tgacttgtat accttgtaat ttgaaatatt  2520
ttctttgtta aaatagaatg gtatcaataa atagaccatt aatcagaaaa cagatcttga  2580
ttttttttct cttgaatgta cccttcaact gttgaatgtt taatagtaaa tcttatatgt  2640
ccttatttac tttttagctt tctctcaaat aaagtgtaac actagttgag ataacacatg  2700
aaagctcttt aaagggtcga tcgggaacag gaaaaaaaac ctatggaaaa tatgacaaca  2760
c                                                                2761

SEQ ID NO: 520         moltype = AA  length = 94
FEATURE                Location/Qualifiers
source                 1..94
                       mol_type = protein
```

```
                         organism = Homo sapiens
SEQUENCE: 520
MSVKGMAIAL AVILCATVVQ GFPMFKRGRC LCIGPGVKAV KVADIEKASI MYPSNNCDKI  60
EVIITLKENK GQRCLNPKSK QARLIIKKVE RKNF                             94

SEQ ID NO: 521           moltype = DNA  length = 1479
FEATURE                  Location/Qualifiers
source                   1..1479
                         mol_type = other DNA
                         organism = Homo sapiens
SEQUENCE: 521
gttcagcatt tctactcctt ccaagaagag cagcaaagct gaagtagcag cagcagcacc  60
agcagcaaca gcaaaaaaca aacatgagtg tgaagggcat ggctatagcc ttggctgtga  120
tattgtgtgc tacagttgtt caaggcttcc ccatgttcaa aagaggacgc tgtctttgca  180
taggccctgg ggtaaaagca gtgaaagtgg cagatattga gaaagcctcc ataatgtacc  240
caagtaacaa ctgtgacaaa atagaagtga ttattaccct gaaagaaaat aaaggacaac  300
gatgcctaaa tcccaaatcg aagcaagcaa ggcttataat caaaaaagtt gaaagaaaga  360
atttttaaaa atatcaaaac atatgaagtc ctggaaaaga gcatctgaaa aacctagaac  420
aagtttaact gtgactactg aaatgacaag aattctacag taggaaactg agacttttct  480
atggttttgt gactttcaac ttttgtacag ttatgtgaag gatgaaaggt gggtgaaagg  540
accaaaaaca gaaatacagt cttcctgaat gaatgacaat cagaattcca ctgcccaaag  600
gagtccaaca attaaatgga tttctaggaa aagctacctt aagaaaggct ggttaccatc  660
ggagtttaca aagtgctttc acgttcttac ttgttgcatt atacattcat gcatttctag  720
gctagagaac cttctagatt tgatgcttac aactattctg ttgtgactat gagaacattt  780
ctgtctctag aagtcatctg tctgtattga tctttatgct atattactat ctgtggttac  840
ggtggagaca ttgacattat tactggagtc aagcccttat aagtcaaaag catctatgtg  900
tcgtaaaaca ttcctcaaac attttttcat gcaaatacac acttctttcc ccaaacatca  960
tgtagcacat caatatgtag ggagacattc ttatgcatca tttggtttgt tttataacca  1020
attcattaaa tgtaattcat aaaatgtact atgaaaaaaa ttatacgcta tgggatactg  1080
gcaaaagtgc acatatttca taaccaaatt agtagcacca gtcttaattt gatgtttttc  1140
aacttttatt cattgagatg ttttgaagca attaggatat gtgtgtttac tgtacttttt  1200
gttttgatcc gtttgtataa atgatagcaa tatcttggac acatctgaaa tacaaaatgt  1260
ttttgtctac caaagaaaaa tgttgaaaaa taagcaaatg tatacctagc aatcactttt  1320
actttttgta attctgtctc ttagaaaaat acataatcta atcaatttct ttgttcatgc  1380
ctatatactg taaaatttag gtatactcaa gactagttta aagaatcaaa gtcatttttt  1440
tctctaataa actaccacaa cctttctttt ttaaaaaaa                        1479

SEQ ID NO: 522           moltype = AA  length = 233
FEATURE                  Location/Qualifiers
source                   1..233
                         mol_type = protein
                         organism = Homo sapiens
SEQUENCE: 522
MSTESMIRDV ELAEEALPKK TGGPQGSRRC LFLSLFSFLI VAGATTLFCL LHFGVIGPQR  60
EEFPRDLSLI SPLAQAVRSS SRTPSDKPVA HVVANPQAEG QLQWLNRRAN ALLANGVELR  120
DNQLVVPSEG LYLIYSQVLF KGQGCPSTHV LLTHTISRIA VSYQTKVNLL SAIKSPCQRE  180
TPEGAEAKPW YEPIYLGGVF QLEKGDRLSA EINRPDYLDF AESGQVYFGI IAL         233

SEQ ID NO: 523           moltype = DNA  length = 1678
FEATURE                  Location/Qualifiers
source                   1..1678
                         mol_type = other DNA
                         organism = Homo sapiens
SEQUENCE: 523
agcagacgct ccctcagcaa ggacagcaga ggaccagcta agagggagag aagcaactac  60
agaccccccc tgaaaacaac cctcagacgc cacatcccct gacaagctgc caggcaggtt  120
ctcttcctct cacatactga cccacggctc caccctctct cccctggaaa ggacaccatg  180
agcactgaaa gcatgatccg ggacgtggag ctggccgagg aggcgctccc caagaagaca  240
ggggggcccc agggctccag gcggtgcttg ttcctcagcc tcttctcctt cctgatcgtg  300
gcaggcgcca ccacgctctt ctgcctgctg cactttggag tgatcggccc ccagagggaa  360
gagttcccca gggacctctc tctaatcagc cctctggccc aggcagtcag atcatcttct  420
cgaaccccga gtgacaagcc tgtagcccat gttgtagcaa accctcaagc tgaggggcag  480
ctccagtggc tgaaccgccg ggccaatgcc ctcctggcca atggcgtgga gctgagagat  540
aaccagctgg tggtgccatc agagggcctg tacctcatct actcccaggt cctcttcaag  600
ggccaaggct gcccctccac ccatgtgctc ctcacccaca ccatcagccg catcgccgtc  660
tcctaccaga ccaaggtcaa cctcctctct gccatcaaga gcccctgcca gagggagacc  720
ccagaggggg ctgaggccaa gccctggtat gagcccatct atctgggagg ggtcttccag  780
ctggagaagg gtgaccgact cagcgctgag atcaatcggc ccgactatct cgactttgcc  840
gagtctgggc aggtctactt tgggatcatt gccctgtgag gaggacgaac atccaacctt  900
cccaaacgcc tcccctgccc caatcccttt attacccct ccttcagaca ccctcaacct  960
cttctggctc aaaaagagaa ttgggggctt agggtcggaa cccaagctta gaactttaag  1020
caacaagacc accacttcga aacctgggat tcaggaatgt gtggcctgca cagtgaagtg  1080
ctggcaacca ctaagaattc aaactggggc ctccagaact cactggggcc tacagctttg  1140
atccctgaca tctggaatct ggagaccagg gagcctttgg ttctggccag aatgctgcag  1200
gacttgagaa gacctcacct agaaattgac acaagtggac cttaggcctt cctctctcca  1260
gatgtttcca gacttccttg agacacggag cccagccctc cccatggagc cagctccctc  1320
tatttatgtt tgcacttgtg attatttatt atttatttat tatttattta tttacagatg  1380
aatgtattta tttgggagac cggggtatcc tgggggaccc aatgtaggag ctgccttggc  1440
tcagacatgt tttccgtgaa aacggagctg aacaataggc tgttcccatg tagcccctg   1500
```

-continued

```
gcctctgtgc cttcttttga ttatgttttt taaaatattt atctgattaa gttgtctaaa  1560
caatgctgat ttggtgacca actgtcactc attgctgagc ctctgctccc caggggagtt  1620
gtgtctgtaa tcgccctact attcagtggc gagaaataaa gtttgcttag aaaagaaa    1678

SEQ ID NO: 524          moltype = AA  length = 328
FEATURE                 Location/Qualifiers
source                  1..328
                        mol_type = protein
                        organism = Homo sapiens
SEQUENCE: 524
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                     328

SEQ ID NO: 525          moltype = DNA  length = 2364
FEATURE                 Location/Qualifiers
source                  1..2364
                        mol_type = other DNA
                        organism = Homo sapiens
SEQUENCE: 525
agaagaaaca acatctgttt cagggccatt ggactctccg tcctgcccag agcaagatgt  60
gtcaccagca gttggtcatc tcttggtttt ccctggtttt tctggcatct cccctcgtgg  120
ccatatggga actgaagaaa gatgtttatg tcgtagaatt ggattggtat ccggatgccc  180
ctggagaaat ggtggtcctc acctgtgaca cccctgaaga agatggtatc acctggacct  240
tggaccagag cagtgaggtc ttaggctctg gcaaaaccct gaccatccaa gtcaaagagt  300
ttggagatgc tggccagtac acctgtcaca aaggaggcga ggttctaagc cattcgctcc  360
tgctgcttca caaaaaggaa gatggaattt ggtccactga tattttaaag gaccagaaag  420
aacccaaaaa taagaccttt ctaagatgcg aggccaagaa ttattctgga cgtttcacct  480
gctggtggct gacgacaatc agtactgatt tgacattcag tgtcaaaagc agcagaggct  540
cttctgaccc ccaaggggtg acgtgcggag ctgctacact ctctgcagag agagtcagag  600
gggacaacaa ggagtatgag tactcagtgg agtgccagga ggacagtgcc tgcccagctg  660
ctgaggagag tctgcccatt gaggtcatgg tggatgccgt tcacaagctc aagtatgaaa  720
actacaccag cagcttcttc atcagggaca tcatcaaacc tgacccaccc aagaacttgc  780
agctgaagcc attaaagaat tctcggcagg tggaggtcag ctgggagtac cctgacacct  840
ggagtactcc acattcctac ttctccctga cattctgcgt tcaggtccag ggcaagagca  900
agagagaaaa gaaagataga gtcttcacgg acaagacctc agccacggtc atctgccgca  960
aaaatgccag cattagcgtg cgggcccagg accgctacta tagctcatct tggagcgaat  1020
gggcatctgt gccctgcagt taggttctga tccaggatga aaatttggag gaaaagtgga  1080
agatattaag caaaatgttt aaagacacaa cggaatagac ccaaaaagat aatttctatc  1140
tgatttgctt taaaacgttt ttttaggatc acaatgatat ctttgctgta tttgtatagt  1200
tagatgctaa atgctcattg aaacaatcag ctaatttatg tatagatttt ccagctctca  1260
agttgccatg ggccttcatg ctatttaaat atttaagtaa tttatgtatt tattagtata  1320
ttactgttat ttaacgtttg tctgccagga tgtatggaat gtttcatact cttatgacct  1380
gatccatcag gatcagtccc tattatgcaa aatgtgaatt taattttatt tgtactgaca  1440
acttttcaag caaggctgca agtacatcag ttttatgaca atcaggaaga atgcagtgtt  1500
ctgataccag tgccatcata cacttgtgat ggatgggaac gcaagagata cttacatgga  1560
aacctgacaa tgcaaacctg ttgagaagat ccaggagaac aagatgctag ttcccatgtc  1620
tgtgaagact tcctggagat ggtgttgata aagcaattta gggccactta cacttctaag  1680
caagtttaat ctttggatgc ctgaatttta aaagggctag aaaaaaatga ttgaccagcc  1740
tgggaaacat aacaagaccc cgtctctaca aaaaaaattt aaaattagcc aggcgtggtg  1800
gctcatgctt gtggtcccag ctgttcagga ggatgaggca ggaggatctc ttgagcccag  1860
gaggtcaagg ctatggtgag ccgtgattgt gccactgcat accagcctag gtgacagaat  1920
gagaccctgt ctcaaaaaaa aaaatgattg aaattaaaat tcagctttag cttccatggc  1980
agtcctcacc cccacctctc taaaagacac aggaggatga cacagaaaca ccgtaagtgt  2040
ctggaaggca aaaagatctt aagattcaag agagaggaca agtagttatg gctaaggaca  2100
tgaaattgtc agaatggcag gtggcttctt aacagccctg tgagaagcag acagatgcaa  2160
agaaaatctg gaatcccttt ctcattagca tgaatgaacc tgatacacaa ttatgaccag  2220
aaaatatggc tccatgaagg tgctactttt aagtaatgta tgtgcgctct gtaaagtgat  2280
tacatttgtt tcctgtttgt ttatttattt atttattttt gcattctgag gctgaactaa  2340
taaaaactct tctttgtaat cata                                         2364

SEQ ID NO: 526          moltype = AA  length = 241
FEATURE                 Location/Qualifiers
source                  1..241
                        mol_type = protein
                        organism = Homo sapiens
SEQUENCE: 526
GTFEKQIGEV KPRTTPAAGG MDESVVLEPE ATGESSSLEP TPSSQEAQRA LGTSPELPTG  60
VTGSSGTRLP PTPKAQDGGP VGTELFRVPP VSTAATWQSS APHQPGPSLW AEAKTSEAPS  120
TQDPSTQAST ASSPAPEENA PSEGQRVWGQ GQSPRPENSL EREEMGPVPA HTDAFQDWGP  180
GSMAHVSVVP VSSEGTPSRE PVASGSWTPK AEEPIHATMD PQRLGVLITP VPDAQAATRR  240
Q                                                                  241

SEQ ID NO: 527          moltype = AA  length = 397
FEATURE                 Location/Qualifiers
source                  1..397
```

```
                        mol_type = protein
                        organism = Homo sapiens
SEQUENCE: 527
MAPISLSWLL RLATFCHLTV LLAGQHHGVT KCNITCSKMT SKIPVALLIH YQQNQASCGK  60
RAIILETRQH RLFCADPKEQ WVKDAMQHLD RQAAALTRNG GTFEKQIGEV KPRTTPAAGG  120
MDESVVLEPE ATGESSSLEP TPSSQEAQRA LGTSPELPTG VTGSSGTRLP PTPKAQDGGP  180
VGTELFRVPP VSTAATWQSS APHQPGPSLW AEAKTSEAPS TQDPSTQAST ASSPAPEENA  240
PSEGQRVWGQ GQSPRPENSL EREEMGPVPA HTDAFQDWGP GSMAHVSVVP VSSEGTPSRE  300
PVASGSWTPK AEEPIHATMD PQRLGVLITP VPDAQAATRR QAVGLLAFLG LLFCLGVAMF  360
TYQSLQGCPR KMAGEMAEGL RYIPRSCGSN SYVLVPV                          397

SEQ ID NO: 528          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 528
NENENN                                                            6

SEQ ID NO: 529          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 529
NDNDNN                                                            6

SEQ ID NO: 530          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 530
NDNDNDN                                                           7

SEQ ID NO: 531          moltype = AA  length = 385
FEATURE                 Location/Qualifiers
REGION                  1..385
                        note = Description of Artificial Sequence: Synthetic
                         polypeptide
source                  1..385
                        mol_type = protein
                        organism = synthetic construct
SEQUENCE: 531
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSPGT FEKQIGEVKP RTTPAAGGMD  120
ESVVLEPEAT GESSSLEPTP SSQEAQRALG TSPELPTGVT GSSGTRLPPT PKAQDGGPVG  180
TELFRVPPVS TAATWQSSAP HQPGPSLWAE AKTSEAPSTQ DPSTQASTAS SPAPEENAPS  240
EGQRVWGQGQ SPRPENSLER EEMGPVPAHT DAFQDWGPGS MAHVSVVPVS SEGTPSREPV  300
ASGSWTPKAE EPIHATMDPQ RLGVLITPVP DAQAATRRQE QKLISEEDLE QKLISEEDLA  360
DDQNPWRAYL DLLFPTDTLL LDLLW                                       385

SEQ ID NO: 532          moltype = AA  length = 371
FEATURE                 Location/Qualifiers
REGION                  1..371
                        note = Description of Artificial Sequence: Synthetic
                         polypeptide
source                  1..371
                        mol_type = protein
                        organism = synthetic construct
SEQUENCE: 532
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSPGT FEKQIGEVKP RTTPAAGGMD  120
ESVVLEPEAT GESSSLEPTP SSQEAQRALG TSPELPTGVT GSSGTRLPPT PKAQDGGPVG  180
TELFRVPPVS TAATWQSSAP HQPGPSLWAE AKTSEAPSTQ DPSTQASTAS SPAPEENAPS  240
EGQRVWGQGQ SPRPENSLER EEMGPVPAHT DAFQDWGPGS MAHVSVVPVS SEGTPSREPV  300
ASGSWTPKAE EPIHATMDPQ RLGVLITPVP DAQAATRRQH HHHHHADDQN PWRAYLDLLF  360
PTDTLLLDLL W                                                      371

SEQ ID NO: 533          moltype = AA  length = 27
FEATURE                 Location/Qualifiers
source                  1..27
                        mol_type = protein
```

```
                         organism = synthetic construct
REGION                   1..27
                         note = Pept
UNSURE                   2
                         note = X is a functional group, selected from a lysine, a
                          cysteine, or an Azido-containing amino acid
SEQUENCE: 533
AXDDQNPWRA YLDLLFPTDT LLLDLLW                                          27

SEQ ID NO: 534           moltype = AA  length = 27
FEATURE                  Location/Qualifiers
source                   1..27
                         mol_type = protein
                         note = Pept
                         organism = synthetic construct
UNSURE                   2
                         note = X is a functional group, selected from a lysine, a
                          cysteine, or an Azido-containing amino acid
SEQUENCE: 534
AXDQDNPWRA YLDLLFPTDT LLLDLLW                                          27

SEQ ID NO: 535           moltype = AA  length = 31
FEATURE                  Location/Qualifiers
source                   1..31
                         mol_type = protein
                         note = Pept
                         note = Pept
                         note = Pept
                         organism = synthetic construct
SEQUENCE: 535
AKQNDNDNKP WRAYLDLLFP TDTLLLDLLW A                                     31

SEQ ID NO: 536           moltype = AA  length = 31
FEATURE                  Location/Qualifiers
source                   1..31
                         mol_type = protein
                         note = Pept
                         organism = synthetic construct
SEQUENCE: 536
ACQNDDQNCP WRAYLDLLFP TDTLLLDLLW A                                     31

SEQ ID NO: 537           moltype = AA  length = 28
FEATURE                  Location/Qualifiers
source                   1..28
                         mol_type = protein
                         note = Var3-1a
                         organism = synthetic construct
SEQUENCE: 537
ACDQDNPWRA YLDLLFPTDT LLLDLLWA                                         28

SEQ ID NO: 538           moltype = AA  length = 28
FEATURE                  Location/Qualifiers
source                   1..28
                         mol_type = protein
                         organism = synthetic construct
REGION                   1..28
                         note = Var3-1b
SEQUENCE: 538
AKDQDNPWRA YLDLLFPTDT LLLDLLWA                                         28

SEQ ID NO: 539           moltype = AA  length = 31
FEATURE                  Location/Qualifiers
source                   1..31
                         mol_type = protein
                         organism = synthetic construct
REGION                   1..31
                         note = Var3-2a
SEQUENCE: 539
ACQDNDQNCP WRAYLDLLFP TDTLLLDLLW A                                     31

SEQ ID NO: 540           moltype = AA  length = 31
FEATURE                  Location/Qualifiers
source                   1..31
                         mol_type = protein
                         note = Var3-2b
                         organism = synthetic construct
REGION                   1..31
SEQUENCE: 540
AKQDNDQNKP WRAYLDLLFP TDTLLLDLLW A                                     31
```

-continued

```
SEQ ID NO: 541          moltype = AA  length = 6
FEATURE                 Location/Qualifiers
source                  1..6
                        mol_type = protein
                        note = PEG Conjugation Spacer
                        organism = synthetic construct
SEQUENCE: 541
QNDDQN                                                          6
```

What is claimed is:

1. A composition comprising an epitope linked to one or more pH-triggered peptides by a non-cleavable linker compound, wherein the composition comprises the formula of Epitope-Linker-Peptide, wherein Epitope is an antibody recruiting molecule or immune cell recruiting molecule, wherein Linker is a linker or an extension of the pH-triggered peptide, wherein Peptide is a pH-triggered peptide comprising the sequence AXDDQNPWRAYLDLLFPTDTLLLDLLWA (SEQ ID NO: 18) or AXDQDNPWRAYLDLLFPTDTLLLDLLWA (SEQ ID NO: 495), wherein upper case "X" indicates any amino acid or an Azido-containing amino acid, wherein each is a covalent bond, and wherein Epitope is a hemagglutinin peptide (HA peptide) and comprises a length of less than 50 amino acids.

2. The composition of claim 1, wherein two Epitopes are linked to a single pH-triggered peptide.

3. The composition of claim 1, wherein the HA peptide comprises the amino acid sequence of YPYDVPDYA (SEQ ID NO: 6).

4. The composition of claim 1, wherein the linker is a polyethylene glycol (PEG) linker ranging from 12 to 24 PEG units.

5. A composition comprising two antibody recruiting molecules linked to a pH-triggered peptide, wherein the composition comprises the formula of Epitope1-Linker-Peptide-Linker-Epitope1, wherein Epitope1 is an antibody recruiting molecule; wherein Linker is a PEG linker; wherein Peptide is a pH-triggered peptide comprising the sequence Ac-AKQNDDQNKPWRAYLDLLFPTDTLLLDLLWA (SEQ ID NO: 511); Ac-AKQNDNDNKPWRAYLDLLFPTDTLLLDLLWA (SEQ ID NO: 535); ACQNDDQNCPWRAYLDLLFPTDTLLLDLLWA (SEQ ID NO: 536); or ACQNDNDNCPWRAYLDLLFPTDTLLLDLLWA (SEQ ID NO: 505), wherein each-is a covalent bond, and wherein one or both of the Epitope1 is a hemagglutinin peptide (HA peptide) and comprises a length of less than 50 amino acids.

6. The composition of claim 5, wherein the HA peptide comprises the amino acid sequence of YPYDVPDYA (SEQ ID NO: 6).

7. The composition of claim 5, wherein one or both of the Epitopel is selected from the group consisting of QVSHWVSGLAEGSFG (SEQ ID NO: 1), LSHTSGRVEGSVSLL (SEQ ID NO: 2), QMWAPQWGPD (SEQ ID NO: 3); MASMTGGQQMG (SEQ ID NO: 4); EQKLISEEDL (SEQ ID NO: 5); YTDIEMNRLGK (SEQ ID NO: 7); KETAAAKFERQHMDS (SEQ ID NO: 8); GKPIPNPLLGLDST (SEQ ID NO: 9); DYKDDDDK (SEQ ID NO: 10); GAPVPYPDPLEPR (SEQ ID NO: 11); HHHHHH (SEQ ID NO: 12); TKENPRSNQEESYDDNES (SEQ ID NO: 13); WSHPQFEK (SEQ ID NO: 14); and PDRVRAVSHWSS (SEQ ID NO: 15).

8. The composition of claim 5, wherein the PEG linker ranges from 12 to 24 PEG units.

9. The composition of claim 1, wherein the composition is formulated with a pharmaceutically acceptable carrier.

10. The composition of claim 1, wherein the composition is for intravenous, subcutaneous, intraarterial, intraperitoneal, intracerebral, intracerebroventricular, intrathecal, intracardiac, intracavernous, intraosseous, intraocular, intravitreal, intramuscular, intradermal, transdermal, transmucosal, intralesional, topical, epicutaneous, extra-amniotic, intravaginal, intravesical, nasal, or oral administration.

11. The composition of claim 1, wherein the composition is for direct injection into a diseased tissue.

12. The composition of claim 11, wherein the composition preferentially targets diseased tissue compared to a healthy tissue, thereby minimizing damage to the healthy tissue.

13. The composition of claim 12, wherein the diseased tissue is a tumor or an inflamed tissue.

14. The composition of claim 5, wherein the composition is formulated with a pharmaceutically acceptable carrier.

15. The composition of claim 5, wherein the composition is for intravenous, subcutaneous, intraarterial, intraperitoneal, intracerebral, intracerebroventricular, intrathecal, intracardiac, intracavernous, intraosseous, intraocular, intravitreal, intramuscular, intradermal, transdermal, transmucosal, intralesional, topical, epicutaneous, extra-amniotic, intravaginal, intravesical, nasal, or oral administration.

16. The composition of claim 5, wherein the composition is for direct injection into a diseased tissue.

17. The composition of claim 16, wherein the composition preferentially targets diseased tissue compared to a healthy tissue, thereby minimizing damage to the healthy tissue.

18. The composition of claim 17, wherein the diseased tissue is a tumor or an inflamed tissue.

* * * * *